United States Patent
Bennett et al.

(10) Patent No.: US 10,533,178 B2
(45) Date of Patent: *Jan. 14, 2020

(54) METHODS FOR MODULATING ATAXIN 2 EXPRESSION

(71) Applicants: Ionis Pharmaceuticals, Inc., Carlsbad, CA (US); University of Utah Research Foundation, Salt Lake City, UT (US)

(72) Inventors: C. Frank Bennett, Carlsbad, CA (US); Susan M. Freier, San Diego, CA (US); Stefan M. Pulst, Salt Lake City, UT (US); Daniel R. Scoles, Salt Lake City, UT (US); Gene Hung, San Diego, CA (US)

(73) Assignees: Ionis Pharmaceuticals, Inc., Carlsbad, CA (US); University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/973,088

(22) Filed: May 7, 2018

(65) Prior Publication Data

US 2019/0017047 A1  Jan. 17, 2019

Related U.S. Application Data

(63) Continuation of application No. 15/127,352, filed as application No. PCT/US2015/021607 on Mar. 19, 2015, now Pat. No. 10,006,027.

(60) Provisional application No. 61/982,124, filed on Apr. 21, 2014, provisional application No. 61/955,704, filed on Mar. 19, 2014.

(51) Int. Cl.
*C12N 15/113* (2010.01)
*A61K 48/00* (2006.01)
*C12N 5/00* (2006.01)

(52) U.S. Cl.
CPC ........ *C12N 15/113* (2013.01); *C12N 2310/11* (2013.01); *C12N 2310/14* (2013.01); *C12N 2310/141* (2013.01); *C12N 2310/315* (2013.01); *C12N 2310/317* (2013.01); *C12N 2310/321* (2013.01); *C12N 2310/323* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |

(Continued)

FOREIGN PATENT DOCUMENTS

| | | |
|---|---|---|
| CN | 101052717 A | 10/2007 |
| CN | 101883777 A | 11/2010 |

(Continued)

OTHER PUBLICATIONS

Bezprozvanny et al., Therapeutic prospects for spinocerebellar ataxia type 2 and 3. Drugs Future. 2009; 34(12):1-17.

(Continued)

*Primary Examiner* — Sean McGarry
(74) *Attorney, Agent, or Firm* — Ballard Spahr LLP

(57) ABSTRACT

Disclosed herein are methods for decreasing Ataxin 2 mRNA and protein expression. Such methods are useful to treat, prevent, or ameliorate Ataxin 2 associated diseases, disorders, and conditions. Such Ataxin 2 associated diseases include spinocerebellar ataxia type 2 (SCA2), amyotrophic lateral sclerosis (ALS), and parkinsonism.

28 Claims, No Drawings

Specification includes a Sequence Listing.

(56) References Cited

U.S. PATENT DOCUMENTS

| | | |
|---|---|---|
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o et al. |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,673,535 B1 | 1/2004 | Pulst |
| 6,770,748 B2 | 8/2004 | Imanishi et al. |
| 6,844,431 B1 | 1/2005 | Pulst |
| 7,015,315 B1 | 3/2006 | Cook et al. |
| 7,053,207 B2 | 5/2006 | Wengel |
| 7,101,993 B1 | 9/2006 | Cook et al. |
| 7,262,177 B2 | 8/2007 | Ts'O et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,728,736 B2 | 5/2014 | Leamon et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 9/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0220132 A1 | 11/2004 | Kaemmerer |
| 2005/0042646 A1 | 2/2005 | Davidson et al. |
| 2005/0100885 A1 | 5/2005 | Crooke et al. |
| 2005/0130923 A1 | 6/2005 | Bhat et al. |
| 2005/0209178 A1 | 9/2005 | Pulst |
| 2005/0244851 A1 | 11/2005 | Blume et al. |
| 2005/0255487 A1 | 11/2005 | Khvorova et al. |
| 2006/0148740 A1 | 7/2006 | Platenburg |
| 2006/0270727 A1 | 11/2006 | Melander et al. |
| 2007/0031844 A1 | 2/2007 | Khvorova et al. |
| 2007/0224624 A1 | 9/2007 | Pulst |
| 2008/0039618 A1 | 2/2008 | Allerson et al. |
| 2008/0113351 A1 | 5/2008 | Naito et al. |
| 2010/0190837 A1 | 7/2010 | Migawa et al. |
| 2010/0197762 A1 | 8/2010 | Swayze |
| 2011/0054005 A1 | 3/2011 | Naito et al. |

(56) References Cited

U.S. PATENT DOCUMENTS

| | | |
|---|---|---|
| 2011/0142789 A1 | 6/2011 | Gitler et al. |
| 2013/0130378 A1 | 5/2013 | Manoharan et al. |
| 2013/0172399 A1 | 7/2013 | Corey et al. |
| 2013/0225659 A1 | 8/2013 | Bennett |
| 2014/0107330 A1 | 4/2014 | Freier et al. |
| 2014/0303238 A1 | 10/2014 | Linsley et al. |
| 2015/0018540 A1 | 1/2015 | Prakash et al. |
| 2015/0141320 A1 | 5/2015 | Krieg et al. |
| 2015/0184153 A1 | 7/2015 | Freier et al. |
| 2015/0191727 A1 | 7/2015 | Migawa et al. |
| 2015/0259679 A1 | 9/2015 | Bennett et al. |
| 2015/0267195 A1 | 9/2015 | Seth et al. |
| 2015/0275212 A1 | 10/2015 | Albaek et al. |
| 2016/0053254 A1 | 2/2016 | De Kimpe et al. |
| 2017/0175114 A1 | 6/2017 | Freier et al. |

FOREIGN PATENT DOCUMENTS

| | | |
|---|---|---|
| EA | 011389 B1 | 2/2007 |
| EP | 0878543 A1 | 11/1998 |
| EP | 1752536 A1 | 2/2007 |
| EP | 2399611 A2 | 12/2011 |
| WO | WO-1997/042314 A1 | 11/1997 |
| WO | WO-2004/003201 A2 | 1/2004 |
| WO | WO-2004/047872 A2 | 6/2004 |
| WO | WO-2004/070062 A2 | 8/2004 |
| WO | WO-2005/116204 A1 | 12/2005 |
| WO | WO-2005/116212 A2 | 12/2005 |
| WO | WO-2006/021814 | 3/2006 |
| WO | WO-2006/131925 A2 | 12/2006 |
| WO | WO-2008/109379 A1 | 9/2008 |
| WO | WO-2008/109450 A2 | 9/2008 |
| WO | WO-2008/152636 A2 | 12/2008 |
| WO | WO-2009/046141 | 4/2009 |
| WO | WO-2010/014592 A1 | 2/2010 |
| WO | WO-2011/006121 A2 | 1/2011 |
| WO | WO-2011/097641 A1 | 8/2011 |
| WO | WO-2012/012467 A2 | 1/2012 |
| WO | WO-2012/079578 A1 | 6/2012 |
| WO | WO-2012/149438 | 11/2012 |
| WO | WO-2013/081864 A1 | 6/2013 |
| WO | WO-2013/162363 A1 | 10/2013 |
| WO | WO-2013/173645 A1 | 11/2013 |
| WO | WO-2015/002971 A2 | 1/2015 |
| WO | WO-2015/072438 A1 | 5/2015 |
| WO | WO-2015/143245 A1 | 9/2015 |
| WO | WO-2015/143246 A1 | 9/2015 |
| WO | WO-2017/117496 A1 | 7/2017 |

OTHER PUBLICATIONS

Branch et al., A good antisense molecule is hard to find. TIES. 1998; 23:45-50.

Burke et al., Huntingtin and DRPLA proteins selectively interact with the enzyme GAPDH. Nat Med. 1996; 2(3):347-50.

Chin, On the Preparation and Utilization of Isolated and Purified Oligonucleotides. Document purportedly located on a CD-ROM and contributed to the public collection of the Katherine R. Everett Law Library of the University of North Carolina on Mar. 14, 2002.

Ciosk et al., ATX-2, the C. elegans ortholog of ataxin 2, functions in translational regulation in the germline. Development. 2004; 131(19):4831-41.

Corrado et al., ATXN-2 CAG repeat expansions are interrupted in ALS patients. Hum Genet. 2011; 130(4):575-80.

Crooke, S.T. et al., Antisense Drug Technolog. Second Edition, CRC Press (2008) Chapters 1-28.

Duvick et al., SCA1-like disease in mice expressing wild-type ataxin-1 with a serine to aspartic acid replacement at residue 776. Neuron. 2010; 67(6): 929-35.

Egli, et al., Synthesis, improved antisense activity and structural rationale for the divergent RNA affinities of 3'-fluoro hexitol nucleic acid (FHNA and Ara-FHNA) modified oligonucleotides. J Am Chem. 2011; 133(41):16642-9.

Elden et al., Ataxin-2 intermediate-length polyglutamine expansions are associated with increased risk for ALS. Nature. 2010; 466:1069-75.

Evers et al., Targeting Several CAG Expansion Diseases by a Single Antisense Oligonucleotide. PLoS ONE. 2011; 6(9): e24308.

Gautschi et al., Activity of a Novel bcl-2/bcl-xL-Bispecific Antisense Oligonucleotide Against Tumors of Diverse Histologic Origins. J Natl Cancer Inst. 2001; 93:463-71.

GenBank: BX410018.2, BX410018 *Homo sapiens* Fetal Brain *Homo sapiens* cDNA clone CSODF030YBO7 5-PRIME, mRNA sequence; (2003) (retrieved from the internet Jun. 28, 2017: https://www.ncbi.nlm.nih.gov/nucest/BX410018.2).

GenBank: NM 002973.3, *Homo sapiens* Ataxin 2 (ATXN2), transcript variant 1, mRNA, NCBI Accession No. NM 002973 (2015) (retrieved from the internet Jun. 28, 2017: https://www.ncbi.nlm.nih.gov/nuccore/171543894/).

GenBank: NT 009775.17 (truncated from nucleotides 2465000 to 2616000) *Homo sapiens* chromosome 12 genomic contig, GRCh37.p13 Primary Assembly (2013) (retrieved from the internet Jun. 28, 2017: https://www.ncbi.nlm.nih.gov/nuccore/NT 009775.17?report—genbank).

Heuvel et al., Taking a risk: a therapeutic focus on ataxin-2 in amyotrophic lateral sclerosis? Trends Mol Med. 2014; 20(1):25-35.

Huynh et al., Expansion of the polyQ repeat in ataxin-2 alters its Golgi localization, disrupts the Golgi complex and causes cell death. Hum Mol Genet. 2003; 12:1485-96.

Huynh et al., Expression of ataxin-2 in brains from normal individuals and patients with Alzheimer's disease and spinocerebellar ataxia 2. Ann Neurol. 1999; 45:232-41.

Kim et al., Importance of low-range CAG expansion and CAA interruption in SCA2 Parkinsonism. Arch Neurol. 2007; 64(10):1510-8.

Koshy et al., Spinocerebellar ataxia type-1 and spinobulbar muscular atrophy gene products interact with glyceraldehyde-3-phosphate dehydrogenase. Hum Mol Genet. 1996; 5(9):1311-8.

Lajoie et al., Formation and toxicity of soluble polyglutamine oligomers in living cells. PLoS One. 2010; 5(12):e15245 (15 pages).

Lovett-Racke et al., Therapeutic Potential of Small Interfering RNA for Central Nervous System Diseases. Arch Neurobiol. 2005; 62:1810-3.

Maher et al., Comparative hybrid arrest by tandem antisense oligodeoxyribonucleotides or oligodeoxyribonucleoside methylphosphonates in a cell-free system. Nuc Acid Res. 1988; 16(8):3341-58.

Magaña J.J. et al., Spinocerebellar Ataxia Type 2: Clinical Presentation, Molecular Mechanisms, and Therapeutic Perspectives. Mol Neurobiol. 2013; 47:90-104.

New England Biolabs 1998/99 Catalog (cover page and pp. 121 and 284).

Nonhoff et al., Ataxin-2 interacts with the DEAD/H-box RNA helicase DDX6 and interferes with P-bodies and stress granules. Mol Biol Cell. 2007; 18(4):1385-96.

Nonis et al., Ataxin-2 associates with the endocytosis complex and affects EGF receptor trafficking. Cell Signal. 2008; 20(10):1725-39.

Pulst S.M. (ed.), Inherited Ataxias: An Introduction. Genetics of Movement Disorders. Elsevier, Inc., Amsterdam, published Oct. 3, 2002, pp. 19-34.

Pulst S.M., Rare mendelian diseases: pathways to therapy development. Oral presentation, American Academy of Neurology Annual Meeting, Philadelphia, PA, Apr. 29, 2014.

Ramachandran, P., RNA interference therapy for the Spinocerebellar ataxias. Thesis, May 2014, University of Iowa, pp. 1-140.

Reynolds et al., Rational siRNA design for RNA interference. Nat Biotechnol. 2004; 22(3):326-30.

Ross et al., Ataxin-2 repeat-length variation and neurodegeneration. Hum Mol Genet. 2011; 20(16):3207-12.

Sanghvi et al., Heterocyclic Base Modifications in Nucleic Acids and Their Applications in Antisense Oligonucleotides. Antisense Res Appl. 1993; pp. 273-288.

Satterfield et al., Ataxin-2 and its *Drosophila* homolog, ATX2, physically assemble with polyribosomes. Hum Mol Genet. 2006; 15(16):2523-32.

(56) References Cited

OTHER PUBLICATIONS

Scoles et al, Antisense oligonucleotides for the treatment of spinocerebellar ataxia type 2 (SCA2), 5th Ataxia Investigators Meeting (AIM) meeting abstract presented Mar. 20, 2014.
Scoles et al., Antisense oligonucleotides for the treatment of spinocerebellar ataxia type 2 (SCA2), AAN Annual Meeting abstract published online Feb. 26, 2015; Neurology (2015) 82(Meeting Abstracts): 532.002.
Scoles et al., ATXN2 is Regulated by a Promoter Associated Antisense Long Noncoding RNA (IncRNA). Neurology. 2013; 80:P05030 (2 pages).
Scoles et al., ETS1 regulates the expression of ATXN2. Human Mol Genet. 2012; 21(23):5048-65.
Scoles et al., Treatment of Spinocerebellar Ataxia Type 2 (SCA2) with MOE Antisense Oligonucleotides. AAN Annual Meeting abstract published online Feb. 26, 2014; Neurology 2014; 82(10 Supplement):547.006.
Seth et al., Short Antisense Oligonucleotides with Novel 2'-4' Conformationally Restricted Nucleoside Analogues Show Improved Potency Without Increased Toxicity in Animals. J Med Chem. 2009; 52:10-3.
Shen, L. et al., Characteristics of Spinocerebellar Ataxia Type 2 Gene Mutation Dictation in Hereditary Spinocerebellar Ataxia. Chin J Intern Med. 2000; 39(4):259-61 (Abstract provided).
Shibata et al., A novel protein with RNA-binding motifs interacts with ataxin-2. Hum Mol Genet. 2000; 9(9):1303-13.
Van Damme et al., Expanded ATXN2 CAG repeat size in ALS identifies genetic overlap between ALS and SCA2. Neurology. 2011; 76(24):2066-72.
Woolf et al., Specificity of antisense oligonucleotides in vivo. Proc Natl Acad Sci USA. 1992; 89:7305-9.
Yamanaka et al., Transcription factor sequestration by polyglutamine proteins. Methods Mol Biol. 2010; 648:215-29.
European Partial Search Report dated Oct. 25, 2017, by the European Patent Office for Patent Application No. 15765851.9, which was filed on Mar. 19, 2015 and published as EP 3119888 on Jan. 25, 2017 (Inventor—Bennett et al.; Applicant—Ionis Pharmaceuticals, Inc. et al., 14 pages.
Supplementary European Search Report and Written Opinion dated Jan. 30, 2018 by the European Patent Office for Patent Application No. 15765851.9, which was filed on Mar. 19, 2015 and published as EP 3119888 on Jan. 25, 2017 (Inventor—Bennett et al.; Applicant—Ionis Pharmaceuticals, Inc. et al.) (16 pages).
International Search Report and Written Opinion dated Jun. 29, 2015 by the International Searching Authority for Patent Application No. PCT/US2015/021607, which was filed on Mar. 19, 2015 and published as WO 2015/143245 on Sep. 24, 2015 (Inventor—Bennett et al.; Applicant—Ionis Pharmaceuticals, Inc. et al.; (9 pages).
International Preliminary Report on Patentability dated Sep. 20, 2016 by the International Searching Authority for Patent Application No. PCT/US2015/021607, which was filed on Mar. 19, 2015 and published as WO 2015/143245 on Sep. 24, 2015 (Inventor—Bennett et al.; Applicant—Ionis Pharmaceuticals, Inc. et al.; (5 pages).
International Search Report dated Jul. 1, 2015 by the International Searching Authority for Patent Application No. PCT/US2015/021608, which was filed on Mar. 19, 2015 and published as WO 2015/143246 on Sep. 24, 2015 (8 pages).
International Preliminary Report on Patentability dated Sep. 20, 2016 by the International Searching Authority for Patent Application No. PCT/US2015/021608, which was filed on Mar. 19, 2015 and published as WO 2015/143246 on Sep. 24, 2015 (Inventor—Freier et al.; Applicant—Ionis Pharmaceuticals, Inc. et al.) (5 pages).
International Search Report mailed on by the International Searching Authority for Patent Application No. PCT/US2016/069406, which was filed on Dec. 30, 2016 and published as WO 2017/117496 on Jul. 6, 2017 (12 pages).
International Preliminary Report on Patentability dated Jul. 3, 2018 by the International Searching Authority for Patent Application No. PCT/US2016/069406, which was filed on Dec. 30, 2016 and published as WO 2017/117496 on Jul. 6, 2017 (Inventor—Frank Rigo.; Applicant—Ionis Pharmaceuticals, Inc. et al.) (8 pages).
Wikipedia, Ataxin-2. May 16, 2018. Retrieved from the Internet Jul. 16, 2018. <URL: http://en.wikipedia.org/wiki/Ataxin-2> (7 pages).
Florida Hospital. Lou Gehrig's Disease (ALS): Prevention. Retrieved from the Internet Jul. 16, 2018 <URL: https://www.floridahospital.com/lou-gehrigs-disease-als/prevention-lou-gehrigs-disease-als> (4 pages).
Mayo Clinic, Parkinson's Disease—Symptoms and Causes. Retrieved from the Internet Jul. 16, 2018 <URL: https://www.mayoclinic.org/diseases-conditions/parkinsons-disease/symptoms-causes/syc-20376055> (7 pages).
U.S. Appl. No. 61/955,704, filed Mar. 19, 2014, C. Frank Bennett (Ionis Pharmaceuticals, Inc. et al.).
U.S. Appl. No. 61/982,124, filed Apr. 21, 2014, C. Frank Bennett (Isis Pharmaceuticals, Inc. et al.).
U.S. Appl. No. 15,127,352, filed Sep. 19, 2016, C. Frank Bennett, U.S. Appl. No. 10/006,027, filed Jun. 26, 2018, Ionis Pharmaceuticals, Inc. et al.).
PCT/US2015/021607 (WO 2015/143245), filed Mar. 19, 2015 (Sep. 24, 2015), C. Frank Bennett (Ionis Pharmaceuticals, Inc. et al.).
PCT/US2015/021608 (WO 2015/143246), filed Mar. 19, 2015 (Sep. 24, 2015), Susan M. Freier (Ionis Pharmaceuticals, Inc. et al.).
PCT/US2016/069406 (WO 2017/117496), filed Dec. 30, 2016 (Jul. 6, 2017), Frank Rigo (Ionis Pharmaceuticals, Inc.).

METHODS FOR MODULATING ATAXIN 2 EXPRESSION

This application is a continuation of U.S. patent application Ser. No. 15/127,352, now U.S. Pat. No. 10,006,027, filed Sep. 19, 2016, which is a National Phase Application of International Application No. PCT/US2015/021607 filed Mar. 19, 2015, which claims the benefit of priority to U.S. Provisional Application 61/982,124, filed on Apr. 21, 2014 and U.S. Provisional Application 61/955,704, filed on Mar. 19, 2014, each of which is incorporated herein in its entirety by this reference.

STATEMENT OF GOVERNMENT SUPPORT

This invention was made with government support under R21 NS081182 awarded by the National Institutes of Health. The government has certain rights in the invention.

SEQUENCE LISTING

The present application is being filed along with a Sequence Listing in electronic format. The Sequence Listing is provided as a file entitled BIOL0242USASEQ_ST25.txt created Sep. 12, 2016, which is 232 Kb in size. The information in the electronic format of the sequence listing is incorporated herein by reference in its entirety.

FIELD

Provided are methods for reducing expression of Ataxin 2 (ATXN2) mRNA and protein in an animal. Such methods are useful to treat, prevent, or ameliorate neurodegenerative diseases, including spinocerebellar ataxia type 2 (SCA2), amyotrophic lateral sclerosis (ALS), and parkinsonism by inhibiting expression of Ataxin 2 in an animal.

BACKGROUND

Spinocerebellar ataxia type 2 (SCA2) is an autosomal dominant neurodegenerative disease characterized by progressive functional and cell loss of neurons in the cerebellum, brain stem and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935) and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., *Development,* 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein CIN85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating such neurodegenerative diseases. It is therefore an object herein to provide methods for the treatment of such diseases.

SUMMARY

Provided herein are methods for modulating expression of Ataxin 2 (ATXN2) mRNA and protein. In certain embodiments, compounds useful for modulating expression of Ataxin 2 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, Ataxin 2 mRNA levels are reduced. In certain embodiments, Ataxin 2 protein levels are reduced. Such reduction can occur in a time-dependent manner or in a dose-dependent manner.

Also provided are methods useful for preventing, treating, and ameliorating diseases, disorders, and conditions. In certain embodiments, such Ataxin 2 related diseases, disorders, and conditions are neurodegenerative diseases. In certain embodiments, such neurodegenerative diseases, disorders, and conditions include spinocerebellar ataxia type 2 (SCA2), amyotrophic lateral sclerosis (ALS), and parkinsonism.

Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: ataxia, speech and swallowing difficulties, rigidity, tremors, ophthalmoplegia, saccadic slowing, peripheral neuropathy, atrophy, dystonia, chorea, and dementia.

In certain embodiments, methods of treatment include administering an Ataxin 2 antisense compound to an individual in need thereof. In certain embodiments, methods of treatment include administering an Ataxin 2 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxyethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Ataxin 2", it is implied that the Ataxin 2 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Ataxin 2" means the mammalian gene Ataxin 2 (ATXN2), including the human gene Ataxin 2 (ATXN2). Human Ataxin 2 has been mapped to human chromosome 12q24.1.

"Ataxin 2 associated disease" means any disease associated with any Ataxin 2 nucleic acid or expression product thereof. Such diseases may include a neurodegenerative disease. Such neurodegenerative diseases may include spinocerebellar ataxia type 2 (SCA2), amyotrophic lateral sclerosis (ALS), and parkinsonism.

"Ataxin 2 mRNA" means any messenger RNA expression product of a DNA sequence encoding Ataxin 2.

"Ataxin 2 nucleic acid" means any nucleic acid encoding Ataxin 2. For example, in certain embodiments, an Ataxin 2 nucleic acid includes a DNA sequence encoding Ataxin 2, an RNA sequence transcribed from DNA encoding Ataxin 2

(including genomic DNA comprising introns and exons), and an mRNA sequence encoding Ataxin 2. "Ataxin 2 mRNA" means an mRNA encoding an Ataxin 2 protein.

"Ataxin 2 protein" means the polypeptide expression product of an Ataxin 2 nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having an Ataxin 2 associated disease" means identifying an animal having been diagnosed with an Ataxin 2 associated disease or predisposed to develop an Ataxin 2 associated disease. Individuals predisposed to develop an Ataxin 2 associated disease include those having one or more risk factors for developing an Ataxin 2 associated disease, including, growing older, having a personal or family history, or genetic predisposition of one or more Ataxin 2 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Ataxin 2" means reducing the level or expression of an Ataxin 2 mRNA and/or protein. In certain embodiments, Ataxin 2 mRNA and/or protein levels are inhibited in the presence of an antisense compound targeting Ataxin 2, including an antisense oligonucleotide targeting Ataxin 2, as compared to expression of Ataxin 2 mRNA and/or protein levels in the absence of an Ataxin 2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

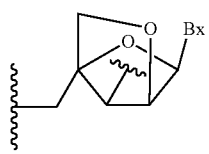

(A)

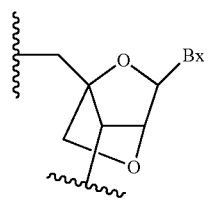

(B)

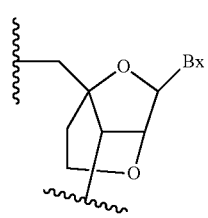

(C)

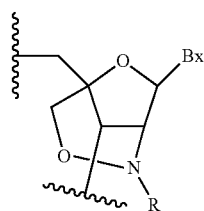

(D)

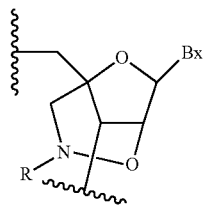

(E)

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Ataxin 2 is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods for inhibiting Ataxin 2 mRNA and protein expression. Certain embodiments provide methods, compounds, and composition for decreasing Ataxin 2 mRNA and protein levels.

Certain embodiments provide antisense compounds targeted to an Ataxin 2 nucleic acid. In certain embodiments, the Ataxin 2 nucleic acid is the sequence set forth in GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

Certain embodiments provide methods for the treatment, prevention, or amelioration of diseases, disorders, and conditions associated with Ataxin 2 in an individual in need thereof. Also contemplated are methods for the preparation of a medicament for the treatment, prevention, or amelioration of a disease, disorder, or condition associated with Ataxin 2. Ataxin 2 associated diseases, disorders, and conditions include neurodegenerative diseases. In certain embodiments, Ataxin 2 associated diseases include spinocerebellar ataxia type 2 (SCA2), amyotrophic lateral sclerosis (ALS), and parkinsonism.

Certain embodiments provide methods comprising administering an Ataxin 2 antisense compound to an animal for treating an Ataxin 2 associated disease.

Certain embodiments provide methods comprising identifying an animal having an Ataxin 2 associated disease; and administering an Ataxin 2 antisense compound.

In certain embodiments, the Ataxin 2 associated disease is a neurodegenerative disease.

In certain embodiments, the Ataxin 2 associated disease is spinocerebellar ataxia type 2 (SCA2), amyotrophic lateral sclerosis (ALS), or parkinsonism.

In certain embodiments, the animal is a human.

In certain embodiments, the administering is parenteral administration.

In certain embodiments, the parenteral administration is any of intrathecal administration or intracerebroventricular administration.

In certain embodiments, the administering distributes the antisense compound to the Purkinje cells.

In certain embodiments, the administering improves rotarod performance.

In certain embodiments, rotarod performance is improved by 10 percent, 15 percent, or 20 percent.

In certain embodiments, the administering improves motor function.

In certain embodiments, at least one symptom of an Ataxin 2 associated disease is ameliorated, treated, prevented, or slowed.

In certain embodiments, the antisense compound is a modified oligonucleotide.

In certain embodiments, the modified oligonucleotide has the nucleobase sequence of SEQ ID NO: 15, 20, 26, 36, 43, 81, 103, or 109.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an Ataxin 2 nucleic acid is 12 to 30 subunits in length. In certain embodiments, an antisense compound targeted to an Ataxin 2 nucleic acid is 12 to 25 subunits in length. In certain embodiments, an antisense compound targeted to an Ataxin 2 nucleic acid is 12 to 22 subunits in length. In certain embodiments, an antisense compound targeted to an Ataxin 2 nucleic acid is 14 to 20 subunits in length. In certain embodiments, an antisense compound targeted to an Ataxin 2 nucleic acid is 15 to 25 subunits in length. In certain embodiments, an antisense compound targeted to an Ataxin 2 nucleic acid is 18 to 22 subunits in length. In certain embodiments, an antisense compound targeted to an Ataxin 2 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to an Ataxin 2 nucleic acid is 12 subunits in length. In certain embodiments, an antisense compound targeted to an Ataxin 2 nucleic acid is 13 subunits in length. In certain embodiments, an antisense compound targeted to an Ataxin 2 nucleic acid is 14 subunits in length. In certain embodiments, an antisense compound targeted to an Ataxin 2 nucleic acid is 15 subunits in length. In certain embodiments, an antisense compound targeted to an Ataxin 2 nucleic acid is 16 subunits in length. In certain embodiments, an antisense compound targeted to an Ataxin 2 nucleic acid is 17 subunits in length. In certain embodiments, an antisense compound targeted to an Ataxin 2 nucleic acid is 18 subunits in length. In certain embodiments, an antisense compound targeted to an Ataxin 2 nucleic acid is 19 subunits in length. In certain embodiments, an antisense compound targeted to an Ataxin 2 nucleic acid is 20 subunits in length. In certain embodiments, an antisense compound targeted to an Ataxin 2 nucleic acid is 21 subunits in length. In certain embodiments, an antisense compound targeted to an Ataxin 2 nucleic acid is 22 subunits in length. In certain embodiments, an antisense compound targeted to an Ataxin 2 nucleic acid is 23 subunits in length. In certain embodiments, an antisense compound targeted to an Ataxin 2 nucleic acid is 24 subunits in length. In certain embodiments, an antisense compound targeted to an Ataxin 2 nucleic acid is 25 subunits in length. In certain embodiments, an antisense compound targeted to an Ataxin 2 nucleic acid is 26 subunits in length. In certain embodiments, an antisense compound targeted to an Ataxin 2 nucleic acid is 27 subunits in length. In certain embodiments, an antisense compound targeted to an Ataxin 2 nucleic acid is 28 subunits in length. In certain embodiments, an antisense compound targeted to an Ataxin 2 nucleic acid is 29 subunits in length. In certain embodiments, an antisense compound targeted to an Ataxin 2 nucleic acid is 30 subunits in length. In certain embodiments, the antisense compound targeted to an Ataxin 2 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to an Ataxin 2 nucleic acid may be shortened or truncated. For example, a single subunit may be deleted from the 5' end (5' truncation), or alternatively from the 3' end (3' truncation). A shortened or truncated antisense compound targeted to an Ataxin 2 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an Ataxin 2 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Ataxin 2 include, without limitation, the following: GENBANK Accession No. NM_002973.3 (incorporated herein as SEQ ID NO: 1), the complement of GENBANK Accession No. NT_009775.17 truncated from nucleotides 2465000 to 2616000 (incorporated herein as SEQ ID NO: 2) and GENBANK Accession No. BX410018.2 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Ataxin 2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Ataxin 2 mRNA levels are indicative of inhibition of Ataxin 2 expression. Reductions in levels of an Ataxin 2 protein are also indicative of inhibition of target mRNA expression. Phenotypic changes are indicative of inhibition of Ataxin 2 expression. Improvement in neurological function is indicative of inhibition of Ataxin 2 expression. Improved motor function and memory are indicative of inhibition of Ataxin 2 expression.

Hybridization

In some embodiments, hybridization occurs between an antisense compound disclosed herein and an Ataxin 2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an Ataxin 2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an Ataxin 2 nucleic acid).

Non-complementary nucleobases between an antisense compound and an Ataxin 2 nucleic acid may be tolerated provided that the antisense compound remains able to specifically hybridize to a target nucleic acid. Moreover, an antisense compound may hybridize over one or more segments of an Ataxin 2 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an Ataxin 2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an Ataxin 2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an Ataxin 2 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an Ataxin 2 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The nonidentical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar.

Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an Ataxin 2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C($R_1$)($R_2$) (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'—OCH$_2$CH$_3$, 2'—OCH$_2$CH$_2$F and 2'-O(CH$_2$)$_2$OCH$_3$ substituent groups. The substituent at the 2' position can also be selected from allyl, amino, azido, thio, O—$C_1$-$C_{10}$ alkyl, OCF$_3$, OCH$_2$F, O(CH$_2$)$_2$SCH$_3$, O(CH$_2$)$_2$—O—N($R_m$)($R_n$), O—CH$_2$—C(=O)—N($R_m$)($R_n$), and O—CH$_2$—C(=O)—N($R_1$)—(CH$_2$)$_2$—N($R_m$)($R_n$), where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); wherein R is H, $C_1$-$C_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U S. A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Pat. Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the a-L configuration or in the 13-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

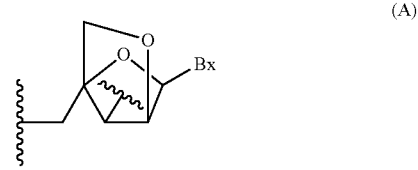

(A)

-continued (B) 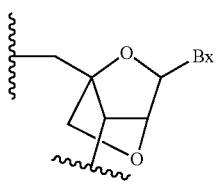

(C) 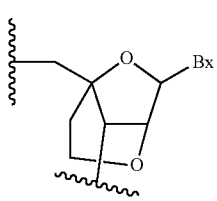

(D) 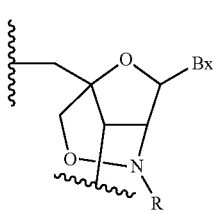

(E) 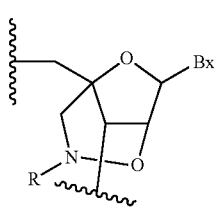

(F) 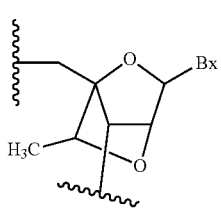

(G) 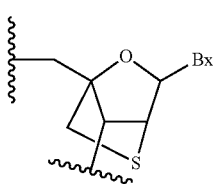

(H) 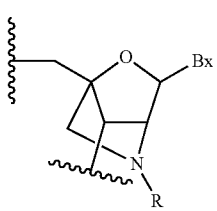

(I) 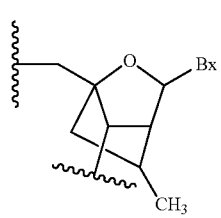

-continued (J) 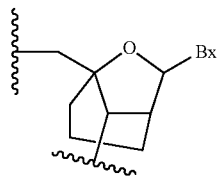

wherein Bx is the base moiety and R is independently H, a protecting group or $C_1$-$C_{12}$ alkyl.

In certain embodiments, bicyclic nucleosides are provided having Formula I:

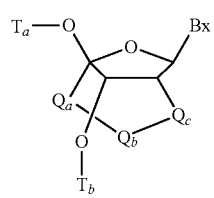

I wherein:
Bx is a heterocyclic base moiety;
-$Q_a$-$Q_b$-$Q_c$- is —$CH_2$—$N(R_c)$—$CH_2$—, —$C(=O)$—$N(R_c)$—$CH_2$—, —$CH_2$—$O$—$N(R_c)$—, —$CH_2$—$N(R_c)$—$O$— or —$N(R_c)$—$O$—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

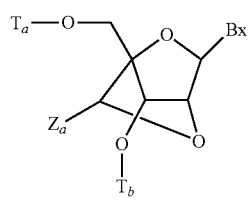

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

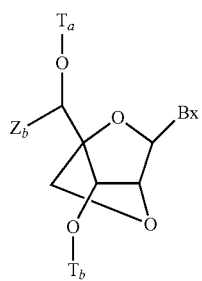

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

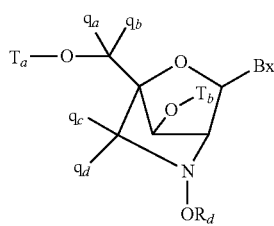

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

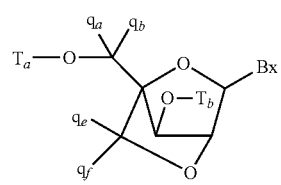

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

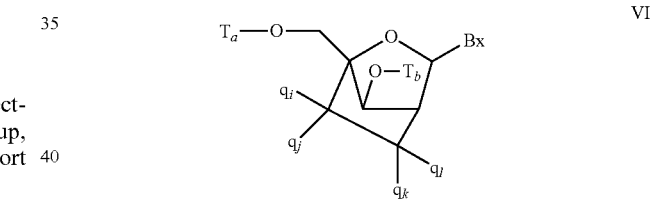

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

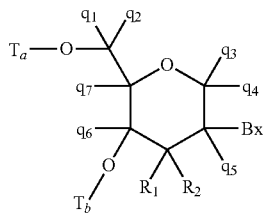

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an Ataxin 2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an Ataxin 2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Ataxin 2 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of an Ataxin 2 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an Ataxin 2 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Ataxin 2 nucleic acids can be assessed by measuring Ataxin 2 protein levels. Protein levels of Ataxin 2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Ataxin 2 and produce phenotypic changes, such as, improved motor function and cognition. In certain embodiments, motor function is measured by walking initiation analysis, rotarod, grip strength, pole climb, open field performance, balance beam, hindpaw footprint testing in the animal.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Ataxin 2 nucleic acid expression are measured.

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, spinocerebellar ataxia type 2 (SCA2), amyotrophic lateral sclerosis (ALS), and parkinsonism. In certain embodiments, the individual has been identified as having an Ataxin 2 associated disease. In certain embodiments, provided herein are methods for prophylactically reducing Ataxin 2 expression in an individual. Certain embodiments include treating an individual in need thereof by administering to an individual a therapeutically effective amount of an antisense compound targeted to an Ataxin 2 nucleic acid.

In one embodiment, administration of a therapeutically effective amount of an antisense compound targeted to an Ataxin 2 nucleic acid is accompanied by monitoring of Ataxin 2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to an Ataxin 2 nucleic acid results in reduction of Ataxin 2 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to an Ataxin 2 nucleic acid results in improved motor function in an animal. In certain embodiments, administration of an Ataxin 2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Ataxin 2 are used for the preparation of a medicament for treating a patient suffering or susceptible to a neurodegenerative disease including spinocerebellar ataxia type 2 (SCA2), amyotrophic lateral sclerosis (ALS), and parkinsonism.

EXAMPLES

Non-limiting Disclosure and Incorporation by Reference

While certain methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Ataxin 2 in HepG2 Cells by MOE Gapmers

Antisense oligonucleotides were designed targeting an ataxin 2 nucleic acid and were tested for their effects on ataxin 2 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 4,500 nM antisense oligonucleotide. After a treatment period of approximately 24 hours, RNA was isolated from the cells and ataxin 2 mRNA levels were measured by quantitative real-time PCR. Human primer probe set RTS3642 (forward sequence ACCAAAGAGTAGTTAATGGAGGTGTTC, designated herein as SEQ ID NO: 5; reverse sequence AGAAGGTGGGCGAGAGGAA, designated herein as SEQ ID NO: 6; probe sequence CTGGCCATCGCCTTGCCCA, designated herein as SEQ ID NO: 7) was used to measure mRNA levels. Ataxin 2 mRNA levels were adjusted according to total RNA content, as measured by RIBOGREEN®. Results are presented as percent inhibition of ataxin 2, relative to untreated control cells.

The chimeric antisense oligonucleotides in the Tables below were designed as 5-10-5 MOE gapmers. The gapmers are 20 nucleosides in length, wherein the central gap segment is comprised often 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ataxin 2 mRNA, designated herein as SEQ ID NO: 1 (GENBANK Accession No. NM_002973.3) or the human ataxin 2 genomic sequence, designated herein as SEQ ID NO: 2 (the complement of GENBANK Accession No. NT_009775.17 truncated from nucleotides 2465000 to 2616000). Some oligonucleotides do not target either SEQ ID NO: 1 or SEQ ID NO: 2, but instead target a variant gene sequence, SEQ ID NO: 3 (GENBANK Accession No. BX410018.2). 'n/a' indicates that the antisense oligonucleotide does not target that particular gene sequence with 100% complementarity.

TABLE 1

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564118 | 606 | 625 | CCGGCTCGCACGCCGGGCGG | 57 | 2596 | 2615 | 11 |
| 564119 | 612 | 631 | CATACACCGGCTCGCACGCC | 63 | 2602 | 2621 | 12 |
| 564120 | 637 | 656 | GGCTTCAGCGACATGGTGAG | 78 | 2627 | 2646 | 13 |
| 564121 | 880 | 899 | CGACCTCTGCCCAGGCCGGG | 67 | n/a | n/a | 14 |
| 564122 | 935 | 954 | TGCATAGATTCCATCAAAAG | 90 | 47454 | 47473 | 15 |
| 564123 | 959 | 978 | AAGTATATGAACCATCCTCA | 67 | 47478 | 47497 | 16 |
| 564124 | 997 | 1016 | TTCACTTGTACTTCACATTT | 85 | 48696 | 48715 | 17 |
| 564125 | 1084 | 1103 | TCTGTACTTTTCTCATGTGC | 88 | 49258 | 49277 | 18 |
| 564126 | 1090 | 1109 | CTGGATTCTGTACTTTTCTC | 89 | 49264 | 49283 | 19 |
| 564127 | 1123 | 1142 | CTCTCCATTATTTCTTCACG | 92 | 49297 | 49316 | 20 |
| 564128 | 1168 | 1187 | TCTTTAAACTGTACCACAAC | 86 | 49342 | 49361 | 21 |
| 564129 | 1210 | 1229 | GAGTCAGTAAAAGCATCTCT | 84 | n/a | n/a | 22 |
| 564130 | 1264 | 1283 | CAGGGCTCCAGGTCCTTCTC | 83 | 76401 | 76420 | 23 |
| 564131 | 1270 | 1289 | GCATCCCAGGGCTCCAGGTC | 86 | 76407 | 76426 | 24 |
| 564132 | 1363 | 1382 | TCTTCATTATATCGAAACAT | 84 | 80718 | 80737 | 25 |
| 564133 | 1477 | 1496 | GCTAACTGGTTTGCCCTTGC | 98 | 81637 | 81656 | 26 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564134 | 1556 | 1575 | GTATTTTCTTCCTCACTCC | 82 | 81716 | 81735 | 27 |
| 564135 | 1562 | 1581 | TGCTGTGTATTTTTCTTCCT | 89 | 81722 | 81741 | 28 |
| 564136 | 1748 | 1767 | GAAATCTGAAGTGTGAGAAG | 61 | 83359 | 83378 | 29 |
| 564137 | 1789 | 1808 | CCTCCATTAACTACTCTTTG | 90 | 83400 | 83419 | 30 |
| 564138 | 1795 | 1814 | GGAACACCTCCATTAACTAC | 66 | n/a | n/a | 31 |
| 564139 | 1807 | 1826 | GGCGATGGCCAGGGAACACC | 95 | 85303 | 85322 | 32 |
| 564140 | 1844 | 1863 | GTAGCGAGAAGGTGGGCGAG | 88 | 85340 | 85359 | 33 |
| 564141 | 1862 | 1881 | AGAGTTGGGACCTGACTGGT | 84 | 85358 | 85377 | 34 |
| 564142 | 1868 | 1887 | TGGAAGAGAGTTGGGACCTG | 84 | 85364 | 85383 | 35 |
| 564143 | 1963 | 1982 | GGAGCTGGAGAACCATGAGC | 91 | 85459 | 85478 | 36 |
| 564144 | 1969 | 1988 | GAGACAGGAGCTGGAGAACC | 86 | 85465 | 85484 | 37 |
| 564145 | 2101 | 2120 | TTGTGGGATACAAATTCTAG | 56 | 88211 | 88230 | 38 |
| 564146 | 2185 | 2204 | GGAACCCCACTGACCACTGA | 70 | n/a | n/a | 39 |
| 564147 | 2401 | 2420 | TCTTGAAGCCTGGAATCTTT | 61 | 91671 | 91690 | 40 |
| 564148 | 2560 | 2579 | AACCTAAAATCATTCTTAAA | 21 | n/a | n/a | 41 |
| 564149 | 2596 | 2615 | AGTTGATCCATAGATTCAGA | 74 | 112905 | 112924 | 42 |
| 564150 | 2704 | 2723 | CTGGTACAGTTGCTGCTGCT | 91 | 113013 | 113032 | 43 |
| 564151 | 2710 | 2729 | CTGCCACTGGTACAGTTGCT | 85 | 113019 | 113038 | 44 |
| 564152 | 2899 | 2918 | TTTGCATTGGGATTCAATGT | 76 | 114859 | 114878 | 45 |
| 564153 | 2938 | 2957 | GAAGGCTTTGGCTGAGAGAA | 66 | n/a | n/a | 46 |
| 564154 | 2944 | 2963 | GTAGTAGAAGGCTTTGGCTG | 71 | n/a | n/a | 47 |
| 564155 | 2995 | 3014 | TGACCCACCATAGATGGGCT | 38 | 115850 | 115869 | 48 |
| 564156 | 3097 | 3116 | GGTATTGGGTATAAAGGTTG | 57 | n/a | n/a | 49 |
| 564157 | 3103 | 3122 | GTCATAGGTATTGGGTATAA | 76 | 116339 | 116358 | 50 |
| 564158 | 3331 | 3350 | GGATGCTGAGACTGATAATG | 54 | n/a | n/a | 51 |
| 564159 | 3337 | 3356 | ACATGAGGATGCTGAGACTG | 63 | n/a | n/a | 52 |
| 564160 | 3472 | 3491 | AATTTGGGACATGCATACAT | 23 | n/a | n/a | 53 |
| 564161 | 3490 | 3509 | GTCTCCTTGTTGTATGGTAA | 76 | 136963 | 136982 | 54 |
| 564162 | 3658 | 3677 | TGAACAGGACTGGGTGCAGG | 41 | 144433 | 144452 | 55 |
| 564163 | 3715 | 3734 | GACTGCTGCTGTGGACTGGC | 69 | 145447 | 145466 | 56 |
| 564164 | 3903 | 3922 | CTGACTGTACATGAGCCTGA | 50 | 147818 | 147837 | 57 |
| 564165 | 3909 | 3928 | CCATTCCTGACTGTACATGA | 69 | 147824 | 147843 | 58 |
| 564166 | 3927 | 3946 | CAGTTGGATGAGAAGGAACC | 58 | 147842 | 147861 | 59 |
| 564167 | 3933 | 3952 | CATGGGCAGTTGGATGAGAA | 29 | 147848 | 147867 | 60 |
| 564168 | 3971 | 3990 | ACCGCCGGGTGGCTGTGTCG | 40 | 147886 | 147905 | 61 |
| 564169 | 3993 | 4012 | TTTGAGCGAGGGCGGCCTGG | 19 | 147908 | 147927 | 62 |
| 564170 | 4005 | 4024 | GCTGTAGTGCACTTTGAGCG | 73 | 147920 | 147939 | 63 |

TABLE 1-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564171 | 4017 | 4036 | AGACTGGAATGGGCTGTAGT | 58 | 147932 | 147951 | 64 |
| 564172 | 4029 | 4048 | GCGCTGTTGTCGAGACTGGA | 74 | 147944 | 147963 | 65 |
| 564173 | 4035 | 4054 | GGAAATGCGCTGTTGTCGAG | 69 | 147950 | 147969 | 66 |
| 564174 | 4064 | 4083 | GGCTTGTACTGAAGGGTGCG | 23 | n/a | n/a | 67 |
| 564175 | 4070 | 4089 | GTGGTGGGCTTGTACTGAAG | 35 | n/a | n/a | 68 |
| 564176 | 4076 | 4095 | CTGTTGGTGGTGGGCTTGTA | 22 | 148827 | 148846 | 69 |
| 564177 | 4082 | 4101 | CAACTGCTGTTGGTGGTGGG | 39 | 148833 | 148852 | 70 |
| 564178 | 4088 | 4107 | GCCTTACAACTGCTGTTGGT | 62 | 148839 | 148858 | 71 |
| 564179 | 4106 | 4125 | TTCGGTTCCTCCAGGGCAGC | 72 | 148857 | 148876 | 72 |
| 564180 | 4166 | 4185 | TTCTAGTTTTCTGTGCTTCC | 72 | 148917 | 148936 | 73 |
| 564181 | 4367 | 4386 | AATAAATAACTTCCAGTTTC | 59 | 149118 | 149137 | 74 |
| 564182 | 4429 | 4448 | GAATCACTCTTGTTACTTCT | 78 | 149180 | 149199 | 75 |
| 564183 | 4435 | 4454 | CAGCAAGAATCACTCTTGTT | 85 | 149186 | 149205 | 76 |
| 564184 | 4551 | 4570 | TTTATAAATAATAATCCGTC | 4 | 149302 | 149321 | 77 |
| 564185 | 4593 | 4612 | AAGTTGAACCACTGTAGACA | 60 | 149344 | 149363 | 78 |
| 564186 | n/a | n/a | ATCGGCCACCACCCGCGCGC | 55 | 3683 | 3702 | 79 |
| 564187 | n/a | n/a | CAAAGGGTTAATTAGGATCT | 66 | 85057 | 85076 | 80 |
| 564188 | n/a | n/a | CCCAAAGGGTTAATTAGGAT | 94 | 85059 | 85078 | 81 |
| 564189 | n/a | n/a | AGGACAGTCATTTGATTTGT | 72 | 85166 | 85185 | 82 |
| 564190 | n/a | n/a | CTTTGAGGACAGTCATTTGA | 70 | 85171 | 85190 | 83 |
| 564191 | n/a | n/a | CTGACAGAACAAATGATATG | 17 | 85284 | 85303 | 84 |
| 564192 | n/a | n/a | TATTGGGTATAAAGGCTTGA | 31 | 116331 | 116350 | 85 |
| 564193 | n/a | n/a | GGTATTGGGTATAAAGGCTT | 78 | 116333 | 116352 | 86 |
| 564194 | n/a | n/a | CTCTTTTACGCATACAGGCA | 74 | 147789 | 147808 | 87 |
| 564195 | n/a | n/a | AGGAAGGCCAACTGAGTCCT | 70 | 148258 | 148277 | 88 |

TABLE 2

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564158 | 3331 | 3350 | GGATGCTGAGACTGATAATG | 61 | n/a | n/a | 51 |
| 564196 | 70 | 89 | GGTCAGACGGAAGCAGAACG | 9 | 2060 | 2079 | 89 |
| 564197 | 218 | 237 | CCACCTGGCTGCGGCGAAGC | 12 | 2208 | 2227 | 90 |
| 564198 | 392 | 411 | GCCGTTGCCGTTGCTACCAA | 80 | 2382 | 2401 | 91 |
| 564199 | 616 | 635 | GGCCCATACACCGGCTCGCA | 79 | 2606 | 2625 | 92 |
| 564200 | 636 | 655 | GCTTCAGCGACATGGTGAGG | 81 | 2626 | 2645 | 93 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564201 | 732 | 751 | GGACATTGGCAGCCGCGGGC | 83 | 2722 | 2741 | 94 |
| 564202 | 929 | 948 | GATTCCATCAAAAGAAATCG | 67 | n/a | n/a | 95 |
| 564203 | 969 | 988 | CAACTGATGTAAGTATATGA | 45 | 47488 | 47507 | 96 |
| 564204 | 1053 | 1072 | CCAAATCACACTTCGGACTG | 74 | n/a | n/a | 97 |
| 564205 | 1073 | 1092 | CTCATGTGCGGCATCAAGTA | 79 | 49247 | 49266 | 98 |
| 564206 | 1138 | 1157 | CATTTGAACAAAATACTCTC | 71 | 49312 | 49331 | 99 |
| 564207 | 1219 | 1238 | CTGATAGCAGAGTCAGTAAA | 72 | 76356 | 76375 | 100 |
| 564208 | 1521 | 1540 | GGGCCACTCGAGCTTTGTAC | 88 | 81681 | 81700 | 101 |
| 564209 | 1628 | 1647 | AGGAATATATTTATTTTCCC | 52 | 83239 | 83258 | 102 |
| 564210 | 1693 | 1712 | CCCATACGCGGTGAATTCTG | 91 | 83304 | 83323 | 103 |
| 564211 | 1713 | 1732 | TGGAGCCCGATCCAGGCTGG | 77 | 83324 | 83343 | 104 |
| 564212 | 1733 | 1752 | AGAAGTGGATCTTGATGGCA | 54 | 83344 | 83363 | 105 |
| 564213 | 1957 | 1976 | GGAGAACCATGAGCAGAGGG | 83 | 85453 | 85472 | 106 |
| 564214 | 2002 | 2021 | GGCCCTTCTGAAGACATGCG | 85 | n/a | n/a | 107 |
| 564215 | 2079 | 2098 | CACTGGATATGGAACCCCTC | 84 | 88189 | 88208 | 108 |
| 564216 | 2099 | 2118 | GTGGGATACAAATTCTAGGC | 94 | 88209 | 88228 | 109 |
| 564217 | 2177 | 2196 | ACTGACCACTGATGACCACG | 67 | 88287 | 88306 | 110 |
| 564218 | 2215 | 2234 | CTGGGTCTATGAGTTTTAGG | 67 | 91099 | 91118 | 111 |
| 564219 | 2291 | 2310 | TGGAATAATACCAGCTTGGG | 84 | 91175 | 91194 | 112 |
| 564220 | 2311 | 2330 | GGCATGGCAACAGCTTCAGT | 81 | 91195 | 91214 | 113 |
| 564221 | 2331 | 2350 | TAGGAGATGCAGCTGGAATA | 71 | 91215 | 91234 | 114 |
| 564222 | 2397 | 2416 | GAAGCCTGGAATCTTTAGCC | 69 | n/a | n/a | 115 |
| 564223 | 2426 | 2445 | CCCTGCAGGAGAGTTCTGCC | 75 | 91696 | 91715 | 116 |
| 564224 | 2582 | 2601 | TTCAGAAGTAGAACTTGGCT | 76 | 112891 | 112910 | 117 |
| 564225 | 2652 | 2671 | CAATTTGTCTTTGATCAAA | 56 | 112961 | 112980 | 118 |
| 564226 | 2757 | 2776 | TGTTACTAAGTATTGAAGGG | 53 | 113066 | 113085 | 119 |
| 564227 | 2787 | 2806 | AAGTGACCTCAGGTCCCCTC | 83 | 113096 | 113115 | 120 |
| 564228 | 2883 | 2902 | ATGTTGATTTCCTAACTTGC | 53 | 114843 | 114862 | 121 |
| 564229 | 3019 | 3038 | GTATAAACTGGAGTTGGCTG | 75 | 115874 | 115893 | 122 |
| 564230 | 3039 | 3058 | GTGCAAAACAAACAGGCTGA | 79 | 115894 | 115913 | 123 |
| 564231 | 3059 | 3078 | GACTGGATACATCATATTTG | 18 | 115914 | 115933 | 124 |
| 564232 | 3082 | 3101 | GGTTGCACGCCTGGGCTCAC | 74 | n/a | n/a | 125 |
| 564233 | 3102 | 3121 | TCATAGGTATTGGGTATAAA | 50 | 116338 | 116357 | 126 |
| 564234 | 3122 | 3141 | TTGATTCACTGGCATGGGCG | 77 | 116358 | 116377 | 127 |
| 564235 | 3180 | 3199 | GATGATGCTGGTCTTGCCGC | 49 | 130944 | 130963 | 128 |
| 564236 | 3373 | 3392 | ATCATTCTAGCATTACCCTG | 61 | 131454 | 131473 | 129 |
| 564237 | 3408 | 3427 | ATACTAAACCAGGCTGGGCG | 71 | 131489 | 131508 | 130 |

TABLE 2-continued

Inhibition of ataxin 2 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 564238 | 3464 | 3483 | ACATGCATACATCGCATGCG | 32 | n/a | n/a | 131 |
| 564239 | 3505 | 3524 | TAGAAAGAAGGGCTTGTCTC | 67 | 136978 | 136997 | 132 |
| 564240 | 3545 | 3564 | CGCATACTGCTGAGCAAGGG | 79 | 144320 | 144339 | 133 |
| 564241 | 3597 | 3616 | TAGCTGAAGGCTGAGGGTGT | 43 | 144372 | 144391 | 134 |
| 564242 | 3630 | 3649 | CACCATGTTGGCTTTGCTGC | 81 | 144405 | 144424 | 135 |
| 564243 | 3650 | 3669 | ACTGGGTGCAGGATGACTTC | 36 | 144425 | 144444 | 136 |
| 564244 | 3729 | 3748 | CGTGGTAAATGGCTGACTGC | 50 | 145461 | 145480 | 137 |
| 564245 | 3772 | 3791 | TTGGAGGCAGGTGTCATGGA | 36 | 145504 | 145523 | 138 |
| 564246 | 3938 | 3957 | TGGCGCATGGGCAGTTGGAT | 67 | 147853 | 147872 | 139 |
| 564247 | 3994 | 4013 | CTTTGAGCGAGGGCGGCCTG | 29 | 147909 | 147928 | 140 |
| 564248 | 4021 | 4040 | GTCGAGACTGGAATGGGCTG | 54 | 147936 | 147955 | 141 |
| 564249 | 4225 | 4244 | ATTCCTATTGGATGTTACAA | 65 | 148976 | 148995 | 142 |
| 564250 | 4252 | 4271 | ATCTTCCACTGCAAGTGAAC | 77 | 149003 | 149022 | 143 |
| 564251 | 4306 | 4325 | TATGGAATTATGGAATAGCC | 65 | 149057 | 149076 | 144 |
| 564252 | 4433 | 4452 | GCAAGAATCACTCTTGTTAC | 77 | 149184 | 149203 | 145 |
| 564253 | 4581 | 4600 | TGTAGACAGTGATCACCTCA | 77 | 149332 | 149351 | 146 |
| 564254 | n/a | n/a | GGCCAAGGCCCACTTGTCTC | 54 | 3485 | 3504 | 147 |
| 564255 | n/a | n/a | CACTGCGGCCTCGAACAGCA | 81 | 3709 | 3728 | 148 |
| 564263 | n/a | n/a | AAATTCCTCATTTTCTTTTC | 68 | 26924 27239 | 26943 27258 | 149 |
| 564264 | n/a | n/a | GTTATAGTAATCTGTAATCA | 71 | 36133 36239 | 36152 36258 | 150 |
| 564265 | n/a | n/a | AGGATTGTAAAATGATACAG | 47 | 65107 65148 | 65126 65167 | 151 |
| 564266 | n/a | n/a | GTAGGATTGTAAAATGATAC | 64 | 65109 65150 | 65128 65169 | 152 |
| 564267 | n/a | n/a | TTATATATGTAAATTATATC | 9 | 95228 95288 | 95247 95307 | 153 |
| 564268 | n/a | n/a | AACCACTGATTTATACACTT | 88 | 95260 95320 | 95279 95339 | 154 |
| 564269 | n/a | n/a | TTAAAACCACTGATTTATA | 17 | 95265 95325 | 95284 95344 | 155 |
| 564270 | n/a | n/a | ATATAGCACTCTGCTGTATT | 83 | 99282 99340 | 99301 99359 | 156 |
| 564271 | n/a | n/a | TACCAAGCTTGTGGCTTGGG | 32 | 137342 137420 | 137361 137439 | 157 |
| 564272 | n/a | n/a | TTATACCAAGCTTGTGGCTT | 52 | 137345 137423 | 137364 137442 | 158 |

TABLE 3

Inhibition of ataxin 2 mRNA by 5-10-5
MOE gapmers targeting SEQ ID NO: 3

| ISIS No | SEQ ID NO: 3 Start Site | SEQ ID NO: 3 Stop Site | Sequence | % inhibition | SEQ ID NO |
|---|---|---|---|---|---|
| 564256 | 311 | 330 | CCTCGATGTTCCACAGGCGC | 83 | 159 |
| 564257 | 715 | 734 | GAGTTCACCTGCATCCAGGG | 81 | 160 |
| 564258 | 736 | 755 | TCCAGTTCCCTCATTGGCTG | 27 | 161 |
| 564259 | 771 | 790 | GGTTCCATCCATTAGATACG | 52 | 162 |
| 564260 | 791 | 810 | TTAAACGAAACATATCTTTG | 10 | 163 |
| 564261 | 815 | 834 | GCCCCTGCGCCATAATTTTT | 3 | 164 |
| 564262 | 835 | 854 | ATAAACTGCTTTCAACGGTG | 2 | 165 |

Example 2: Dose-dependent Antisense Inhibition of Human Ataxin 2 in HepG2 Cells by MOE Gapmers Gapmers from Example 1 exhibiting significant in vitro inhibition of ataxin 2 mRNA were selected and tested at various doses in HepG2 cells. Cells were plated at a density of 20,000 cells per well and transfected using electroporation with 0.625 µM, 1.250 µM, 2.500 µM, 5.000 µM and 10.000 µM concentrations of antisense oligonucleotide, as specified in the Table below. After a treatment period of approximately 16 hours, RNA was isolated from the cells and ataxin 2 mRNA levels were measured by quantitative real-time PCR. Human primer probe set RTS3642 was used to measure mRNA levels. Ataxin 2 mRNA levels were adjusted according to total RNA content, as measured by RIBOGREEN®. Results are presented as percent inhibition of ataxin 2, relative to untreated control cells.

The half maximal inhibitory concentration ($IC_{50}$) of each oligonucleotide is also presented. Ataxin 2 mRNA levels were significantly reduced in a dose-dependent manner in antisense oligonucleotide treated cells.

TABLE 4

Dose response assay

| ISIS No | 0.625 µM | 1.250 µM | 2.500 µM | 5.000 µM | 10.000 µM | $IC_{50}$ (µM) |
|---|---|---|---|---|---|---|
| 564133 | 89 | 95 | 98 | 98 | 97 | <0.6 |
| 564188 | 52 | 72 | 81 | 88 | 90 | <0.6 |
| 564127 | 42 | 62 | 65 | 85 | 91 | 0.8 |
| 564150 | 39 | 63 | 74 | 86 | 91 | 0.8 |
| 564143 | 37 | 60 | 76 | 84 | 94 | 0.9 |
| 564122 | 25 | 53 | 69 | 85 | 88 | 1.3 |
| 564126 | 23 | 48 | 61 | 78 | 89 | 1.7 |
| 564144 | 12 | 35 | 53 | 71 | 85 | 2.4 |
| 564135 | 22 | 35 | 53 | 73 | 86 | 2.1 |
| 564125 | 33 | 44 | 64 | 78 | 85 | 1.5 |
| 564129 | 31 | 42 | 54 | 71 | 77 | 1.9 |
| 564216 | 50 | 67 | 82 | 86 | 94 | <0.6 |
| 564210 | 33 | 48 | 72 | 80 | 94 | 1.3 |
| 564208 | 30 | 40 | 67 | 75 | 87 | 1.6 |
| 564268 | 35 | 52 | 69 | 81 | 85 | 1.2 |

Example 3: Antisense Inhibition of Human Ataxin 2 in a SCA2 BAC Mouse Model

Gapmers from Example 1 exhibiting significant in vitro inhibition of ataxin 2 mRNA were selected and tested in vivo in a SCA2[Q22]-BAC mouse model. This mouse model was created in the Pulst laboratory (University of Utah, Salt Lake City), using mice of FVB/B6 hybrid background, for the study of spinocerebella ataxia type 2 (SCA2). These mice possess the entire 176 kb human ATXN2 gene region, including the 16 kb upstream sequence and the 2.5 kb downstream sequence.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 µL mark with either normal saline (0.9%) or antisense oligonucleotide (250 µg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 µL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 µL, consisting of 15 ng cDNA, 2 of each primer (0.3 µM final), and 10 µL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis.

The results from the RNA analysis for mouse and human ataxin 2 are presented in the Table below. As indicated, some of the ISIS oligonucleotides decreased human ataxin 2 mRNA in the brains of the mice.

TABLE 5

Percent inhibition of ataxin 2 mRNA compared to the saline (0.9%) control in SCA[Q22]-BAC mice

| ISIS No | Human ataxin 2 | Mouse ataxin 2 |
| --- | --- | --- |
| 564122 | 10 | 15 |
| 564127 | 46 | 65 |
| 564133 | 60 | 62 |
| 564150 | 21 | 53 |
| 564188 | 9 | 23 |
| 564216 | 21 | 55 |

Example 4: Antisense Inhibition of Human Ataxin 2 in an ATXN2-Q127 Mouse Model

Gapmers from Example 1 exhibiting significant in vitro inhibition of ataxin 2 mRNA were selected and tested in vivo in an ATXN2-Q127 mouse model. This mouse model (Hansen, S. T. et al., Human. Molecular Genetics 2012. 1-13) expresses the full-length-mutant $ATXN2^{Q127}$ complementary DNA under the regulation of the Purkinje cell protein-2 (Pcp2) promoter. This model shows an early-onset progressive motor impairment phenotype accompanied by the formation of diffuse cytoplasmic aggregates in cerebellar Purkinje cells.

Treatment

Groups of 3 mice each were administered normal saline (0.9%) or antisense oligonucleotide via intracerebroventricular injections. Five to seven week old mice were individually infused with a mixture of oxygen and 3% isoflurane for 3-4 minutes to cause sedation. The hair on the scalp was then removed with a shearing tool. The mouse was placed in a stereotaxic instrument (Stoelting Just for Mouse). The scalp was cleaned, first with an iodine scrub, and then with 70% ethanol. An incision was made with a #10 scalpel blade from the region just posterior to the place between the eyes to the region 1.5 cm behind. The periosteum was removed with a sterile cotton swab. A Hamilton syringe with a 26-gauge needle was placed in the needle holder of the stereotaxic instrument and filled up to the 10 µL mark with either normal saline (0.9%) or antisense oligonucleotide (250 µg) in saline (0.9%) solution. The needle was positioned on the bregma on the skull, and then positioned 1 mm to the right and 0.46 mm posterior. The tip of the needle was then inserted just through the skull and then positioned 2.5 mm down into the right lateral ventricle. The plunger of the syringe was then depressed to deliver the desired volume of 5-7 µL. After a wait of 4 minutes to allow ventricular pressure to equalize, the needle was removed and the scalp was sutured. The incision was then treated with povidone solution and the mouse returned to its cage on its back for recovery. The mice were monitored daily.

RNA Analysis

After 7 days, the mice were placed in isoflurane until they were no longer breathing. The brain was then extracted. Three portions of the brain were collected in coronal sections, including one 3 mm section for RNA analysis. RNA was isolated from 30 mg tissue using the RNeasy kit (Qiagen). cDNA was generated using the QuantiTect Reverse Transcription kit (Qiagen). Real-time PCR (qPCR) was conducted by the SYBR Green method with standard curves on the iCycler (Bio-Rad) in 96-well plates in quadruplicate. Reactions were of 20 µL, consisting of 15 ng cDNA, 2 µL of each primer (0.3 µM final), and 10 µL SYBR Green Master Mix (Bio-Rad). Cycling parameters included a 95° denaturation step for 10 seconds, incubation at the annealing temperature for 20 seconds, and a second incubation for 40 seconds at 72°. Each plate included a standard curve using cerebellar RNA prepared from multiple pGL2-5A3 transgenic mice. Single amplicons were verified by denaturation analysis and gel electrophoresis. All mRNA levels were normalized to the housekeeping gene, actin.

The results from the RNA analysis for mouse and human ataxin 2 are presented in the Table below. As indicated, some of the ISIS oligonucleotides decreased human ataxin 2 mRNA in the brains of the mice.

qPCR analysis of the marker for microgliosis, AIF/Iba1, to measure inflammation, was also performed. The results are presented in the Table below.

TABLE 6

Percent inhibition of ataxin 2 mRNA compared to the saline (0.9%) control in ATXN2-Q127 mice

| ISIS No | Human | Mouse |
| --- | --- | --- |
| 564133 | 64 | 52 |
| 564127 | 62 | 49 |
| 564216 | 46 | 40 |
| 564210 | 39 | 48 |

TABLE 7

Percent Iba1 mRNA level increase compared to the saline (0.9%) control in ATXN2-Q127 mice

| ISIS No | Iba1 |
| --- | --- |
| 564133 | 9 |
| 564127 | 49 |
| 564216 | 16 |
| 564210 | 96 |

Example 4: Dose-dependent Antisense Inhibition of Human Ataxin 2 in an ATXN2-Q127 Mouse Model ISIS 564133 was tested in different doses in the ATXN2-Q127 mouse model.

Treatment

Groups of 3 mice each were administered normal saline (0.9%) or ISIS 564133 via intracerebroventricular injections dosed at 50 µg, 100 µg, 200 µg, 250 µg, or 300 µg. The mice were administered in the same manner as described in the studies above and monitored daily.

RNA Analysis

After 7 days, the mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for mouse and human ataxin 2 are presented in the Table below.

TABLE 8

Percent inhibition of ataxin 2 mRNA compared to the saline (0.9%) control in ATXN2-Q127 mice

| Dose (µg) | Human ataxin 2 | Mouse ataxin 2 |
|---|---|---|
| 50 | 60 | 47 |
| 100 | 84 | 35 |
| 200 | 85 | 67 |
| 250 | 79 | 62 |
| 300 | 73 | 41 |

Example 5: Time-dependent Antisense Inhibition of Human Ataxin 2 in an ATXN2-Q127 Mouse Model ISIS 564133 was administered and mRNA level reduction was tested in different time points in the ATXN2-Q127 mouse model.

Treatment

Groups of 3 mice each were administered normal saline (0.9%) or ISIS 564133 via intracerebroventricular injections dosed at 200 µg. The mice were administered in the same manner as described in the studies above and monitored daily.

RNA Analysis

After 9 days, 18 days, 27 days, and 84 days, groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin.

The results from the RNA analysis for human ataxin 2 are presented in the Table below. Western analysis of the corresponding protein samples was performed and confirmed the qPCR results.

TABLE 9

Ataxin 2 mRNA levels in ATXN2-Q127 mice

| Time Point | ATXN2 expression relative to actin |
|---|---|
| saline (0.9%) control | 8.4 |
| 9 days | 2.9 |
| 18 days | 0.9 |
| 27 days | 1.4 |
| 84 days | 2.7 |

Immunohistochemical staining of cerebellar Purkinje cells on day 7 was performed using rabbit anti-oligonucleotide antibody generated in-house. The results demonstrated that ISIS oligonucleotide localized in cerebellar Purkinje cells of ATXN-Q127 mice.

Example 6: Effect of Antisense Inhibition of Human Ataxin 2 in an ATXN2-Q127 Mouse Model ISIS oligonucleotide was administered in the ATXN2-Q127 mouse model and wild-type mice. On day 3, motor performance was evaluated using the rotarod test.

Groups of ATXN2-Q127 mice were administered normal saline (0.9%) or ISIS 564133 at 50 µg, 100 µg, or 200 µg via intracerebroventricular injections in the same manner as described in the studies above. Groups of wild-type mice were administered normal saline (0.9%) or ISIS oligonucleotide at 200 µg via intracerebroventricular injections dosed in the same manner as described in the studies above. Groups of ATXN2-Q127 mice were administered normal saline (0.9%) or ISIS 546127 or ISIS 564216 at 200 µg via intracerebroventricular injections dosed in the same manner as described in the studies above. After 6 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20%.

TABLE 10

Rotarod performance test in ATXN2-Q127 mice

| Strain of mice | Number of mice | Treatment | Latency to fall (seconds) |
|---|---|---|---|
| WT | 10 | saline (0.9%) control | 199 |
|  | 10 | ISIS 564133 (200 µg) | 189 |
| ATXN-Q127 | 8 | saline (0.9%) control | 127 |
|  | 15 | ISIS 564133 (50 µg) | 149 |
|  | 16 | ISIS 564133 (100 µg) | 141 |
|  | 9 | ISIS 564133 (200 µg) | 100 |
| ATXN-Q127 | 15 | saline (0.9%) control | 130 |
|  | 13 | ISIS 564127 (200 µg) | 150 |
|  | 15 | ISIS 564216 (200 µg) | 156 |

Example 7: Effect of Antisense Inhibition of Human Ataxin 2 in an ATXN2-Q127 Mouse Model ISIS oligonucleotide was administered in the ATXN2-Q127 mouse model and wild-type mice. Cerebellar expression of ataxin 2, as well as several Purkinje cell (PC) genes, was assessed.

Groups of ATXN2-Q127 mice were administered normal saline (0.9%) or ISIS 564133 at 200 µg via intracerebroventricular injections dosed in the same manner as described in the studies above. Groups of wild-type mice were administered normal saline (0.9%) or ISIS 564133 at 200 µg via intracerebroventricular injections dosed in the same manner as described in the studies above. After 5 weeks, the mice were euthanized and cerebellar expression of various gene mRNA levels was assessed.

RNA Analysis

Groups of mice were placed in isoflurane until they were no longer breathing. The brain was then extracted. Three portions of the brain were collected in coronal sections, including one 3 mm section for RNA analysis, as described above. All mRNA levels were normalized to the housekeeping gene, actin. RNA levels of human ataxin 2, murine ataxin 2, Pcp2, Calb1, Rgs8, and Fam107b were measured. Transcription changes in several of these PC-specific genes have been demonstrated to progressively decrease in models of SCA2 (Hansen, S. T. et al., Hum. Mol. Genet. 2013. 22: 271-283).

The results from the RNA analysis are presented in the Table below and demonstrate that treatment with ISIS oligonucleotides targeting ataxin 2 increased the expression levels of all the PC-specific genes compared to the transgenic control group.

TABLE 11

| PC-specific mRNA levels in ATXN2-Q127 mice | | | |
|---|---|---|---|
| | WT | ATXN-Q127 | |
| | saline (0.9%) control | saline (0.9%) control | ISIS 564133 (200 µg) |
| human ataxin 2 | 0.21 | 3.57 | 1.31 |
| murine ataxin 2 | 0.79 | 0.84 | 0.6 |
| Pcp2 | 0.77 | 0.36 | 0.48 |
| Rgs8 | 1.45 | 0.25 | 0.35 |
| Calb1 | 1.14 | 0.5 | 0.71 |
| Fam107b | 1.41 | 0.7 | 0.9 |

Example 8: Effect of Antisense Inhibition of Human Ataxin 2 in an ATXN2-Q127 Mouse Model ISIS oligonucleotide was administered in the ATXN2-Q127 mouse model and wild-type mice. Motor performance was evaluated using the rotarod test.

Groups of ATXN2-Q127 mice (7.5 weeks of age) were administered normal saline (0.9%) or ISIS 546127 or ISIS 564216 at 200 µg via intracerebroventricular injections dosed in the same manner as described in the studies above. After 5 weeks and 9 weeks, the mice were subjected to the rotarod test.

Rotarod Assay

The accelerating rotarod assay was performed on the Rotamex rotarod. Rotarod testing was conducted over five days. On the first day, mice are acclimated to the technician by handling the mice. On the second day mice are introduced to the rotarod in a 4 minutes paradigm including 2 minutes at a constant speed of 10 RPM, then 2 minutes at a speed ranging from 10 to 30 RPM. Testing on days 3-5 were identical, where mice are placed on the rotarod at a speed of 0 RPM, then the rotarod was accelerated to 40 RPM over 6 minutes. This is done twice per day and a mean value of "latency to fall" per day was recorded, in seconds. Latency to fall is defined as the amount of time before the animal falls from the rotarod. It is recorded automatically, when the mouse no longer interrupts infrared beams directed above the rotarod. The time to first passive rotation (when mice stop walking and hold on and revolve with the rod) is also automatically recorded, and generally reflects the latency to fall time. The study consisted of three consecutive trials of 5 minutes each with a 20 minute rest period between trials. On days 3-5, the mice were allowed to rest for 1.5-2 hrs between the two replicate tests conducted on each of those days.

The results from the rotarod test are presented in the Table below. As shown in the Table below, treatment with ASO improves rotarod performance by up to about 20% on week 5 and about 27% on week 9.

TABLE 12

| Rotarod performance test in ATXN2-Q127 mice. (mean latency to fall, in seconds) | | | | |
|---|---|---|---|---|
| Weeks after injection | | ISIS 564127 | ISIS 564216 | Saline control |
| Week 5 | DAY 3 | 137 | 145 | 123 |
| | DAY 4 | 140 | 141 | 119 |
| | DAY 5 | 155 | 154 | 131 |
| Week 9 | DAY 3 | 131 | 149 | 104 |
| | DAY 4 | 125 | 139 | 104 |
| | DAY 5 | 134 | 139 | 112 |

Example 9: Effect of Antisense Inhibition of Human Ataxin 2 in an ATXN2-Q127 Mouse Model ISIS oligonucleotide was administered in the ATXN2-Q127 mouse model. Motor performance was evaluated using the rotarod test.

Seven week old ATXN2-Q127 mice were subjected to the rotarod test, then divided into two groups of 30 mice each, such that average rotarod performance, average weights, and sex composition were equal across both groups. At 8 weeks of age, one group of mice received normal saline via intracerebroventricular (ICV) injection and one group received ISIS 564216 at 210 µg via ICV injection, dosed in the same manner as described in the studies above. Five weeks later (13 weeks of age), the mice were again subjected to the rotarod test. Six weeks post injection (14 weeks of age), the mice received a second ICV injection, identical to the injection received at 8 weeks of age. Five weeks later (19 weeks of age, 11 weeks after the first ICV injection), the mice were subjected to a third rotarod test.

Rotarod Test

The accelerating rotarod test was performed on the Rotamex rotarod. Rotarod testing was conducted over five days. On the first day, mice were acclimated to the technician by being handled by the technician three times, 5 minutes each time. On the second day, mice were introduced to the rotarod three times, 10 minutes each time at a speed ranging from 0 to 10 RPM. On each of days 3-5, mice were placed on the rotarod at a speed of 0 RPM, then the rotarod was accelerated to 40 RPM over 6 minutes, and this was done for each mouse three times. The three total trials per day were used to calculate a mean value of "latency to fall" per day, in seconds. Latency to fall is defined as the amount of time before the animal falls from the rotarod. It was recorded automatically, when the mouse no longer interrupted infrared beams directed above the rotarod. The time to first passive rotation (when mice stop walking and hold on and revolve with the rod) is also automatically recorded, and generally reflects the latency to fall time.

The results from the rotarod test are presented as the average for each treatment group in the Table below. As shown in the Table below, treatment with ASO improved rotarod performance.

TABLE 13

Rotarod performance test in ATXN2-Q127 mice

| Treatment | Weeks after 1st injection | Weeks after 2nd injection | Testing day | Latency to fall (s) |
|---|---|---|---|---|
| Saline | 5 | n/a | 3 | 218.5 |
|  |  |  | 4 | 240.9 |
|  |  |  | 5 | 236.5 |
| Isis No. 564216 | 5 | n/a | 3 | 240.6 |
|  |  |  | 4 | 257.9 |
|  |  |  | 5 | 259.6 |
| Saline | 11 | 5 | 3 | 216.2 |
|  |  |  | 4 | 198.7 |
|  |  |  | 5 | 212.1 |
| Isis No. 564216 | 11 | 5 | 3 | 194.4 |
|  |  |  | 4 | 226.0 |
|  |  |  | 5 | 242.8 |

What is claimed is:

1. A method comprising:
administering a single-stranded modified oligonucleotide to an animal for treating an Ataxin 2 associated disease, wherein the modified oligonucleotide is at least 90% complementary to SEQ ID NO: 1, SEQ ID NO: 2, or SEQ ID NO: 3,
wherein the modified oligonucleotide is not complementary to a CAG repeat expansion in the Ataxin 2 nucleic acid.

2. The method of claim 1, wherein the modified oligonucleotide has a nucleobase sequence comprising a region of at least 12 contiguous nucleobases which is 90% complementary to an equal length region of nucleobases 606-656 of SEQ ID NO: 1, wherein the modified oligonucleotide comprises at least one modified internucleoside linkage or at least one modified sugar.

3. The method of claim 1, wherein the Ataxin 2 associated disease is a neurodegenerative disease.

4. The method of claim 3, wherein the neurodegenerative disease is spinocerebellar ataxia type 2 (SCA2), amyotrophic lateral sclerosis (ALS), or parkinsonism.

5. The method of claim 1, wherein the animal is a human.

6. The method of claim 1, wherein the administering is parenteral administration.

7. The method of claim 1, wherein the administering distributes the single-stranded modified oligonucleotide to the Purkinje cells.

8. The method of claim 6, wherein the administering improves rotarod performance in the animal by 10 percent, 15 percent, or 20 percent.

9. The method of claim 6, wherein the administering improves motor function in the animal by 10 percent, 15 percent, or 20 percent.

10. The method of claim 1, wherein at least one symptom of an Ataxin 2 associated disease is ameliorated, treated, prevented, or slowed.

11. The method of claim 1, wherein at least one internucleoside linkage of the modified oligonucleotide is a modified internucleoside linkage.

12. The method of claim 11, wherein at least one modified internucleoside linkage is a phosphorothioate internucleoside linkage.

13. The method of claim 1, wherein at least one nucleoside of the modified oligonucleotide comprises a modified nucleobase.

14. The method of claim 1, wherein at least one nucleoside of the modified oligonucleotide comprises a modified sugar.

15. A method comprising:
identifying an animal having an Ataxin 2 associated disease; and
administering a single-stranded modified oligonucleotide to the animal for treating an Ataxin 2 associated disease,
wherein the modified oligonucleotide is at least 90% complementary to SEQ ID NO: 1, SEQ ID NO: 2, or SEQ ID NO: 3,
wherein the modified oligonucleotide is not complementary to a CAG repeat expansion in the Ataxin 2 nucleic acid.

16. The method of claim 15, wherein the modified oligonucleotide has a nucleobase sequence comprising a region of at least 12 contiguous nucleobases which is 90% complementary to an equal length region of nucleobases 606-656 of SEQ ID NO:1, wherein the modified oligonucleotide comprises at least one modified internucleside linkage or at least one modified sugar.

17. The method of claim 15, wherein the Ataxin 2 associated disease is a neurodegenerative disease.

18. The method of claim 17, wherein the neurodegenerative disease is spinocerebellar ataxia type 2 (SCA2), amyotrophic lateral sclerosis (ALS), or parkinsonism.

19. The method of claim 15, wherein the animal is a human.

20. The method of claim 15, wherein the administering is parenteral administration.

21. The method of claim 15, wherein the administering distributes the single-stranded modified oligonucleotide to the Purkinje cells.

22. The method of claim 15, wherein the administering improves rotarod performance in the animal by 10 percent, 15 percent, or 20 percent.

23. The method of claim 15, wherein the administering improves motor function in the animal by 10 percent, 15 percent, or 20 percent.

24. The method of claim 15, wherein at least one symptom of an Ataxin 2 associated disease is ameliorated, treated, prevented, or slowed.

25. The method of claim 15, wherein at least one internucleoside linkage of the modified oligonucleotide is a modified internucleoside linkage.

26. The method of claim 25, wherein at least one modified internucleoside linkage is a phosphorothioate internucleoside linkage.

27. The method of claim 15, wherein at least one nucleoside of the modified oligonucleotide comprises a modified nucleobase.

28. The method of claim 15, wherein at least one nucleoside of the modified oligonucleotide comprises a modified sugar.

* * * * *

SEQUENCE LISTING

```
<160> NUMBER OF SEQ ID NOS: 165

<210> SEQ ID NO 1
<211> LENGTH: 4712
<212> TYPE: DNA
<213> ORGANISM: Homo sapiens

<400> SEQUENCE: 1 accccgaga   aagcaaccca   gcgcgccgcc   cgctcctcac   gtgtccctcc   cggccccggg     60
gccacctcac   gttctgcttc   cgtctgaccc   ctccgacttc   cggtaaagag   tccctatccg    120
cacctccgct   cccacccggc   gcctcggcgc   gcccgccctc   cgatgcgctc   agcggccgca    180
gctcctcgga   gtcccgcggt   ggccaccgag   tctcgccgct   tcgccgcagc   caggtggccc    240
gggtggcgct   cgctccagcg   gccggcgcgg   cggagcgggc   ggggcggcgg   tggcgcggcc    300
ccgggaccgt   atccctccgc   cgcccctccc   cgcccggcc    ccggccccc   tccctcccgg    360 cagagctcgc   ctccctccgc   ctcagactgt   tttggtagca   acggcaacgg   cggcggcgcg    420
tttcggcccg   gctcccggcg   gctccttggt   ctcggcgggc   ctccccgccc   cttcgtcgtc    480
ctccttctcc   ccctcgccag   cccgggcgcc   cctccggccg   cgccaacccg   cgcctccccg    540
ctcggcgccc   gcgcgtcccc   gccgcgttcc   ggcgtctcct   tggcgcgccc   ggctcccggc    600
tgtccccgcc   cggcgtgcga   gccggtgtat   gggcccctca   ccatgtcgct   gaagcccag     660 cagcagcagc   agcagcagca   gcagcagcag   cagcagcaac   agcagcagca   gcagcagcag    720
cagcagccgc   cgcccgcggc   tgccaatgtc   cgcaagcccg   gcggcagcgg   ccttctagcg    780
tcgcccgccg   ccgcgccttc   gccgtcctcg   tcctcggtct   cctcgtcctc   ggccacggct    840
ccctcctcgg   tggtcgcggc   gacctccggc   ggcgggaggc   ccggcctggg   cagaggtcga    900
aacagtaaca   aaggactgcc   tcagtctacg   atttcttttg   atggaatcta   tgcaaatatg    960
aggatggttc   atatacttac   atcagttgtt   ggctccaaat   gtgaagtaca   agtgaaaaat   1020
ggaggtatat   atgaaggagt   ttttaaaact   tacagtccga   agtgtgattt   ggtacttgat   1080
gccgcacatg   agaaaagtac   agaatccagt   tcggggccga   aacgtgaaga   aataatggag   1140
agtattttgt   tcaaatgttc   agactttgtt   gtggtacagt   ttaaagatat   ggactccagt   1200
tatgcaaaaa   gagatgcttt   tactgactct   gctatcagtg   ctaaagtgaa   tggcgaacac   1260
aaagagaagg   acctggagcc   ctgggatgca   ggtgaactca   cagccaatga   ggaacttgag   1320
gctttggaaa   atgacgtatc   taatggatgg   gatcccaatg   atatgtttcg   atataatgaa   1380 gaaattatg    gtgtagtgtc   tacgtatgat   agcagtttat   cttcgtatac   agtgccctta   1440
```

```
gaaagagata actcagaaga attttaaaa cgggaagcaa gggcaaacca gttagcagaa      1500
gaaattgagt caagtgccca gtacaaagct cgagtggccc tggaaaatga tgataggagt      1560
gaggaagaaa aatacacagc agttcagaga aattccagtg aacgtgaggg gcacagcata      1620
aacactaggg aaaataaata tattcctcct ggacaaagaa atagagaagt catatcctgg      1680
ggaagtggga gacagaattc accgcgtatg ggccagcctg gatcgggctc catgccatca      1740
agatccactt ctcacacttc agatttcaac ccgaattctg gttcagacca aagagtagtt      1800
aatggaggtg ttccctggcc atcgccttgc ccatctcctt cctctcgccc accttctcgc      1860
taccagtcag gtcccaactc tcttccacct cgggcagcca cccctacacg gccgccctcc      1920
aggccccct cgcggccatc cagacccccg tctcacccct ctgctcatgg ttctccagct       1980
cctgtctcta ctatgcctaa acgcatgtct tcagaagggc ctccaaggat gtccccaaag      2040
gcccagcgac atcctcgaaa tcacagagtt tctgctggga ggggttccat atccagtggc      2100
ctagaatttg tatcccacaa cccacccagt gaagcagcta ctcctccagt agcaaggacc      2160
agtccctcgg ggggaacgtg gtcatcagtg gtcagtgggg ttccaagatt atccctaaa       2220
actcatagac ccaggtctcc cagacagaac agtattggaa ataccccag tgggccagtt       2280
cttgcttctc cccaagctgg tattattcca actgaagctg ttgccatgcc tattccagct      2340
gcatctccta cgcctgctag tcctgcatcg aacagagctg ttacccctc tagtgaggct       2400
aaagattcca ggcttcaaga tcagaggcag aactctcctg cagggaataa agaaaatatt      2460
aaacccaatg aaacatcacc tagcttctca aaagctgaaa acaaaggtat atcaccagtt      2520
gtttctgaac atagaaaaca gattgatgat ttaaagaaat ttaagaatga ttttaggtta      2580
cagccaagtt ctacttctga atctatggat caactactaa acaaaaatag agagggagaa      2640
aaatcaagag atttgatcaa agacaaaatt gaaccaagtg ctaaggattc tttcattgaa      2700
aatagcagca gcaactgtac cagtggcagc agcaagccga atagccccag catttcccct      2760
tcaatactta gtaacacgga gcacaagagg ggacctgagg tcacttccca agggggttcag     2820
acttccagcc cagcatgtaa acaagagaaa gacgataagg aagagaagaa agacgcagct      2880
gagcaagtta ggaaatcaac attgaatccc aatgcaaagg agttcaaccc acgttccttc      2940
tctcagccaa agccttctac tacccccaact tcacctcggc ctcaagcaca acctagccca      3000
tctatggtgg gtcatcaaca gccaactcca gtttatactc agcctgtttg ttttgcacca      3060
aatatgatgt atccagtccc agtgagccca ggcgtgcaac ctttataccc aataccttatg     3120
acgcccatgc cagtgaatca agccaagaca tatagagcag taccaaatat gccccaacag      3180
cggcaagacc agcatcatca gagtgccatg atgcacccag cgtcagcagc gggcccaccg      3240
attgcagcca ccccaccagc ttactccacg caatatgttg cctacagtcc tcagcagttc      3300
ccaaatcagc cccttgttca gcatgtgcca cattatcagt ctcagcatcc tcatgtctat      3360
agtcctgtaa tacagggtaa tgctagaatg atggcaccac caacacacgc ccagcctggt      3420
ttagtatctt cttcagcaac tcagtacggg gctcatgagc agacgcatgc gatgtatgca      3480
tgtcccaaat taccatacaa caaggagaca agcccttctt tctactttgc catttccacg      3540
ggctcccttg ctcagcagta tgcgcaccct aacgctaccc tgcacccaca tactccacac      3600
cctcagcctt cagctacccc cactggacag cagcaaagcc aacatggtgg aagtcatcct      3660
gcacccagtc ctgttcagca ccatcagcac caggccgccc aggctctcca tctggccagt      3720
ccacagcagc agtcagccat ttaccacgcg gggcttgcgc caactccacc ctccatgaca      3780
cctgcctcca acacgcagtc gccacagaat agtttcccag cagcacaaca gactgtcttt      3840
```

-continued

```
acgatccatc cttctcacgt tcagccggcg tataccaacc cacccacat ggcccacgta      3900 cctcaggctc atgtacagtc aggaatggtt ccttctcatc caactgccca tgcgccaatg      3960
atgctaatga cgacacagcc acccggcggt ccccaggccg ccctcgctca aagtgcacta      4020
cagcccattc cagtctcgac aacagcgcat tccccctata tgacgcaccc ttcagtacaa      4080
gcccaccacc aacagcagtt gtaaggctgc cctggaggaa ccgaaaggcc aaattccctc      4140
ctcccttcta ctgcttctac caactggaag cacagaaaac tagaatttca tttattttgt      4200
ttttaaaata tatatgttga tttcttgtaa catccaatag gaatgctaac agttcacttg      4260
cagtggaaga tacttggacc gagtagaggc atttaggaac ttgggggcta ttccataatt      4320
ccatatgctg tttcagagtc ccgcaggtac cccagctctg cttgccgaaa ctggaagtta      4380
tttatttttt aataaccctt gaaagtcatg aacacatcag ctagcaaaag aagtaacaag      4440
agtgattctt gctgctatta ctgctaaaaa aaaaaaaaaa aaaaaatcaa gacttggaac      4500 gccctttttac taaacttgac aaagtttcag taaattctta ccgtcaaact gacggattat      4560
tatttataaa tcaagtttga tgaggtgatc actgtctaca gtggttcaac ttttaagtta      4620
agggaaaaac ttttactttg tagataatat aaaataaaaa cttaaaaaaa atttaaaaaa      4680 taaaaaagt tttaaaaact gaaaaaaaaa aa                                    4712
```

<210> SEQ ID NO 2
<211> LENGTH: 151001
<212> TYPE: DNA
<213> ORGANISM: Homo sapiens

<400> SEQUENCE: 2

```
tcccaaagtg ctgggattac aggcgtgagc caccacactg gccaaaactt gttcttaaga        60
ttgtattctg ggaccttgat tccaatcaga gaaaagtgat tgtattttt tatttttatt       120 tttttagat aaagtttcgc tcttgttgcc caggctggag tgcagtggtg ccctctttgg       180
tcactgtaac ctccgcctcc tgggttcaag cgattctcct gcctcagcat cctgcgtagc       240
tgagatcaca gatgcccacc accacgccca gctaattttt tcgtattttt agtagcgatg       300
gggtttcacc atgttggcca cgctggtctt gaactcctga cctcaggtga tccatccgcc       360
tcggcctccc agagtgctgg gattacaggt gtgagccacc gcgccaggcc aagtgtttgt       420
atttctatta aagaaagaat ataacgggac accattgacg acctgctcca ttgcaggcct       480
ccttgctgtt cctcagactc ccccctcaga gcctttgccc tcgctgtgcc ctccacctgg       540
agcgtttctc cccaggatcc tcatgcccat gctcatttgg gtccctgccc catgtcaccc       600
tctccaggag cttccctca cagcagccct ggcctgtacc acagccgggt acaggtattt       660
ttttgtttca actggttttt tagttccagt ttcccttagg ttacttatt tatttattta       720 tttatttatt ttttgagacg gagtctcgct ctgtcgccca ggctggagtg catgatctcg       780
gctgactgca acctccacct cccgattca agcaattctc ctgtatcagc ctcccgagta       840
gctgggatta caggcgccca ccaccacacc cggctaattt ttatatttttt ggtagagacg       900 gggtttcacc atgttggcta ggctaggtta atttttaaag gttttgcaa tggtcccttg       960 atctactttt taccttagat gggaaataaa actgatttcc tacattggca gaatacaatg      1020 atcattttg cctggactat ctaggaggtt aatttcagtt ggactactga aaactgctgg      1080
ttcaatcatt ctccacgttt atctaagtct ttaccttat ctggacagtt ctaggacatt      1140
gaggggaatt ttggtgtttc ttccctatt atttcctgaa gtcattcac tttaaaaaac      1200
```

```
aatagattca ctgctcaaaa aaaaaaaaaa aagttaccta ctttctactt gcttccagtt    1260
taactgcaac acattttaaa aagagtctac tgtgctggct gggtaagtta aattaaaact    1320
tctaaagggt ccaaggtcta aagttcgcac attgttttga ggtcggctct gtctctaccg    1380
agggagatcc cattatccgt agttctacca gtcccaatcc catatatttc ctttagaatc    1440
tcatgaatga ggaaaaagaa gttcaagtga gggaacatag gttcaaatga aggtcagata    1500
cctaaaagag ttttctggtg actgtgcgcg gctggggtgg aaaaagtggg gaaaaggtac    1560
ccagatgtgg gtggccccgg agggttgctc cactccagcc ccggcagggc aggacagcgc    1620
ggcctgcctg gtagatgccc cgagccactg gagcgcctac tgtgtggcgg gcgggggacg    1680
gcaggaaaac ggcaggatgc tgtgtcccct gaatctggca gggttctagg tgctttacac    1740
gtagcaagac acattctccg ccccaaggca ctcgcagtca gtccattttc tgggttgcat    1800
caggtggggg caaactaggt ccccgcagaa gtgaagatgc tgaaggaata cagtaggaga    1860
agaaatgctt ctctcctgtc ctccacacca ggcaggcccc agaggctgag accgacacgc    1920
cctccccgaa gggcagaccc gccttgagga aggcggatcc gggtagggac cgccgcctgg    1980
ccctcacccg accccgaga aagcaaccca gcgcgccgcc cgctcctcac gtgtccctcc    2040 cggcccgg gccacctcac gttctgcttc cgtctgaccc ctccgacttc cggtaaagag    2100
tccctatccg cacctccgct cccaccggc gcctcggcgc gccgccctc cgatgcgctc    2160 agcggccgca gctcctcgga gtcccgcggt ggccaccgag tctcgccgct cgccgcagc    2220 caggtggccc gggtggcgct cgctccagcg gccggcgcgg cggagcgggc ggggcggcgg    2280
tggcgcggcc ccgggaccgt atccctccgc cgccccctccc ccgcccggcc ccggcccccc    2340
tccctcccgg cagagctcgc ctccctccgc ctcagactgt tttggtagca acggcaacgg    2400
cggcggcgcg tttcggcccg gctcccgcg gctccttggt ctcggcgggc ctccccgccc    2460
cttcgtcgtc ctccttctcc ccctcgccag cccgggcgcc cctccggccg cgccaacccg    2520
cgcctccccg ctcggcgccc gcgcgtcccc gccgcgttcc ggcgtctcct tggcgcgccc    2580
ggctcccggc tgtccccgcc cggcgtgcga ccggtgtat gggcccctca ccatgtcgct    2640
gaagccccag cagcagcagc agcagcagca gcagcagcag cagcagcaac agcagcagca    2700
gcagcagcag cagcagccgc cgcccgcggc tgccaatgtc cgcaagcccg gcggcagcgg    2760
ccttctagcg tcgcccgccg ccgcgccctt gccgtcctcg tcctcggtct cctcgtcctc    2820
ggccacggct ccctcctcgg tggtcgcggc gacctccggc ggcgggaggc ccggcctggg    2880
caggtgggtg tcggcacccc agcccctcc gctcccgggcc cggcgtcccc tccccgcgg    2940 cccgcgccgc cgtccccgcc ccgtgacccg ccgggctacc cggggtgggc tggggccgg    3000 cagcgcgggg gagactcgct cgggcctgag ccccgaggct cggccggtgg gcgcagccgg    3060
ggtcctctgg gattgtcagg cctgtccagc ctcccgcagc atccccgccc cctccccgg    3120 cggtcaagat ggagggagcg gcggcctcc cctccccacg cgtgttggga ggggttctcg    3180
ggtagcggcg atggtcagcc ccggctcccc cttccgcacg atcctccgcc cgcagcgtgg    3240
ggatgctcgg gcagctcctc cactcccggt ttaggtgtga acgttggagg ggtctggagg    3300
ctgtggtggc gttttccgga acatgtcccc ctccatgggg gacatctctg gagggggagaa    3360 gttagggccg cgtcccccgt gccggttaaa ggggtaggca ccgggctcct ccggaatcat    3420
cagggtctgt cggggctctc tccccgcccc ctccgagtcc tgggaaagat cggaggacgg    3480
ggtggagaca agtgggcctt ggcccccgca ccccctctgcg ttcgtgtccg aggcggcggc    3540
gggggctccc gaactcccct gaaatcgtgg ggctccatgt ggcctccggc agcgttccac    3600
```

```
cctcccccac ctggggaagg gaaggggtgg ggagtgcccg gccccgtccc ggccttcctc   3660 cttccccgc cagacctctc cggcgcgcgg gtggtggccg atccgcattg ctgttcgagg    3720
ccgcagtgga gaaggcgcct gtggaacatc ggtgggtgag ggctggaccc aggctggacc   3780
ctggagatcc ggggtggcgg tgctggtggc aggggggcggg caccctgcgc acttatccca  3840 accccgccc caatttcgga aatgctagga gagagagatt gcagcagggg acgtggtcgg    3900
gttcctgaag gcagaaaggc gggtgtttac tagcgtcttt ttccctccta agccggggtt   3960
gtagtagggg ctgggggctc agtgttgtcc cggctaactg ggtttgactc gagggtgtgt   4020
ttgtgcagga gggcctgttg ggggtggcgg gcggttgtca gttcgtattt cacgaactaa   4080
gaaaatgctt agtgttcaaa gggagaagga aacgtcaata gactccattc cattgtggcc   4140
ggtgtcctta acttcgggag tgccgccaga gcttaccaag ggcacgcaag tccatttccc   4200
ttgtgcctca agtccatccg tgttgtaggc actactgtgc cttctttagg cctaggccgc   4260
cggcttgacg gcgggtgacc ggcgtcctcc ttaaataggc atcttgggct ttggaaggtg   4320
gaataagagg attttttcatt caccgagtt ttcttttga aaacacattt tcagcaaccc    4380
atttccaaag aattttttatt tacagcagaa attccccatc aagaggaatc agctggtttt  4440
taaggaattc tgctgccttc aaagggggcg gaaacagtcg gttatttgac tttacacgcc   4500
ccgccccccc ttccccttct ctgagtctga agcatcccaa acactactta gccaaactag   4560
ttcagatgaa gtgatcgttt ccccaagtag ggtaacttca gtttccttt ttcgttggca    4620 tctagcgaaa aatgaaaaaa tttaaaatac aactttttata gaaaaggatg tattctgttt  4680
ttactttctt aggtattagg aagagatttg gcagataatt caacatgttc aaatatataa   4740
acattaaaac taaggttatt aagttgcatt gactactagg cttaaaaatt agattataag   4800
agaatttgct cctgagtagt ttgagtgatc aaagatattt ggaatgtttt agtaccacaa   4860 ggtcttttt ctgttccttg aggctttaca acaatttaag gttaatttag atttttcctt    4920
gctttaagtt cttttacttg agacctaaat ggcagcccctt attctttctg atgaataggt   4980
gaaattttgt ttactgtgtt ggatttgtgt aatgtgaagt tttattcttg aacagatcgt    5040
taatgtactt gtagaattac tttgaatttg aatcactttc ctgcattcct tgtaaataag   5100
tttcagcttc tagaatctcc tcacttaggt ttgtgcgtat caacagtgaa aataagtctc    5160
tgagagcaag ggtgaaaaaa aatgcagcat tcggtttgac aagtttcgag atagcaaaat   5220
atgcttgaaa gtctggaaat tcacatctgc tttaagaaac atttcataat ttgactttgt   5280
gtgtgtgtgt gtgaatagtt tttcatgact ttcagaagtg atttattttg ttctttgtta   5340
tatatatttt tgaaggtggc tgttttagga aagataatgt aatcacaata ttagaacata   5400
attttactgt aatctaattt tgtgtgtgtg tgtgtgtgtg tgtgtgtgtg tgtgtgtgtg   5460
ttttggatgg aatctcactc tgtcgcccag gctggagtgc agtggcctga tctcagctta   5520
ctgcagtctc tgtctcctgg gttcatttaa gtgattctcc agcctcagcc tccccagtag   5580
ctgggattac aggttcgtgc taccacacct ggctaatttt tttgtatttt tagtgaggac   5640
gggattttgc catgttggcc aggctggtct cgaactcctg acctcaagtg atccgcctgc   5700
cttggcctcc caaagtgctg ggattacagg cgtgagctac tgcccctggc caattttgt    5760 atttttagta gagatggggt ttcaccatgt tggccaggct ggtctcgaac tcctcctgac   5820
ctcaagtgat tcgccagcct cggcctccca aagtgcagg attacaggca ggaatgagcc    5880
actgccccca accatcagtc taattcttat ttttgctttt taccttttca tttttatgta   5940
```

```
gtagaggtga ttgtgtatgt tattttgtag ttagcttttt tcccctgaac gttgtattgt    6000
aaatgtaaat tttttttttt tttttgaga cagagtctcg gtgtttgccc agtctgaagt    6060
gcagtggtac gatctcagct cactgcagcc tctgactcct gggttcaagc gattctccca    6120
cctcagcctc ttgagtagct ggggctacag gaatgttcca ccacgcttgg ctaattttg    6180 tattttggt agagacaagg tttcaccatg ttggccagtt tggtctcgta ctaccgacct    6240
caggtgatgc gcccgcctcg gcctcccaaa gtgctgggat tgcaggcgtg agccactgcg    6300
cccggctgta aggttttac ttaaccattc tattgttggg aattgggttt ccactttttt    6360
gttatagata gtggtgcagt gaacattttt aaatagcttt ttgcttcagt gtaattattt    6420
ccttagagaa agttaccaag agtggtttta ctagttcaga gggcttcagg attttttatgg    6480 ctcttgctag cggtgctcta ttattcttta gaagacttgt attacttcca gtgtcaagaa    6540
ggttgctctt ccatggaatg gtttctttgt agtttgtcaa atattgtggg gaattttta    6600 aggaaaaatt gcattttac tgtcaagtgc atatatatt aagtgcttt gttagttact    6660 ggattattga tatttgagtt taatttggtt cctctgagga tttaataagg taatatatgt    6720
gaagatgttt tgaaacctgt aaccattatt attaatgagg gtacttggtt tatctgtcgt    6780
gctgatagta ctgagtaaag tgcaggaatg aaattcctga ggaactgttc taaagctttg    6840
ttgttgttgt taaccttct ttttcatctg aaagtgtttt ttattagctg ctagcctatg    6900
accaagttat ttttggtaac tttttgtaa tttcatggca ctattgggaa ttttcgctgg    6960
ttgactcttc ttcttctaca ttcccttccc cattaaaaat aaaatatgg atttacaatt    7020 gttactctat tcctaaacct aaataatatg acattagaat tgcttgggat acaggattca    7080
gtctgaataa aatatttttc ttttagtgat tttcagctta gtattttac tgcttctttc    7140 tcttgaggca ttgcaactta aaaattgtgc tgtttagcca ggcgcctgta atcccagcta    7200
cttgggaggc tgaggcagga gcatcacttg agcccaggag gcggaggttg cagtcagctg    7260
agattgtgcc actgcactcc agcctgggag acagagtgag actctatctc aaaaaaaaaa    7320
aaaatgtgct gtgatttaat gtagttgttc atcatgcttc catttaaatt tcagtgagac    7380
tgttcatctt ttgcagttaa atatcttgta gaagggccta aaatatctac gttgaataca    7440
gctttattga agcatctatg tacatggggt ttttgggatg aatcagtgaa taaagcaaac    7500
atattgtcct tttggagttt acattctaat gtgactaggc agacaatgag acattaaatt    7560
accagcctat gtataatagt gtataagagc tatggaatta gaagaagca gattaaaggt    7620 atagggagtg tggggagggg aatgagttac aatttaaat ggattggggg aacttaattg    7680
aggagctaac atttgagcaa agatttgaag gttgggtatt tagccgtttg ctttttatct    7740
aggttaatta gtcatgtggc ttcattagta atttataagg tttaaatggc atcatccttt    7800
gttattcttt tatgtgcaca ttgatactaa ccatctctga agttagacca aaaaagttaa    7860
ttgacattga gggtcattag aggtaaattg tagatggcta ttactaacca aagagacatg    7920
ttttgttttt cttttgggct tacgtatttt acctaattag tttagttttt gtttcaagta    7980
tgtggagaaa ataaactttt taagtttggg ccaaaacttg ctttggtttt ctttttctt    8040 ttctttttt tttttaaga gaaaatgta agcctgtagt tgcttaaaga ttccacattc    8100
tgaaacagtg aaaacatggg atcagtcatg gtgttccttt ttttggttaa atgtaaactt    8160
gtattttcag tgttactcta attagcaatg gtttatactt ctacataagg gatgttaact    8220
catattgtag ctatttaata gccatatatt ttgacttaaa ggaggatctc aaggccaggc    8280
gcggtggctc atacctgtaa tcccagcact ttaggaggct gaggcgggtg gatcacctgg    8340
```

```
ggtcaggagt tgagactag tctggccaac atggtgaaac ccccatctct actaaaaata    8400
caaaaattag ccgggcatgg tggtgggcgc ctgtaatccc agcttcttgg gaggctgagg    8460
gaagagaatt gcttgatccc ggaggttgca atgagtgcgg aggttgcagt gagctgagat    8520
catgccatta cactccagcc tgggcaacag agcgagactc tgtctcaaaa caaacaaaca    8580
aacaaaaaaa ggaggatctc atttttttgt cctaaatagc tacagccgtg ttagaactgt    8640
caccttagca aagtattgtt ttttttacttt gaaacgaatt ttaaggtttt agaagattgt    8700
tctctagaat tacaattttc tgttttgact agtgatagta ttttgatgtt gtgtaaatag    8760
ttgagcatga acaaaaccct attttttttt ttagctattt caagtgattg tgacaacttc    8820
aacggagatg taaacagttt attaacagtc acacctatta tcttttttt tttttttttt    8880 ttttgagacg gagtcttgct ctgtcgccca ggctggagtg cagtggcacg atctctgctt    8940
actgcaacct ttgcctcccg ggttcaagtg attctcctgc ctcagcctcc tgagtagctg    9000
ggtctacatg cgcacaccac cacgcctggc taatttttgt attttagta gagacagggt    9060 ttcaccatgt tggctagaat ggtctcaaac tcctgacctc aggtgatcca cctgcctcag    9120
cctcccaaag ttctgggatt acaggcatga gccaccgtgc ttggccgctg ccgtatcttt    9180
ttaaatgaaa gtacttgtgt ttttttgtt ttttccaaa ggatatctgg gtcatctatg    9240
atgttactgt taccatctaa gggttttttt gtttgttttt gagacagagt ctctgtcgcc    9300
caggctggag tgcagtggcg tgatcttggc tcactgcaac ctccgcctcc caggttcaag    9360
caattctcct gccttagccc tcccgaatag ctgggattac aggcacccgc caccatgcct    9420
ggctaagttt tgcatttta gtagatatgg agtttcacca tgttggccag gctgctcttg    9480
aactcctgac ctcaggtgat tcgcttgcct cggcctccca aagtgctggg attacaggcg    9540
tgagccaccc ccgcccagcc tcatgagcta aggtgttttt ttttttttg agacagtttt    9600 gctctttccc aggctggagt gcagtggtgc aatctcagct cactgcaacc tctgtttccc    9660
gggttcaagc gattctcctg cctcagcctt ctgagtagct gagattacag gtgcctgcta    9720
ccccactcag ctaattttg tattttagc agagacaggg tttcaccatg ttggttaggc    9780
tcatctcgaa ctcctgacct taagcgatcc acctgccttg gcctcccaaa gtgctggat    9840 tataggcatg agccaccgtg cgcagcctac cctgtctctt aaaaaacagt aacaacaaca    9900
acaacaacaa aaatcctaa atcttaaaaa tggaaggcaa aaactctaag ctttgagaga    9960
ttaggggact tgcccaaagc aatatttgta ggattttatt acacctctcc ctttatttat   10020
ttttttagag tcaaggtctc cctctgtcac ccaggctgga gtgcagcctc aatctatggg   10080
gccaagcatt tctcctgtct tagcctcctg agtagctgga actacaggtg tacaccagct   10140
ggctaacatt taaattttt gtagagacag ggtcctgcca tgttcccag attggtctca   10200 aactcctggg ctcaagtgat cctcctgcct cagcttccca aagtgctgag attacaggtg   10260
tgagccactg caccgagccc cctcccttta ttttatttt taaattttaa gttctggggc   10320
ccctcccttg aaataaatag aaacgtaata tatacacaag atcatgctgt gtattttaag   10380
gcaatggtcc tcaaccttt taacactagg gaccggtttt gtggaagatg ttttttccat   10440
aggggcaggg gatgatttg agatgaaact gttccaccgg ccgggcacgg tggctcacgc   10500
ctgtaatccc agcactttgg gaggccgagg cgggcagatc acgaggtcag gagatcgaga   10560
ccatcctggc taacatggtg aaaccccct ctactaaaaa tacaaaaaaa ttagctgggc   10620
gcggtggagg gcgcctgtag tcacagctac tccggaggcc gaggcaagag aatggcatga   10680
```

```
aacccgggag gcagagcttg cagtgagctg agatagcacc actgtacttc agcctggggg   10740
acaaagtgag actccgtcta aaaaaaaaaa aattgttcca cctcagatca ttatgcattt   10800
gttagattct cataaagagc atacaaccta catctcttgc tatatgcagt tcccagtagg   10860
gtttgtgctt ctataagaac ctaatgctgc acctgatcta acaggtgggg ctcaggtgct   10920
aatgctcaca cagctcctgt tgtgcagtct ggttcctaac aggcctgttt ttttttttt    10980 aattagatgg agtctcgctc tgtcaccagg ctggagtgca gtggcacgat ctcagctcac   11040
tgcaacctct gcctcccggg ttcaagcgat tctcctgcct tagcctccca tgtagttggt   11100
actacaggcg cacactgtga tgcccagcta atttttgtat ttttagtaga cgggggttt    11160 caccatgttg gccaggatgg tgtcgatctc ctgaccttgt gatccgccca acagcctccc   11220
aaagtgctgg aattacaggc gtgagctgct gcgtccggcc ccctaacagg cttgttttat   11280
ggaatacagt cacggacagt acttgccctt caggatatct ttttgtaacc ttgattttgg   11340
cttgctaaaa taggaggtct attttctttt ctttgttttt aatgtatgtg gttctgtact   11400
tacgtggtgt gaaatctaca taaatgttaa atccttggtt atttatttat tttgagacag   11460
agtctcactc tgtcacccag tctggaaagc agtggcataa tctcggctca ctgtaacctc   11520
cacttcccag gttccagtga ttctcctgcc tcagcctcct gagtagctgg gattacaggc   11580
atgcaccact acacctggca aattttttgta tttttttttta gtagagatgg ggtttcacca   11640
tgttggccag gctcgtcttg aactcctgac cttaggtgat ctgcctgtct ggcctccca    11700 aagttttggg attacagcat gagccactgc gcctcgcctt attttttttga dacaggttct   11760 agctctgtca cccaggcggg agtgcagtgg tgccatcatg gctcattgca acctcgagtt   11820
ctcaggccca agtgatcctc ctatctcagc ctcctgagta gctgggacca caggcatgcg   11880
ccactatgcc cagcaaaatt tttgtttcac tctgttgcct agggtggggt gcagtggcag   11940
gatatcggct cagtgcaacc tctgcctctt gcgttcaaat gattctcatg cctcagcctc   12000
ccgagtagct gggattatag gcatgcgcca ctacacctgg ctaatttttg tattattggt   12060
agagatgggg ttttatcatg ttggccaggc tggtctcgaa ctcccgacct caggtgatcc   12120
atataccttg gcctcctgaa gtgctggaat tacaggcata agccactgcg cctagctttt   12180
ttgtttgttt ttattttgta gggacagaga ttttacctgt tgcccaggat ggccttgaat   12240
tcctgacctc aaacaatttg ccctccttgg cctcccaagg tgctgggatt acaggtgtga   12300
gccactatgc ctggctggtt ttttaaatta ttattattgt ttgtgtgtgt gtgttgcagg   12360
atcttaccct gtcacccagg ctggaatgca gtgatgtgat ctcggcttac tgcaacctcc   12420
gcctcctagg ttcaagtgat tgtcctgcct cagcctcctg agtagctggg ataacagctg   12480
tgtgccacca tgcctggcta attttttgtat ttttagtaga gatggggttt catcatgttg   12540
gccaggctgg tctcgaactc ctgaccttag atgatccacc cgcctcgtcc tcccaaagtg   12600
ctgggattac aggtgtgagc caccgtgacc agtttggttt agtttttttt ttttttttt    12660 tttttttttt tttttgagaa atctcgctct gtcgcccagg ctagagtgcg gtgacacaat   12720
ctcagctcac tgcaagctcc acctcccagg ttcatgccat tctcctgcct cagcctcccg   12780
agtagctggg actacatgcg cccgccacca tgcccggcta attttttttta tgcattttaa   12840 gtagagatgg ggtttcactg tgttagccag gattgtctca atctcccgac ctcttgatct   12900
gcccgcctcg gcttcccaaa gtgctgggat tataggcatg agccaccgcg tccggcctgg   12960
tttggtattt tttttatgag tctggggttgt ttatgaaaac ttgtcacagc tgttaacctt   13020
aacttttttt ttttctttttt tttccgagac ggagtctcgc tctgtcacct aggctggagt   13080
```

```
gcagtggtgc gatctcggct cattgcaacc tctgcctccc aggttaaagc gattttctg    13140
cctcagcctc ctgagtagct gggactgcag gcacgcacca tctcgcctgg ctaattttg    13200
tattttagta gagatggggt ttcaccatat tggccaggct ggtctggaac ttctggcctc    13260
aagtgatcca cctgccttgg cctcccatgc ctggcaacct aacttttta tttgctggta    13320
attatttgtg tttgcattca tgtgaaaatt tgaaattctc attaacattt aaagattctt    13380
acatagattg cttgtaattt taaccctgaa gttgtgtcaa gtgactttac aatgtcaatt    13440
tgttttattt atttatttat ttatttattt atttattttt gtgataggat ctggctctgt    13500
tgctaaggct ggagtgcagt gttgcaaata cggctcactg caacctctgt ctcccgggtt    13560
caagccatcc tcccacctca gcctcccaag tagttggaac tactggtgcg ccccacagtg    13620
cctgcctagt tttttgtat tttcagtaga tgtggagttt tgccatgttg atcttgaact    13680
catggcctcg agtgatccac cccacttagg cctcctaaca tgctggtgtt acaggtgtga    13740
gccactgtgt ccagcccgaa aatgtcagtt tcgtgccatg attaatagct aactacattt    13800
tgggaatgta ataaaatttc attctataat gaagtctttg taaaactcat tagttgtggt    13860
atgaggcttg tcggcaatat aagtgaacgt ggtttatttt tattaactgt atcagaactt    13920
tagaatgttg gtctcctgaa accattgcct tgagaggctt tattgaacag tgttgccaat    13980
gatcagtttt tttttaaatt tccttttttt tgagactgag tcttaccctg ttggccaggt    14040
tggagtatag tggtatggtc atggctcact gcagcctcaa catcctgggc tcaagcagtc    14100
ctcctacctc agtctcccga gtagctggaa ctacaggtgt atgccaccat gcctggcttt    14160
tgtatatttt gtagagacag ggtttagcca tgttgcccag gctggtctca aactcttaaa    14220
ttcaaatgat ccacccacct agttttccca aagtgcttta attacatgtg tgaggcaccg    14280
tggctggcca ggtcaaatat ttttcattga cgttttcat attgcttttt aaagtcatgt    14340
taaaatattc ttaataattt ttctaagtgg aattaatctt gattataatt ttagtttttt    14400
ataaagggcg ggttttgaaa caagtactgc attttttctt tcgggtttat aaacatttgc    14460
tgtggacttt gtgcagttaa ctattttcat tcctgaaaca catttcgaaa tcaggaattg    14520
aagactaaat gtcttttcac tgaagcttga gcagatttta gaaaggggag ttctttttt    14580
ttttttttt tttggtagaa atgggggtct tgttatgttg cccaggctgg cctccaactt    14640
ctgggcttaa actgtcctcc tgctttagcc tctggtctgg agagttcttt atggcctctt    14700
tgagaacttt tactttacac atgattctat ctagcttctt tttctgatgt acatattggc    14760
agcaagtaga aaagcaatgt tttcagaggc agatatatta acagcaatga gaaataacag    14820
tagcgtgata gaaagttgaa agacttagct gggtgcggtg gctcacgctt gtaatcccag    14880
cactttggga ggccaaggag ggtggatcac ttgaggtcag gagttcgaga ccagtctggc    14940
caacatggtg aaaccctgtc tctactgaaa acagaaaaa gggccgggcg tggtggctca    15000
ccctgtaat cccagcactt gggaggttg aggaggcgg attacaaggt caagagattg    15060
agaccattct ggccaacagg gtgaaacccc atctctacta aaaatacaaa aaattaaat    15120
gggcgtggtg atgtgtgcct gtagtcccag ctactcggga ggctgaggca ggagaattgc    15180
ttgaacccgg gaggcagagg ttgcagtgag ccgagatcgg gccactgcac tgacgacaga    15240
gggagactcc gtctaaaaaa aaaaaaaa aaaaaaacc agacttgggg ctgggcgggc    15300
gcctgtaatc ccagctactt gggaggctga ggcaggagaa tcgcttgaac ccggaggtg    15360
aaggttgcag tgagctcaga ttgtgccact gtgcccagc ctgggccaca gagcagagtg    15420
```

| | |
|---|---|
| agactctgtc tcaaaaaaaa aaaaaaagtt tggaagactg gtggctgggc atggtggctc | 15480 |
| acacctgtaa tcccaacact tgggaggct gaagcaggca gattacctga gcccaggagt | 15540 |
| tcaagtccag cctgggcaac acagggaaac cccatctcaa caaaaatat taatacaaaa | 15600 |
| aatttagcca gtcatggtcg tgcacttctg tagtctcagc tacttgggag gctgaggcag | 15660 |
| gtggttcact taagtctgga tgtcgaggtg agccatgatt gcaccactgc actccagcct | 15720 |
| gggcgttaaa atgagacctt atctcaaaaa aacaaagcaa agagcctggg aactactaaa | 15780 |
| atgggaacta ctaaaaaaca gacacaagag ctcaacaagt ataccattct gggaggtttt | 15840 |
| tttttttttt tttttttttt ttttgagat ggagttttgc tcttgtcacc caggctggag | 15900 |
| tgcaatggcg ccatctctgc tcactgtagt tccgcctccc aggttcaagc agttctcctg | 15960 |
| cctgactcct gagtagctgg gagtacagat attggtcaca caccgggtta attttttgtat | 16020 |
| ttttagtaga cacgggtttt ccccattttg gccaggctgg tctcgaactc ctgacctcag | 16080 |
| gtgatccgcc tgcttcagcc tcccaaagtg ccgggaccac aggcgtgagc caccgcacct | 16140 |
| ggcttttttt ttttgacata gaatcttgtt ctgttgccca ggctgagtg caatggtaca | 16200 |
| atcttggccc actgcaacct ctgcctccca gcttctagcg attttcctgc ctctgactcc | 16260 |
| tgagtagctg ggattacggg tgcccgccac cacacccgga taattttgt attttttagta | 16320 |
| gagatggggt tttgccatat tggccaggcc ggtcttgaac tcctgacctc agatgatcca | 16380 |
| cctgcctagg cctcccaaag tgccgggatt acaggcgtga ccaccactc ccggcctggg | 16440 |
| agttttgact gtaagtttat agctgtatat cttaggccct aagggcatta ctgttttata | 16500 |
| gcacagtgta gttagttaat gtgctcataa tggtgactca taacaccagg ttaaatgatt | 16560 |
| ttttatatct cccaaagaag tattttttcaa tctgcagatc atgaccccttt agtagattgt | 16620 |
| gaaacacatt agtggattat gacaagcatt tttagaaaaaa tgaaaaagaa taagaagtgt | 16680 |
| taggatgcat tgcattattg aaataattgt ttttgagatg gagtttcgct cttagttgcc | 16740 |
| gaggctggag tgcaatggcc cgatctgcct cccgggttca gtgattctc ctacctcagc | 16800 |
| ctcctgagta gctgggatta cagacatgct ccaccatgcc tggctaattt tgtatttagt | 16860 |
| tttagtagag atggggtttc tccatgttgg tcaggctggt cttgaactcc tgacctcagg | 16920 |
| tgatccactt gcctcggcct cccaaagtgc tgggatacat ggcatgaacc cctgtgcccg | 16980 |
| gcctaatttt tgtattttta gtagagatgg ggtttcacca tgttggccag gatagtcttg | 17040 |
| atctcttgac ctcgtaatct gcccacctcg actcccaaag tgctgggatt acaggtgtga | 17100 |
| gccactgcac ccagctgcca agaattgttt taagctttgg tttgagttaa tgtatatata | 17160 |
| ccgcattgta attcaaaatg taatttttgg ccaactctgg gcacattgcc tatggactag | 17220 |
| tcctgctctg ccacgagcag caacagttca atgaatttt tttttttttt tttttttttt | 17280 |
| tttttttttg agacagggtc tctgtcacca aggctagaat gtagtggtgc agtctcggct | 17340 |
| cactgcaacc tctgtttcct gggctcaagc gatcctccca cctcagcctc ctgagtagct | 17400 |
| gggagtacag gagcacgcta ccatgcctgg ctaattttg tattttttga agagatgagg | 17460 |
| ttttgccatg ttgttcaggc tagtcttgaa ctctggagct cagatgatcc acccaccttg | 17520 |
| gtgtccagaa atgctgggat tacagggatg agccaccgtg cctagccaaa aatttttttt | 17580 |
| taagtaattt tttattgata tagtcaaaaa agttactgct ttagagccag agaaacgcag | 17640 |
| taaaaggatt gagaaagagt tttgaggtta tatctaagct agggttgtca gatttggcaa | 17700 |
| atagaaaatac aggacactca gttaaatttg aattttttgat gaacattgac cagttttta | 17760 |
| gtataattgt gtattaaaatt gcatagaaaa aagttattta tctaaagttg aaatttaact | 17820 |

```
gagcatcttg tattttatct ggcaactcca gtctaagctg gaatcatggt tcactgtttt    17880
tttttttttt tttttttttt gagtcggagt cttgctgtgt tgcccaggct ggagtgcaat    17940
ggtgcgatct tggctcactg caacctccac ctcctgtgtt caagtgattc tcctgcctca    18000
gcctcctgaa tagttgggat tacaggcacc caccaccatg cccagctaat ttttatattt    18060
ttagtagaga cggggttttc gccatgttgt tcaggctggt cttgaactcc tgacctcagg    18120
tggtccgccc acctgggcct cccaacgtgc tgggattaca ggcatgatct accgtgcctg    18180
gccatggttc actcttcagt aactaaaatt taagctctat gaaagcagga actttgtttt    18240
gttcactatt gattgtatcc ctatttcttg aatggttggc acttaactgc ttggtcacat    18300
gtttgaatgg gcaagttact cagccactct caggcttagt ttatttacct attaaaagag    18360
aaagaatatc ttccttggct gggcgcggtg gctcacgcct ataatcccag cactttggga    18420
ggctgaggcg ggtggatcac gaggtcagga gatcgagacc aacctgggca acattgtgaa    18480 accctcatctc tactaaaata gaaaaaatta gctgggcatg gtggtgcgca tctgtagtcc    18540
cagctactcg agaggctgag gcaggggaat cgcttgaacc caggaggtgg aggttgcagt    18600
gagccaagat tgtgccactg cactccagcc tgggcgacag aacgagactc tgtctccaaa    18660
aaaaaaaaaa aaacaaacaa aaaaaaaaac tgagatactg gccgggcgcg gtggctcgtg    18720
cctgtaatcc cagcactttg gaaggccgag gcggtggat cacgaggtca ggagatcgag    18780
accgtcctgc ctaacatggg gaaaccctgt ctctactaaa aatacaaaaa attagccagg    18840
cgtggtggcg ggcgcctgta atcccagcta cttgggaggc tgaggcagga gaatggcgtg    18900
aacccgggag gcagagcttg cagtgagcgg agatggtgcc actgcactcc agcctgctgg    18960
gcgacagagc gagactccgt ctcaaacaaa caaacaaaca aacaaaaaaa ctgagatact    19020
aaagtcttaa tattttctgt ttttatgtat ttatttttg agatgggatc ttgctgtatt    19080
gcccaggttg gagtacagta ttgtgatcat ggcttattgc agcctttaac tcctgggttc    19140
aagtgatcct cccacctcag cctcctgagt agctgggacc acaggcacat gcaacatcac    19200
accctgcagt tctttttttt ttttgagac accgtctcgc tttgtcaccc aggctgcagt    19260
gcgtggtgca atttctgctc actctaacct ccacctcccg agttcaagca gttctgcctc    19320
agcctcctga gtagcttggg accacatgtg tgtgccatca tgcctggtta attttttgta    19380
tttttagtag tgacagggtc ttaccatgtt gcccaggttg gtctcaaact cctgagctca    19440
agtgatctgc ccgccttcgc ctcccaaagt gtctgcgccc tacaatttaa aaaaattttt    19500
gtagagacag tctcactgtt acccgggctg gttttgaact tctgccctca gtactcctc     19560 ttgccttggc ctcccaaagt attgaaatta aggccatgag gcagcacacc cagcctaaat    19620
tcttcttatg ttctgttctt ggcacatagt agatgttcaa caatgtagag tcaaacgcat    19680
ttggagttgg aatggctctg gtgttttttt tttttttta aaccagaaac acgtgcagtt    19740
tattgaatgc cattgtagaa aagtgtgtga ggataaacgg ctgatagaga acttggctct    19800
gggggcaggg cgaggaatgg agggtggatg gagtacatgg gaatcagatc acgggcagag    19860
ctcctggcct agataatgcc tcctgatctg ttgatagact tgaaagatca acactgggat    19920
gatgctgagc agaatggtcg taatgatgcg cacaatcagg gcccagatgt tcaggcactt    19980
ggcggtaaag gcataggcct gggccctgat caggtcgcca accatcttct tgtccctaga    20040
cttcacggag taggccaatg ctatgaagcc caggcagcag gagttcatga agtgggtgtt    20100
gaacagggac cagacgacat ggtcgggcac ggagttctcg ctgtgatgg ggatcacggt     20160
```

```
ggacattggg ggagcagggt tgtggggtgc ccccagcaca gccacctctt gctcctcctt   20220
gagcatctca tagttagggg gatggccgat gttggcagga gtgaagaggt ttggacattg   20280
tggttcatgg tgtccaggga agaccagctg tggtcgggtt gctggggtgg ttctcagtgg   20340
gcccctccct ttccctggta gtttggattt ctctggctct ggtggttttt tagtactcat   20400
tctatttacg ggtgaagaaa ttgagaccaa gagggttatt taccagagta tctcatcatt   20460
ggctgcataa ctggcattag aatctgatgt acttttattt ctaatacatt tctttttttt   20520
tttttttttt tgagatggag tctcgctctg ttgccgagcc tagagtgcag tggggcaatc   20580
ttggctcctt gcaacctcca cctcctgggt tcaagctatt cctgtctcag cctcccaagt   20640
agctgggact acaggcacct gccaccacag ccggctaggt tttgtatttt agtagagatg   20700
gggtagcacc atgttggcca ggctggtctc gaactcatga cctcaggtga tccacctgcc   20760
tcggcctccc agtgctggga ttataggcat gagccaccat gcctggcctt tctttgtcgt   20820
ttcctttctt tctcttcatc cctcctctcc ttttttcccc tccccgctgc ctcctcctgt   20880
cttcccttct ttccttcctt tctctccttt ttattttttc ctttctttt ctttctctgt    20940 ctctcccaac ccttcctctc tccctccctc cctcccttc tctctccccc cctccctccc    21000
cttctctctc ccctcccct tttgttccta agagacaggg tctccttatg ttgctgaggc   21060
tgaccttgaa ctcctgagcc cagatgattc tgcctcctta gtagctggga ctacacccac   21120
ctcccgttcc gttgtcatct ttttttttt tttcttttt ggagacagaa tcttcctctg     21180
ttgctcaggg tggagtgtag tggcacgatc atagcttact gtaactgtgt aacctcgaat   21240
tcttgggctc aagcaatcat cccatcatcc cacctcagct tgctgagtac ctggggctac   21300
aggtgtgtac caccatgtcc ggctaattac ttttcttatt tttaatttt cggagatagg    21360 atcttgctct gttgcccagg ctggtgtcaa actcctgggc tcaagtgaaa ctcttgcctt   21420
ggcctcccaa agtgttggga ggattacag gcatgagcca ctgcacccag cctcctcttt     21480
cttcccattt aactcctaac cacaccgaac tttctgtctg cagagaggag cattggtcag   21540
cagttcacaa aatggctagg tgtgatggcg tgcacccata gtcccagcta cttggggagc   21600
tgaggtggga ggatcgctgg agcccaggag ttcaaggccc tgggcaacac agcaagacct   21660
tatctctggc tgggcccagt ggctcacgcc tgtaatccca gcactttggg aggctgaggt   21720
gggtggatca cctgaggtca ggagttcgag accagcctgg ccaacatggt gagaccctgt   21780
gtctactaaa agtacaaaaa ttagccaggc acggtggcgc gctcctgtaa tcccagctac   21840 tcggggggc tgagacagga gaatcacttg aacccaggag gaggaggttg cagtgaacca    21900
agaacacgcc actgcactcc agcctgggtg acatagtgag actcttatct caaaaaaaaa   21960 aaaaaaggt cgtctgtact attgcatgtt agtagtttct ttctgcttat tgttgagtag    22020
tagtctattg tatgcatgta ccagtttgtt catctagtgg tggacattga gttagcaggt   22080
tttggctatt aaaaataaag ctggaggccg ggtgcgatgt ctcacgcctg taatcccagc   22140
attttggaag gccgaggcag gcggatcacc taaggttggg agtttgagac cagcctgacc   22200
aacatggaga acccccatct ctactaaaaa tacaaaatta gccaggcgtg gtggcgcatg   22260
cctgtaatcc tagctactca ggaggctgag gcaggagaat cgcttgaacc cgggaggcag   22320
aggttgtggt gagccaagat tgcaccattg cactccagcc tgggcatcaa gagtgaaact   22380
ccgtctcaaa aaaataaata aataaagctg tatgaatat ttatgtacag gttttgtgtg    22440
aacatatgat tttatttctc ttggttggaa tgcatagaaa tgagattgct gggttttgtg   22500
gcaagtgttt attttttccag ggtacatata atcctgtgag tgtttattta atttttaaaag  22560
```

```
taattgctaa actgtttgct aaagtgactg ctatattttc tttccctagc agtgtatgaa    22620 ttttttttg aggcagggtc ttgctctgtc acccagggtg gagtgcagtg gtgcgatatt    22680
gtctgactgc aacattgacc tcctgggctc aagtgatcct cctgcctcag cctcctggct    22740
gggaccacag gcatgtacca ccacacctgg tagtttgctt tgattttag tagagaagag     22800 gtctcactat gttgccctgg gtggtgttga actcctgggc tcaagtgatt catctacctc    22860
agcctcccaa agtgctggga ttatagatat gagcccctgt gcctggcctc attgtggttt    22920
taatttgcat ttccctaatg cccagtgata ttgagcattt tttcatgtgt ttatttgaca    22980
ttcataccat ctttggtgat gagaaactat gtttatgcat tgcttaatga tggggatgtg    23040
ttttgagaaa tttttttcggt gatcttatca ttgtacaaat atagagttta cttacacaag   23100
cctagatggt atacctacta gacacatagg ctgtcgtaca gagtattact cttaggctac    23160
aaatctgtat agcatgttgc ggtactgaac actgttggca gatgtaacat aatgttaagt    23220
atttgtgaat ctaaacatat ctaaacatag aaaaggtgag taaaaataca gcgtaaaaga    23280
taaaagtggt atatctgaat aggtcactta ccatgaatgg agcttgcagg acaggaagtt    23340
gcttgggatg agtcatttat cagtggtgtg tgaatgtgca ggcctaggac attactgtat    23400
gctactgtag acaaacactg aacagttagg atacactaaa ttgataaata tctttcttat    23460 tttgttttt gagatggagt ctcgctctat cgcccaggct ggagtgtagt ggcgtgatgt     23520
tggctcactg cagtctctgc cttctgggtt caagcgattc tcctgcctca acctcctgaa    23580
tagctgggat tacaggtgcg tgccaccaca cctggctaat ttttgtattt ttagtagaga    23640
cgggggtttc accatgttgg ccaggctggt ctcgaactcc tgacctcagg tgatccaccc    23700
gccgtggcct cccaaagtgc tgggattaca gatgtgagcc accgcacctg gccagagatg    23760
aggtcttgct gtattgccca gggcgttgaa ctcctgggct ccagcaatcc tcccacctca    23820
gcttcccacg tagctgggac tgtgggtgca cgccatcatg cctagccgtt ttgtgaactg    23880
ttgaccaatg ctcttttctg cagacagaaa gttcactgtg gttaggagtt aagactttta    23940
acctctgacc tcaagtgatc tgcccacctt gacctcccaa agtgctggga ttacaggtgt    24000
gagccatcac gcctggtcaa aaatatcttt ctttaagagt aaatttacct taacttactg    24060
gttgatcatt gtatataggt ctgttgttaa ttgaaacatg cgggccgggc ccggtggctc    24120
atgcctgtaa tcccagcact ttgggaggcc gaggcgggtg gatcacaagg tcaggagatc    24180
gagaccatcc tggctaacac ggtgaaaccc cgtctctact aaaaatacta aaaattaacc    24240
gggtgtggtg gcgggcgcct gtaatcccag ctactcggga ggctgaggca ggagaatggc    24300
gtgaacccgg gaggcggagc ttgcagtgag ccgagatcgt gccactgcac tccagcctgg    24360
gcaacagagc gagactctgt ctcaaaataa ataaataaat aaataaataa ttgaaacatg    24420
cggtgcatgt gtttatttgc gatctgactt gtttggaaat atttgcatta tcttccttct    24480
agatttagag catcttgaca gtaggaacaa gtgtttgta caactttgta tgcttagtaa     24540
gttatcaatt aacttgtcgt ggccaggcgc agtggctcac gactgtaatc ccagcacttt    24600
gggaggccga ggcgggcaga tcacctgagg tcaggagttc gagaccagcg tggccaacgt    24660
ggtgaaaccc tgggtttgtt tgtttgttta tttatttatt tatttttttgg agacggagtc   24720 tcgctctgtc gcccaggctg gagtgcagtg gcgtgatctc ggctcactgc aacctccgac    24780
tcccaggttc atgccattct cctgcctcag cctcccaagt agctgggact acaggagccc    24840
gccaccatgc ctggctaatt ttttattttt tagtagagat ggggtttcgc cgtgttatct    24900
```

```
gggatggtct cgaactcctg actttgtgat ccgcccgcct cggcctccca aagttctggg   24960
attacaggcg tgagccacca cacctggcct accctgtgtt tattacaaat acacaaattg   25020
gccatttgtg cgtggctcat ctacagtctc agtgactcag aaggctgagg caggagaatc   25080
tcttgaaccc gggaggcaga ggttgcagtg agcagagatc gtgccactgt acttcagcct   25140
gggtgacaga gtgagactgt gtctcaaaat aataataata atttgttgaa tatgtgactg   25200
ttggtttaat ttttattttt atgagatgga gtctcactct gttgcccagg ttggagtaca   25260
gtggcgtgca gtggcgcaat cttagctcac tgcaacctcc gcctcctgtg ttcaggtgat   25320
tcagcctccc aagtacctga gactacagac gtgcactacc gtgcctgact aattttttgta   25380 tttttagtag aaatggggtt tcaccatgtt ggtcagcctg gtctcaaact cctattctca   25440
agtgatccgc ctacctcgac cttccaaagt ggcggaatta taggtgtgag ccgtggtgcc   25500
cggccagact attggtttgg tttggtgtga tgttatgtta tgttatgtta tgttatgtta   25560
tgttatgtta tgttatgtta ttttaagaca gagtttgtct cttgtcgccc aggctggagt   25620
gcagcggcat gatctcggct tactgcaacc tccgcctccc aggttcaagt gattctcctg   25680
tcttagcctc ccaagtagct gggattacag gcgcccacca ccgtgcctgg ctaattttg   25740 tattttagt agagacaggg tttcaccatc ttggccaggc tgttctgaa ctcctgacct   25800 catgatccac ccgccttggc ctcccaaagt gctgggatta caggcgtgag ccactgcgcc   25860
tggctgacta ttggttttat tattaagcag tagtagttga ccctgtcatg tagaaagcat   25920
ggcatttata ggcataccac gtttaatttc ctccccttt tttatttttg gagtacctcc   25980
tgcttgtgag gcttgggaat acagtagtga ataagccaga tgaggtctct ctcttttgg   26040 agcttatgtg gtagtataga ctaggcagaa agttctcatt gcccctgcca ccttatggca   26100
ttgaggtgtt tgagatgctg atgtttactt ctgtctcata aaatcttgaa aggagttctt   26160
ttagatgaag aggaaaacaa aatcagaaga atgggcctgg gtcatgtctg taaacctccc   26220
cacgtcatgg ggaggctgaa atgggaaggg ccaggagttc aagaccaggc tgagaaacat   26280
aacaagaccc catctctaca aaaaatattt tttaattaat gggggatggc agcacacacc   26340
tgtagtcgca gctactacga ggctgaagcg agaggattgc ttgagctcag gagttaaaga   26400
ttgcaggagc tatgatcaca gcactgcgct ccagcccctc ttatcagcag tctggtatgt   26460
tgctaagggt cttgttcttt ttagtgcttc agggacagcc actggctatg cccagaaata   26520
agtatgtttg agaagctttc tgacctcagc ttgaaaaatt gattagggtc ataattaaaa   26580
agggagggaa acaggattga gtgaaccgga cgctaccgtg agtttattct cccagggcat   26640
acataatctc atgtgattac cacatagccc tgttagataa tctgttatcc tgtcctcatt   26700
ttacccatga ggaaatgaag gcccagagag gttaaatgac ctattcaaat tcactcagaa   26760
ggtggcagag atgagttact atcattgtat tttggatctc tggaaagaaa gaaaactagt   26820
gatggtatta aaaaatgtta ttaatagttt cttttaatca accaggaact tgagtcacta   26880
gcttctctgg gtgaaggact atacttcaac agtatgaaaa acgaaaaga aaatgaggaa   26940 ttttggctgg gcacagtggc tcacacctgt aattctagca cttgggaag ccaagggagg   27000 agggtcgctt gagctcagga attcaagatc agcctaggca acatagtgag gccccatctc   27060
tacaaaaata aattagctgg gcatggtggt gcatgcgtat agtctcagct acttgggagg   27120
ctgactcagg agggtcactt aaacccagga attggaggtt gcagtgagct atgattcgc   27180 cactgtatac catcccaggc gacagagtga gaccctatcc ccccaccgcc aaaaaaaaga   27240 aagaaaatg aggaatttac atttgtgaca gatacggaat tcagggaatt tagttgttca   27300
```

```
tagtctataa atgctataag aagtctccat accttttttt tttttttttt ttttttttgg   27360
agacagagtc ttgctctgtc gcccaggctg gagtgcagtg gtgcgatctt ggctcactac   27420
aagctctgcc tctcgggttc acgccattct cctgcctcca cctcccgagt agctgggact   27480
acaggtgccc gccaccacgc ccggctaatt ttttttgtatt tttggtagag atgaggtttc   27540
actgtgttag ccacagatcc cgacctcatg atctgtctgc ctcagcctcc caaagtgctg   27600
ggattgcagg cttgaatcac cgcacccggc cggaagtctc catacttttt aacccaatct   27660
aaaatggtaa ggaaatatat aagaatgtct atttattatt aaatttttc tatataaaac    27720 atttcagaaa ataagactga gcatttctga gccaagtggt agtagtggcc attttttctg   27780
gaaaaaaaaa aaaaagaaa gaaaaaacac atttagctat ctatgatgtg aaaagatgaa    27840
catttatttt aggtaataaa tgttatgtca taaaatacca tttattgtgt gcctattagg   27900
tttcaggaga gctgtgccaa gagcattact tgtatatctt ttaagcctta caacagccca   27960
gcctgtcagg ctggtagtgc catatctgtt ttacagatga ggaagtgatg gattggagaa   28020
attaaggaaa ttgcctttag gtcaaagaga taggaagtga caaagctgag attttttaacc  28080 ttgtgagatt tcaaagtctt tgcttttttaa taactgttcc attgcttcta atatagagat   28140
atgacaaaaa caagtaaaaa tcagtgaaga aggctgggag cagtcgctta tgcctgtaat   28200
cccagcagtt tgggaggccg aggcgtgtgg atcgcctgag gtcaggaatt tgagaccagc   28260
ctggccaaca tgacaaaact ccgtctctac taaaaataca aaaagttag ccaggcgtgg    28320 tgacaagcac ctgtaatccc agctactcag taggctgagg caaggagaat cgcttgaacc   28380
tgggaggtgg aggttgcagt gagctgagat cgctccattg cactccagcg taggcaacaa   28440
agcaagactc cgtctcaaaa aataaataaa taaataaata aaataataa caataatgaa    28500 gaaacaatc cggtgattat tgtcagcaat aaaatttctt caatcaacca tgctttagtc    28560
ctggcagttc tctatcagtg agtttcaatc aaaaagtttg tttataattt tttttttttt   28620
aaaattttga aatttggaaa caacatcata aatgatggtt agttttctgc agctccctat   28680
tttggcagat agtctgttgt tactcataat taatttgaac taaaaagtag tgttgtacga   28740
tatcatgggc tgtgaatgtg tttgtgactt gatctgagaa cccacacacc acttaggatg   28800
cttctgtagg aaaattagag tatggaactc acttgcccac gctttccctg tctcagtcca   28860
tgttggtagg ctgcaaagtc tggggctaga aggacactga acaagacttc agcagtacat   28920
gttagtcttc cagagggaag gaatataata gttgagagaa taattccttt cctctgtgac   28980
tttaggcaaa ttcttggcta tgctgttatt tatttgggcc aaacaatatc aggaggttgt   29040 acatttatt cttaattact gcgatacatt aatttatcc atgggtttaa cctagcctac     29100
cttttgctgt tagacttcaa ctctacttgt gttgggttac ccctctgctt aaaaatcacc   29160
ctattcccaa gcctgaggga gtctaccttc aaagctttct atgacctaat ccaaggcctg   29220
tcaaacttcg taagggcca gatagtaaat ttgtttttttt ttttgagat ggagttttgc     29280 tcttgtcacc caggctggag tgcaatggtg ccatcttggc tcactgcaac ctctgcctcc   29340
caggttcaag tgattctcct gcctcagcct ctcaagtagc tggggttata ggcatgtgcc   29400
accacgctcg gctaatttct ttgtatttag tagagatggg gtttcacca ttttggtcag    29460 gctggtctcg aactcctgac ctcaggtgat ccacctgctg cggcctccca aagtgctggg   29520
attaccagtg tgaccaccg tgcccagccc gatagtaaat attttaggct ttgcagtcca    29580
tatacagtcc catttttttg tgtatgtttg cacgttttct ttacatattt taaaagcccc   29640
```

```
tttttttttt tttttgagac agagtcttgc tgtgttgctc aggctggagt gcagtggtgc   29700
aatcttggct cactgcaacc tctgcctcct gggttcaggc gattctcctg tctcagcttc   29760
ccgagtaact gggattacag gcacatgctg ccacgcccag ctaattttg tatttttagt    29820 aaagatgggg tttcgccaca ttggccaggc tggtctcctg atctcaggtg atctgcccac   29880
ctctgcctcc caaagtgctg ggattacagg tgtgagccac cgtgcctgac ctaaaagctc   29940
tttacagtgt aaaaaatatt ctgagcttta agccatgtga aataggcca tgggcatttg     30000 ctgacccta atagaactcc attttacctt tctgatcatg tttcccatta actcttcaaa     30060
aatatgacct ccatttaaat caagatggtc tccttcctca ctgcttgtgg aggtccagtg    30120
cccagtgtct gcctcttgct tgctcctcca tcattgttct gccattcgag atcctcatac    30180 ttaccctta agatctagcc caatttttcc atgaaactaa ttctaataat taaaaacttc    30240
ctgtagaact taactttgtc tagtacaagt tagctttctt attcagtagt agcttactat   30300
aaattacaag aataaaaaga ttaccatttt ccctcacact gttttgtgga gaatgcctaa   30360
agttactttt tcttttaca ggtcagtatt cctatttggc atcctaatcc cctttcccaa    30420
atctgaattt tgggatttga agcttgcatt tgagattatg atttgtcttc cttgttgtac   30480
acaggagcag ggactttaca attagtattc gcatccctgc tccttcatac ttcgtgatgt   30540
aaggcaagtt attttcactt atgcttaagt ttcttcccct gtaaaagggg gatggaagag   30600
gattaaatga attaaacatg taacacgctt aaagcaatgc ctggcaagta ataagtgctc   30660
agtaactttt agctgttctt attagcatgt ttggaaacca gtagaaacta caccagcaag   30720
ttaaggttga aaagtggtat tgatgggctt ggggtagtac agtatgaatg ctacagtttt   30780
agcgtttcat taagtttgta tattcattaa ttcattacac atttgatgct gtcagactag   30840
gacagagaca aagatgaatg aaacattatc tctgcttcca ggttacccag tgtagtagag   30900
aaggcaggca tgcagatagt ttaaattggt agcactggga ggggactgcc atgggtgggc   30960
agtgaagaaa aagggcttca aaataatgag agttgagatg gatcttcaag gaagataagc   31020
agttttcagt aaggccatga agagaggagg aagttccagg cgggaagagt ttgtgctaaa   31080
gtacagggat tgctatacac atggtgtatg tagaaaaaat ttggttcaca gtgtgataga   31140
agaattggag ggggtcctca ctgaaagtaa ggaaacacat ttggaagaat atgtttcagt   31200
tagaaaatga aatgagctta aagtaaacgc taataaggtt tttaaaatgt aaaatttcaa   31260
cgtatttaga aagagaacag ctggatgaat cttatgtacc tgtcactcag ctttagcagt   31320
tatcagtaaa tggccaacgt tgtttcagct atactcccct ctcctccact gatagtcttt   31380 tgaagggaa tacaattgtt ttgtggcctc cagaaaggga taagtttatg agcaacgggt     31440
agatcgttgg gagagacttg agtttcctgt caggaagcat tcttggtgca taagtcagag   31500
gtgatatgaa tgccgtggaa gggggtggct tactgtctgg agaactcgag aagatgggaa   31560
tgggcactgt ccagtattgt ggctacttcc acacatggtt cttaaatt aaaattatgt     31620 tgattaaaat ttaaatattt cagttcctca gccatactaa tcgtatttca agtgcttagc   31680
tgccacatgt gcctaatggc tgcaatattg gacagcatga cataggacat cttcatcatt   31740
gtacaaagtt ctcttggaca gcatgggact agagccctaa gatcctttc tacctgagtt    31800 gtttggattt tttggtgtgt ctaggttgga tctagttgtt catggcttca tgaccaagcc   31860
ttttatccct ttctctagag ggactcaagg ggtaaaggca ctgaagggt aaaacttcat    31920 atgaagagtg tggtggtggt ggtggtgttt taagacaggg tctcgctctg tcactcaggc   31980
tggagtccag tggcatgatc ctggctcact gcagcctcga cttcctgggc ttaagtgatc   32040
```

```
ctcccacctc agctcccaag taactggaac tgtaggcatg agccaccaca cctgcctaat    32100
ttttaaaact ttctgtagag acgagatttc gccatgttgt ccaggctggt ctcaaattcc    32160
tggactcacc ttggcctccc agagtgctgg gattgcaggt gtgggccact gcgactggcc    32220
ttttttttct cctttactac tctagtgtat gctggaatat gaggaaataa ttatattagc    32280
tagcagttat taaacactta ataacatacc aggcactgtt ttaagctatg cgatctgtat    32340
ggaatattac ttaatttcca caaccttatg aaaagatact atttttttc ttttgagaag    32400 gtactatttt catcttcatt tcatagatgt tgaaattgaa acacagagag ctgaagtcac    32460
aggattaagg ccacagagct gagaagtgat ggagccggaa tttgaaccca agcaattaat    32520
gctgatatta gttcttgtgt gaatggtaat tgttttgaaa caatgatcct agatgattat    32580
atgaccggat taatctggca gttgttctgt gtgaatttag agttgccttc ccacctcagt    32640
ttcctaaaaa caaacaaaa caaaacaaaa caaaaaaaac tctagcttca ctgtgtttgg    32700
gttgtcatgg cctacccct cttgccacct catttgactc aactttttag ggagaaaata    32760
ttcaatacgt ggtataggat ttcccttct aataataatg taaacaacaa caagaagtct    32820
gaaattggaa gaacaaaatg actcacctaa gtgagttaac cttaagaggt ggaacttgat    32880
ttctagattt tagttaattg tctaactgat gtactaaata ttagttactt aagtattaaa    32940
acgggtagac ataatagttg gggagctgct gtagagggg tagtttgaga aggcttcttt    33000
caggaggtga catttaagtt ggtaactaac aagaaagggg cagccatgtg aatagctgga    33060
gggaagagca ttcttacagt tttactggaa gggggttaga ggtatgtggt acccttatgc    33120
caaagaaaat tagttacttc tatacaacca gtctgattct agaaacctgg atcaatgaaa    33180
tattttgatt atataaaaaa atctgttacc caggtcttgt tgaaatagca ttagaaacta    33240
ctgaaggaca tatagaggag gagtgttgaa aaatggtgat ggatgagcag aatggtgaaa    33300
aataaaaaga catgaagctc tataattata ttgtatggtg acagtaccaa tagagattgc    33360
atgttttttc tccccagttt ttttttttgt tttgttttt gttttgaga cagagtctca    33420 ctgtgtcact caggctggag tgcattgtcg tgatattggc ttactgcaac ctctgcttcc    33480
tgggttcaag cgattctcct gcctcagcct cctgagtagc tgggattaca ggcatgtgcc    33540
accacgcccg gctaatttt gtatttttat ttgagagggg atttcaccat gttggcaagg    33600
ctggtcttga gttcctgacc tcagataatc cacctgcctc agcctcccaa agtgccggga    33660
ttacaggtgt gagccactgc gcccggcctc ccccagttgt tgaaacaata atggaaggta    33720
attttattct tagattattt aatgttttc agttatcagg atgtgttaga ttgtttgtgt    33780
atattgtttt gcttgttaat taagtaacac agtgaataag acagacaaac atacgaaaat    33840
gtacatttat tttatttttt tgagacagtc tgttgcccag gctggagtgc agtggcccaa    33900
tctcggccca ctgcaacctc tgcctcctga gttgaagcga ttctcttgtg tcagcctcat    33960
gagtagctgg ggccatgggt gcacgccacc atacccggct aatttttata tttttagtag    34020 agatgggggtt tcaccatatt ggccaggctg gtctcgaatt cctgacctca ggtgatctgc    34080
ccgccttggt ctcccaaagt gctgggacta caggcatgag ccactgtgcc aggccatttc    34140 attttggaa cgttcttttt ttttttgaa atggggtctc gctctgtctc ccaggctgga    34200
gtgcagtggc tcaatctcag cttactgcaa cctctgcctt ccgggttcaa gtgattctcc    34260
tgcctcagcc tctgagtat ctgggactac aggtgcatgc caccacgcca ggctaatttt    34320
tgtattttta gtagagacgg ggtttcacca tattggtgag gctggtcttg aactcctggc    34380
```

```
ttcgtgatct gcccgcctca acttcgcaaa gtgctgggat tacaagtgtg agccaccacg    34440
cccggcctgt ttctggaata ttcataatct tttgttgtca tttcaacagt gctcacagca    34500
gcttcaccag gtgtagattc catcttaaga aaccactttc tttgcttatc catgagaagc    34560
aacacctcat ctattcaagt tttatcatga gattgcagca attcagttac atcttctgac    34620
cccacttcta attttagttc tcttgctttt ttaccacatc tgcagttact tgctctactg    34680
aagtcctgaa cccctcaaaa tcattcatga gtattagaag caatttcctg gttgggcacg    34740
gtggctcatg cctgtaatcc cagtactttg ggaggccaag gagggcggat cacctgaagt    34800
caggagttca agaccagtct ggcaaacgtg gtgaaacccc gtttctacta aaaatacaaa    34860
aattagcggg gatgtggtgg cgggcgccta taatcccagc tacttgggag actgaggcag    34920
gagaatcgct tgaacctggg aggtggaggt tgcagtgagt tgagattgtg cccttgcact    34980
ccagcctggg caacaggagc gaaactctat cttaaaaaaa aaaaaaaaga aaagcaattt    35040
cctctaaaac tcctgttaat gttgatgttt taacctcctc ccatgctcat ggatggcatt    35100
ctcagtggca tctagaatgg tgaatacttt ttagaaagtt tcaatttat tttgccatca    35160
gagaatggct atgaatggca gtagtagcct tacagaatgt attctttttt ttttttttct    35220
tttttttga gatggagttt ttttgctct tgtcacccag gctggagtgc agtggcatgc    35280
tatctcggct caccgcaacc tccgcctccc gggttcaagc aattctcctg cctcagcctc    35340
ctgagtagct gggattacag gcatgcacca ccatgcccac ctaattttgt attttagta    35400
gaggcggggt ttctccatgt tggtcaggct ggtcttgaac tcccgatctc aggtgatctg    35460
cctgcctcgg ccttccgaag tgttgagatt acaggcgtga gccaccgcgc ccggccgtat    35520
ttcttaaata aaatggctta aacgtcaaaa ttatcccttg atccctgggc tatggactga    35580
ttcttgtgtt agcagttatg aaaacattta tgtccttgta cattcccatc atagcttttt    35640
gtcaatgaga agtaatttt tttttttttt tgagacagaa tctcactctg tttcccagcg    35700
tggagtgcag tggcatgatc tcagctcagt gcatcctaca actctgaggt tcaagcaatt    35760
ctcgtgcctc agcttactga gtagctggga ttacaggcgc ccaccaccac gtctggctaa    35820
tttttgtatt tttagtagag atggggtttc acgatgttgg ccaggctggg ctcgaactcc    35880
tggcttcaag tgatccacct gccttggcct cccaaagtgc tgggattgta ggtgtgagcc    35940
actatgcctg gcctaattgg cctaatttca atattgttat atctcaggga atagagaggc    36000
acgaggagaa agagagacaa gctgactgct ggttcgtgga gtagtcataa cacacaacat    36060
ttattaagat tgctgtctta tatggaccgt ttgtggtgcc ttaaaagaaa tcagggtaac    36120
atcaacgatt actgattaca gattactata acagatacaa taataattgt aaattattat    36180
ttacaattgt aaaatacaat cttttcttta ttatttacaa ttattgtaaa atacaatctg    36240
attacagatt actataacgt atacaataat agtggaaaag tttgaaaata ttgtgagatt    36300
tatgagaatg tgacacaggc gcaaagagag cacatgttac tggaaatacg gcactaatgg    36360
acttgcccga ctcggggttt ccacagacgg tcagcttgtc aaaaatgcag catctgtgaa    36420
tttcaataaa gcaaagcaga ataaaatgag gtatgcatgt attgccatca catgtacact    36480
agtaaaatac gttttttttt tcagtaggtg gatcaacctc aaattttaat ataaagcatt    36540
acttaaagga gaatatgggg acattcatga catttcttat atgtacataa aacttcatga    36600
aaataattta atgctatcca gcagtttatt ttagaagtac tggaggctag catggtgtc    36660
ttatgcctgt aatcccagca ctttgggagg ctgaggtagg aggatcactt gagttcagga    36720
gctggagacc agcttgggca atatagtgcg accccatctc tacaaaagag aaaagaagta    36780
```

```
ctggagtgtt gcagctctta cagaatttgt ctagcaggtt ttccagtctt taccagaaat   36840
gcccccatgc agaagtagta aatactgatt catgtaaaat aataaacaac tttatctttc   36900
agttttaaaa agacagggtc ttgtaacgtt gcccagactg gcctttaatt cctgggctca   36960
agcgatcctc tcacctgagc cttttgagta gctgagacta caggctgcac ctctgcacct   37020
ggctctgctt gatttttaat tgttgtattg ctgttgcagc tatgttttt tttttcttca    37080 gtgtgaggat gggcaaactt tttatgtaaa gtctcaggta ataagtattt taggctctag   37140
ggccatatag cttctctgtt gcatatcctt ttttttttt tccatttccc ctcaaattcc    37200
ttttaccata agcaactctt gaggaacata aaaatcattc ttagcccaga agccagacca   37260
aaacaggttg tgggctgtag tgtcctgacc cctgatttaa agattgatag ctttgaaatg   37320
gaaagtttta actttctttt tttttctttc ccttgttctg attgggctgt taattcatta   37380
ggtatttact cagtgtgtat catatgaggc atgattcctc tgctaatttt ggtagtggta   37440
gaaagatact tttgccaagc ttggttgtta ggttttcatt tgtccaagag ttcctgacca   37500
agtgtgaatg gatgttgaaa tcaaggtgtt tctttggcca cacaatgtgc ctttgggggc   37560
tatatctatg tgcttctggt accttctttt aattttcaca aagacactgc ttgccgacca   37620
cactgttttg tctaatgtgg ggctatgacc ccctggaaga ggcatcattt tctgattttc   37680
acagaagcat aatatggtca ggtgatggtc ctgagtagtg ggtatatgac agatacacta   37740
gtaattataa tacagatcta aactggagag ttgaaaacag catcgtatat ttgattgaga   37800
taatcgaagg aagacttcct gaaaagatgg catttgagtt tcaaggctga gtaggattaa   37860
gtattattat ttaaaaaatg ccttggacaa tgcattaaat agagttaaca aatcacatca   37920
cttatagtct ccaattaaaa acattttact taaacataat tttagacttt tagaaaaatt   37980
gcaaagatat tataaagaat tctcctatat atctcacctg tattcttcaa gtaacatttt   38040
accatattca ccttaacatt ttctctgtat tggtaattgt atatgtaaga tttaatataa   38100
aataaaaatt cttattaaac atatgagaga catgatgcct ctttagccct aaatacttca   38160
acttgtatgt actaataaca agggcattct atttcaaaac cacagtacag ttgtcaaaat   38220
aaggaaatta ataattgtgt caaactgtta ttctgtttat agaccttcta atgtccttta   38280
aaacaatcaa caaatcaaca ttttctggt caagaaccag taaatatgta tattctacat    38340
atatatatac acatatatat acacacatat attctacata tatatgtgga atatacgtat   38400
ttactccctc tgtccaagaa ccaatccagg attgttacct tcggttatca tgtatctttg   38460
gtctccttta atccaaagca gtttctttgt cttttatgac ttgacacttt tgaagattac   38520
aggttatttt gtagactgtc cctcaactag ggtttatctg aggtttcctt atgattagat   38580
tcagatattt atttttggca ggaatacaac agaaatgatt tgtgtgtttt tctcattgca   38640
tgatatcaga aagtgcattg tatatattta tcccattact ggggttgtta actttgatca   38700
cttggttaga gttgtgtcta ctaagtttct tcactataaa gttattttc acttggtcat    38760 ttcatcagta tcttgtgggg agttactttg tggttatata aatactctgt ttctactttc   38820
ccttactata tttagcttct gtggacactt ttgcctgaaa cagttattta ctatggtgtt   38880
accaagtagt gatgcccttt tcttccatca ttctgtctac attttttttt tttttttttt   38940 tttttgaga tggagtttcg ctcttattgc ccaggctgga gtgcggtggc ctgatcttgg   39000
ctcactgcaa cctctgcctc ccgggttcaa gcagttctcc tgcgtcagcc tcccgagtag   39060
ctgggattac agacatgcgc caccactcct ggctaatttt gtatgttcag tagagacagg   39120
```

| | |
|---|---|
| attttttccat gttggtcagg ctggtctcca actcccgacc tcaggtgatc cacccacctc | 39180 |
| agcctcccag agtgctagga ttacaggcgt gagctgccac accaggcctt cttttttctct | 39240 |
| tttaagagat agagtcctgc tttgtcacca aggctggagt gcagtggcat gatgatagtt | 39300 |
| cactgcagcc tcaaactcct gggctcaagt gaacctccca tctgtagctg ggactacagg | 39360 |
| cacctgcata acacctgact gttttttaaa actatttag atgggggtc ttgcgaagtt | 39420 |
| gctcaggatg gtcttgaact ccgggtctta agtggtcctt ctgcctcagc ctctggatta | 39480 |
| gttggcatta caggcatgag ccattgtacc tggcaagtgc atattttctt ttttttttt | 39540 |
| taaggtggag tctcgaggcc gggcgcagtg gctcacacct gtaatcccag cactttggaa | 39600 |
| ggccgaggtg ggtggatcaa gaggtcagga gatcgagacc atcctggcta acatggtgaa | 39660 |
| accctgtctc tactaaaaat acaaaaaatt aactgggcat ggtggcacac gcctgtagtc | 39720 |
| ccagctactc gggaggctga ggcaggagaa ttgcttgaac ccaggaggtg gaggttgcag | 39780 |
| tgagtcaaga tcatgccact gcactccagc ctgagcgaca gaggtagact ctgtctcaaa | 39840 |
| aaaaacagaa agacggagtc ttgctctgtc acccaggctg cattgcagtg catgaactc | 39900 |
| cgcctcctga gttcaagcaa ttcttgtgcc tcagcctccc aagtagctgg gattacagac | 39960 |
| atgtgccacc acacgtggct aatttttata gttttagtag aggtggagtt tcaccatgtt | 40020 |
| ggctaggctg gtcttgaact cctgacttca ggtgatccac ccgccttggc ctcttgaagt | 40080 |
| ggtgggatta tgagtgtgag ccactgtgcc cagccaagtg agtatttgct tatgtagtat | 40140 |
| tttaatttta tgatttttttt ttcttttgaga cggaggtttg ctcttgttgc ccaagctgga | 40200 |
| gtacagtggt gccatctcgg ctcactgcag cctccacctc ctgggttcaa gccgttctcc | 40260 |
| tccctcagcc acctcctcct gaatagttgg gattataggc gcctgccacc atgcctggct | 40320 |
| aatttttgt atatctagta gtgatggagt ttgagcatgt tgccaggctg gtcttgaacc | 40380 |
| tctgacctca ggtgatccac ctgccttggc ctcccaaagt gctgggatta aggcatgagc | 40440 |
| caccatgccc ggccagagac tgttcattta tttttttttt ttgaggcgga gtctcgctgt | 40500 |
| attgcccagg ctggagtgca gtggcacaat ctcggctcac tgcaagctcc gcctcccaag | 40560 |
| ttcacaccat tgtcctgcct tagcctcctg agtagctggg actacaggtg cctgccacca | 40620 |
| cgcctggcta atttttgtttt tgtattttta gtagagatgg ggtttcagcc cgccttggcc | 40680 |
| tcctggagtg ctgggattac aggcgtgagt cagggcgcct ggccaatcat accttctttt | 40740 |
| actgcattaa ttatggtttt ctttcgttct taaaacatgt ttatagtgac cacttttgaa | 40800 |
| attcttatta agtcagacat ctggttatac aagcaatttc tattgcctac ttcttttttcc | 40860 |
| agtgggtggg gttatacttt cctgtgtctt agcttgtcgt tttttttttt gttgttgaaa | 40920 |
| actggacatt ttaagtaatg tagtaactct ggatacctca ttagcctatg gttgggggtg | 40980 |
| gtggttgtta ctgttatttg cttatttgtc taatgactgg ctgaatgatt ttagtgttct | 41040 |
| atccttcttc cctccctgta cagtgtgaca cgtctgatgc tagttttctt gggatgcagc | 41100 |
| cttgggtatg cctaccatca ctctagaatc acagtgattt tggcatggct ttgtctcttt | 41160 |
| tcctgactgt acccagctgt taagctacac taattactag gtgatgctgt gtagtcattt | 41220 |
| cttggtgtcc ttgggggatt ggtcccagga ccccccgtt ggatataaaa atttatggat | 41280 |
| gctctagtcc ctcataaaat ggcacagtat ttgcatatac cggtgcacat cctcctgtat | 41340 |
| gctttgtcat ttctagatta cttataaatac ctaatatggt gtaaacacta ggtaaatagt | 41400 |
| tgttatatat ttttattttg tcttattttt attgtattta ttttaagtg tttttaatct | 41460 |
| cgagtgattg aatctgagga tgtgaaatct gcagatatgg agggcctgca ttgttttccg | 41520 |

```
tggagctttg ggcctaaact gctccacaga ctgatctgat caaatttgcg cttctttgaa   41580
gggatagttt ctgagatcag tgtttgaaat ttgttccaat ccacagagga gtcctcccag   41640
ctctctttcc ctagttctgg ccaccaaact agacaactac aatttagcac ttatctccaa   41700
tgattctcct cctaccaagt gcctttgaaa gcatcattaa ctctttcata ccttgttgca   41760
aatgaaattt ctttgggaag agattgtgag ttttttttct cctaaattat ggtgcaatat   41820
aagtaatata ccattttaac aattttaagt gtattaagtg tttttttttt ttgtagtttt   41880 ttttttttg ttttttgaga tagtcttgct ctgtcgccca ggctggagtg cagtggcacg    41940
atctcggctc actggaacct ccacttcccg ggttcaagtg attctctggt ctcagcctcc   42000
ccaaatatct gggattacag gtgtgcacca ccacgcctgg ctaattttc tattttagt    42060 agaaacgggg tttcaccata ttggtcaggc tggtcttgaa cttctgagct cgtgatccac   42120
ccacctcggc ctcccaaagt gctgggatta caggccttag ccaccacacc tggcctatgc   42180
attgctttta tatgtatttt aaaattcata agttctcctc ctatgatgtt tttgtcccat   42240
gtgatttatt tgttaaaccg tcatctttgg ccgggcgtgg tagctcacgc ctgtaatccc   42300
agcactttgg gaggctgagg tgggtggatc acaaggttaa gagatcaaga ccatcctggc   42360
caacatggtg aaaccccgtc tctactaaga atacaaaaat tatctgggca tggtgacgcg   42420
tacctgtagt cctagctacc tgggaggcgg aggttgcagt gagccaagat cgtgccactg   42480
cactccagcc tggcgacaga gtgagactct gtctcagaaa aaaaaaaaa caaaaactg    42540 tcattttta tgttgcattt actgcattct ggatttaaac tgtgaggaac ctcatggtat    42600
cagttaatat attcttccat cttaatgttt ctcgtaaact ggtagatctg taaacttgat   42660
taggtctatc ctattgtatc acatcagaag cagaaggtgc ttttttttt ttttaaggga    42720 aattgtgtga aagtagacag aatggtaaag tgaaccctg cacacctatc acccagcttt    42780
aatagttatc agctcatacc attcttgttt gatttacaac cccattcatt tctcccttct   42840
gtattattat tatttagtta attattttt gagacagggt tttgctctgt caccaatgct    42900
ggagtgcagt ggcataatca cagctcactg ctgtcttgac ctcctgggct caagtgatcc   42960
tcccacctca ccctaccaag tagcggggac acaggcgtg tgccaccatg cctggctagt    43020
tttttatttt ttgtagaaac aggtttttgc tttgttgccc agactgatct caaactccgg   43080
cactcaagtg atcctcctgc ctcagcctcc taaagtgctg ggattacaag catgagctac   43140
cacattcagc atgtaaattt ctttatatta atttgactgg catttaagt cacacttgaa    43200 tttcatttt ggcaactatt aaaagcatag agtcctggat attagtgttt tgttaaacct    43260
gatctatcta atcataaata tacttaggtc taaaatatgc tcttggcctt tgtttattgc   43320
ggttcagtat ttgttactat attaaatagt aaaatatttg gtttgagata ctaatgaaaa   43380
gattaaaagt aaagcataac ttgaatggat acaaaaagaa acaagaattt agacttcagt   43440
ggatttcaga gaatactgct tcgatatgct aacattcctg ttgggtgtcc aaccgtgtca   43500
tagatcagtg gaaattagtg gtttctgcac tttactgtac tgtttttta tatgataata   43560 ttttcctggt tgaatgattc gttcttttga gtaaactcca tggtcaaaca attacttttt   43620
attagtcaaa gatgtaacca cataatcact aaaaagaaca gtgtgactta tttaaagggg   43680
attatgtttt taagtctttt atatagcttt gtagggaggc catatgagtt taaggacagt   43740
tcgtggcatt tgttcaaggt tttgtaactt ggcatctcag cagccaccag gataccagat   43800
catcgttcta agtaagattt aggcatttta gccttcatgt acagactata agtacacccc   43860
```

```
cccacacccc taccaaaact gtaaattcaa atgatgtttg aaaaagcata gaatttttgt   43920
taggcgaggt agtttattcc ttgtgataca gttccagaga ggcagcataa cctaggaatg   43980
aaaaacttag acgtggaatc agatacacct ggtttaaata ccagctctac tgctcatgaa   44040
ctggatgatt ttggtcaaga tacttgactg ctgaggttca gtttcctcac ctgtaaagta   44100
gaggtgatag attagacatg ttgcatgtga agtacttagt atggtgtctg gttttgtagt   44160
aagatctata aaagataaat tattagtcat attccttaga cttcaggaat ttatctctgt   44220
gccatgtttg aggcaaacag ttacagaatt agaatgttag aaatgaaagg aatcctagat   44280
gtcatttaat tcaagtccat tgttttctgg atgagagaag aaagtgagga aaagtgacag   44340
agttggagac caagctagga ctggcctcag aatgttaaga gtactcttct agggatcgac   44400
cagtcgtgtt actagacttt ttggatctga attgtgcttt tccttgaatg tttttgaattt   44460 tggcttgagt gttgtgatta ttttattaaa atgagattcc agtcctattg tcatgactaa   44520
tgtttatgag aaatataaca tttcacttta atgatgtttt ttaattattc taagggcct   44580 aatctttttc agtggaataa gctttaggtt gtattatatt ctataattca cttgaaaata   44640
gaattcatct ttacttgaca gccaaatttt gtgtactgca tcttttctga gggagagagt   44700
tggcaaggaa aggcacttgt tacaacgatc cacacatata gacgcatatt atttagaaat   44760
gaaagtgctt tgaatgattt agcttatttt cagtttttt ttttctgcag ttgtaatcat   44820
atgacctgtt tttctttctt tttttttttt tgagacagag tcttgctctg tcaccccggc   44880
tggagtacaa tggggcggtc tcagctcact gcaacctcca cctcccaggt tcaggcgatt   44940
cttctgcctc agcctcccta gtagctggga ctacaggcgc atgccaccac acctggctaa   45000 ttttttttatt cttagtagag atggggtttc actgtgttag ccaggatggt ctcgaactcc   45060
tgaccttgtg atctgcccac ctctgcctcc caaagtgctg ggattacagg catgagccac   45120
tgcgcccggc ccatatgacc tgttttcttt tatagatgg gggagaaata tgggaagtga   45180
cttggtgtca gtcatctgtg ttggttaaat caagaatata atccgtgttt tgcttctgaa   45240
tagctcttta taacagtgat tggttacttt gggagtaaag attattattt agagacagag   45300
tcttgctttg tcgcccaggc tagactgcag tggaatgatc gtagcctact gcagcctcag   45360
actcctggac tctggtgatc ctgcctcagc ctcctgagta gctaggacta gaggtgcatg   45420
ccacatgcct ggctataatt attattaatt tacgtttagc attagttttt ttcttccagt   45480
aggctatttt actttatttta tttgattttg atgaagtttg attatttcta gtttgcttcc   45540
ttctatgacc cctacctgtt gtgggtctcc aggcaagcag tgcataggta gagccatcct   45600
taggtagcct ttagacttaa tattaggtga gctctcccca cagatagcct ctcctttatt   45660
tgaatggaat tatattttaa gtttggaaat attttcagc ttatttagcc tgttgaattt   45720
aataaaaata atatttaatc ttttcagagg tcgaaacagt aacaaaggac tgcctcagtc   45780
tacggtgagt aactttaatg ttacttattg ggaaaatta gtagctaaaa catgatctct   45840
aaccacagac caaatgccaa ggcaaaagat tcccttcttt tgaattttgt catagataac   45900
ttgactgttt aagtatgtta ttagcctata tgtgttttt taatgactct gtataaaatg   45960
tacaattact tgttgtatta gtccattctt acactgctaa taaagatata cctaagactg   46020
ggtaatttat aaaggaaaga ggtttaattg actcatgctc tgcattgctg gggaggcctc   46080
aggaaactta caatcatggt ggaaggggaa gcaaacacat ccttcttcac atagcgacag   46140
gagagagaag tgctgagcaa agcagggaaa gccccttata aaaccatcag atctcctgag   46200
aactcactca ctatcatgag agcagcgtag gggaaactgc ccccatgatt cagttatctc   46260
```

```
cacctggtct tgcccttgac acacgagaat tattataatt aaagataaga tttgggtggg    46320
gacacagaac caaaccatat catttgtaaa tagtattttt gtcacgtgta ataacaagaa    46380
caagtcgctt gttctttct aaatgactaa gtgcaaatct aagtgaaaaa cctccaaaag     46440
atacgtagaa caccaagagt ggagtctgca gagttcttta tgcttttat tttgaattaa     46500 tgtgcttttt ttctgctgct ttcattttc cctttggct ttctggtctt aaattttgga     46560
atgttatcaa tgaaattgaa ccggacatga agggcagaaa ctataagtcc cacatgatgg    46620
aagaaataaa tgagaagcta tcacaaattt ttgagacttt gcctttatta gattgtttta    46680
caagaatcag gaagatatac acgtatatgg tagtaatatg gagtagtgtg gttgatcaga    46740
cttaagcact gtcactgatg ctgatatgct gggagaacct agtcagggtt cttctatgaa    46800
ggtatgacct ggcttcctac cccatttatt tatacttcac ccttcttagg gtacatttct    46860
gtgagtttta acaattgcat acaatcagtg taactaccac cacaatcaag ttaatagaac    46920
agtttcattg cccaccaaaa tccctcaaat cacttttcag tgaaccctcc tctctctcca    46980
accattgatt tgtcttccat ccttacggtt tgtgtccttc ctcctctatg gaagtttact    47040
cttgcttttt tatgtcatgt ttagtcaaaa caccattagt tggtttgact gataacactt    47100
gaaaacctga ccttctgttc cttctgttct ctatggaagc aaaatattaa ataaacaaaa    47160
tcttccctta acatgtaa gatatcataa acctaactaa acattttgca acaaataata      47220
aacgttagct ttatatgcaa atgtaaatac aggctgagca tccctaatcg gaaatgctcc    47280
aaaatttcat attttgaatt agggatgttc aagcactaag tataatgcaa atatccccaa    47340
atccgaaaaa aatccgcagt ctaaaatact tctggtccca agcattttag atgaggaaga    47400
ttcagtttgt actaatttct aatagttttt tttttttta atattccaga tttcttttga     47460
tggaatctat gcaaatatga ggatggttca tatacttaca tcagttgttg taagttatta    47520
gattattggg gataaactgc cttgggggta gaataaagta attccatgaa gttaaaatgt    47580
ggataaatga ttgtcaaagt aacattgctt agatcatgtt tagtcaggat gatttagaga    47640
aatagattag aactccttt atccagtcta atataattca ttgtaaaagt acagttggtc     47700
ctctgcatct gtgggttcca tattcatgga ttcagccaac cttggatcaa aaatatttgt    47760
taaaaaggcc aggcacagtg actcacgcct gtaatcccag cactttggga gtttgaggtg    47820
ggcagatggc ttgagctcac aagtttaaga ccagcctggg caacatgca gaactccgtc     47880 tctacaaaaa gtaaaaaaac tagccgaacg tggtggtacg tgcctgtagt cctagtgact    47940
tgggaggctg acgtgggagg attgtttgag cctgggaggt ggaggtttca ctgagctgag    48000
ataatgcccc tgcactcagc ctggtcaaca gtgccagaca gacccttct caaaaaaaaa     48060 aattttttt ttttttttt tttttttttt ttttgagaaa aaagaggcat ggttgcgtct      48120
gaaccaaaga tgtacggacg ttttcttgt cattattcct aaaacaatac agtatgacaa     48180
tttacatagc atttacatta tattaggtat tacaagtaat ttagggatag tttaaagtat    48240
ttgggagaat gtgcttagtt atatgcaaat actattacat tttatgtaag tgacttaagt    48300
attatgtaat tcggtatctg aaggaggtcc tggaaccagt cccctaccaa taacaacaga    48360
tagctgtatt cttgttaacc ctgctgtgtg tgtaaaataa tgttagtagt tgattgtctt    48420
ttgtacatta ttttgtcact taaaatagct ggggtcagaa atgtttgact tcagtattaa    48480
aattcgtact gcaaactctg agtagagcct cctgaagaat ttcaagagtt cagtgtattg    48540
ttaatgtttt gaaatttttt tattgttttg ttagtgaata cctaatattg aatgaagcct    48600
```

```
gatgaggtat aaaaagtaaa atgaaaacaa atatccctgg tgaccgggta gtatactgtt    48660
tctttgataa ataaattata tgttttttagg gctccaaatg tgaagtacaa gtgaaaaatg   48720
gaggtatata tgaaggagtt tttaaaactt acagtccgaa ggtaattttt actttttttc    48780
tttttcttac aaagtaaaag aacattttca tagtcagtgt tttacctagt tttttaaagcc   48840
actttgaatg atttttacttc tcagtttcaa atactgatta ttttatagac tggtttgtgt   48900
aatcagagag gcttcttgat gtgtgtgctt attaaaatat ttcaaccatt tttaagcatt    48960
gtgagctaat agagggatgt ggtggtttgt tttttcctct taaaaattat tattaatgta    49020
cttaagacaa accatagaaa caaaaaacat ttagatatga ggatttttaa atgatggaat    49080
ggataataga tcatatgcct gggaaaaagg gtatgattct cttgagatta tttttgtcaa    49140
aggcatataa gaactggtac cttgatgagc taaagaattc ctaacaaatt ttattttgta    49200
aaggtttgga gtacttactt gtgttttttca ttttagtgtg atttggtact tgatgccgca   49260
catgagaaaa gtacagaatc cagttcgggg ccgaaacgtg aagaaataat ggagagtatt    49320
ttgttcaaat gttcagactt tgttgtggta cagtttaaag atatggactc cagttatgca   49380
aaaagaggtg ggttttgatt tcctaaatat gcctcatggt ttattagatt tattcaagca   49440
aagattttca cagtgatctt acaaacttttt tttaaagaaa tatctgggct gggtatggcg   49500
gctcattcct gtaatcttag cacttaggga ggctgaggcg ggtggatcac ctgaggtcag    49560
gagttcgaga ccagcctggc caacatggcg aaacccccgtc tctactaaaa atacaaaaat  49620
ttattttttgt gtgtggtggc gtgcgcctat agtcctagct actagggagg ctgagacaga   49680
attgcttgaa cccaggaggc agaggttgca gtgagctgat accgcaccac tgcactccag   49740
cctgggtgac agagcaagac tccgtttcaa aaaaaaaag aaagaaaaaa gaaatatcta    49800
cttttctagaa tagcccaagt aaggtaattt tttagaaaaa tgagaatgtt aatgcatttt   49860
tgttggaaaa caattagaac tttagagaaa aattaaatag agttttgtg atctcttaaa    49920
aaattagttt gtaaagcatt ttctacagtt ttgtggtcaa gaatgctact gattatattc   49980
aactgaaaat ttcttgtccc atttggccta caatgcttta gtttataagt gggcatgtgg   50040
caaatctgga aagaaatcaa agtataaggc taaggaagaa aggtagagaa cggttggtag    50100
aaaacaattg tctaatgaaa atgaaaaagg gtgaagaagt agaacatacg tatttttaaaa  50160
atattcagag tatgagacaa ggttttgaga atttaaaagc gattatgtag ttatattaaa   50220
aatttagtct cttttttaagt gtccattgat gaacaaagtg ggaattcctg ttactcattt   50280
gcaaggcatt attgagtgtt cagtaacacg ttgcaaggca cttctgggca atcctgaact    50340
tggttctcaa attctttttt tttttttttt tgagacggag tcttgttctg tcccctgggt    50400
ggagtgcagt ggcacgatct cggctcactg cagcctctgc ctcccaggtt caagcgattc    50460
tcctgcctca gcctcctgag tagctgggac tacaggcgtg tgccaccaca ccaagctaat    50520
ttttgtatttt tttgtagaga cagggtttca ccatgttggc caggatggtc tcgattgttt   50580
gacctcgtga tccgcccgcc tcggcctccc aaagtgctgg aattacaggc atgagccact    50640
gcacccagcc ggttctaaaa ttcttttatt tatttgtata tgccaaattc tgtagtgaaa   50700
tacgtaattc tgttgtaaat tgtagttcag tacaatttga ttttcactat tcaaatctat   50760
accaaaagct gttttttattg ttgggctgat tcttctacac tgttacttgg aaataataat   50820
ataccaggat tctttctctt agacttagga gtctttctct ttgcttgctt tttcagaggc   50880
taacagtact gggtattctt taactgtctt gatatgctga tgaaagcaca gtgttctgtt   50940
tttgaatctt ctcaaatgtc cttgtctttg attcacaact ttttgtctta agaggccttc    51000
```

```
agcatcccat acaaggaaac aagtctttt ttagctgcta cctttggagt tgattttgtt    51060
tatgtctagg agcactaaat tatttatact tatactattg aaatattcct ctgttataaa    51120
ttcaaaaatt gactttggaa gataaaattt tagttgaatt taatacatag cactctggaa    51180
agagtattgg ccacaacaaa aaaaaaggtt ccctactcta ttggatacca ggtcatttaa    51240
cagccattta cggtatgcat tgtcttttg tttttatgat gaattgatat ttcccaaatg    51300
tggaagagtg aatattactt tgagatgttt gtgatagtcc attccttgct cctcttcaaa    51360
attaatgtca ttaaatttt attactttat tagatcttca tttctcagat aattttagtt    51420
cattatagaa aggcaagaaa atacagatca gagtgacaac tttgaaaatc tcactctact    51480
cataagggga tgggtgtatt ttgctatata ttacaaaatt agttttcttg atgaggacat    51540
ccactattgg agtaatttca ggtatcttat tttttcttt ctctctcttt ttttttttt    51600 ttttggagac ggagtttcgc tctgttgccc aggctggagt gcagtggcct gatctcggct    51660
caccgcaacc tctgcctcct gggttcaagc gattctcttg cctcagcctc ccgagtagct    51720
gggtactgag gcatgtgcca ccatgcccgg ctaatttttg tatttttagt agagacgggg    51780
tttcactatg ttggccaggc tggtcttgaa ctcctgacct tgtgatcctc ctgccttggc    51840
ctcccagagt gctgggatta taggcgtgag ccaccacgcc tgggcaggta tcttatttca    51900
aaacttacag tggtttagtg aattatacaa ttgcgtccag tgcgtagtat cctgaaaata    51960
gtattaagtc atgtgtttag gacatcaggt ctcttaagct aagactatcc aggcagaaat    52020
tgccctcttc tataaaagaa gaaaagtatt aattaggaag tactatcagt atggagaaaa    52080 ccatttaga attattaatt ggcatggttt ccttcttttt ttttttattt cgagatggag    52140
tctcactcta tttcccaggc tggagtgcag tggtgcgatc tcggctcact gcaacctctg    52200
cctcctgggt ttaagcgatt ctcctgcctc agcctcccga gtagctggga ttataggcac    52260
ataccaccat gccctgctaa tttttttttt tgtttgtatt cttagtacag actgggtttc    52320
accatgttgg ccaggccgca tggttttcct taataacaaa attaaggcat ttattactgc    52380
atctagattt tttttatttt ttattagaga cttactcaga ttactcccaa agtaaaggaa    52440
ggtatggttt aatcaatgct tcttaatgct gggttcacgt ttagtcacct ggggagtttt    52500
taaaaatgtt ctcacttcta gggatcctgg tttaattata attagcctgg gtgaggctct    52560
ggacagtcag ggtgtgagct atgggtttca tgtgatgaga tcccaggagt ggctctgttc    52620
tgtggccttg agaatttgtg ctttctaggc caggtgcggt ggctcactcc tgtaatctca    52680
ctttgggaga ccaaggtggg cagatcattt gaggtcagga gttcgagacc agcctggcca    52740
acatgttgaa accccgtctt tactaaaaaa gtaaaaaatt agcgggacgt gatggcacat    52800
gtctataatc ccagctactt ggggagaggc tgaggcagaa gaatcgcttg aacccgggag    52860
gcagagattg cgagatcatg ccactgcact ccagcctggg caacagaata aaaaagaat    52920 ttgtgcttta ttttcttgcc tcacagtccc ctttctgtct cagaattggc aactgcctga    52980
aatagtctct gctgttatca tttgatagta cttttccaca tcttgaatgg atagatagag    53040 tgtttttat aatagaagtg gatgaatgat tagagtatac taatatgaca ttgtattttc    53100
ctaaaagata tgaattgatt tcatttctga gcttttataa ttctcttctg taatagtctg    53160
tcaaattatt aaggttgata atattaacta aaatttgagt gcatattcta tgtgccagac    53220
tctgtgctaa cagatttacc tacatttgtt cacataatca tcacaagttg tttctgtagt    53280
agatacagct attatccacg tcatagatga ggaaacaggc atatttagga aacttgctaa    53340
```

```
agtgaggaca caaatctagc tttctactc taactcatgt tcttaacatt atactgcagt    53400
gacataaatt atgtggtttg gtttgttgtt tatctcagtt gtcataagtc gaattaatgt    53460
ttgtttgttt gttttgagac agagtcttgc tctgtcgccc aggctgggta cagtggcgtg    53520
atcttggcgc actgcaacct ccacctcctg ggttcaagca gttatcttgc ttcagcctcc    53580
ctaataactg ggattacagg cacgtaccac cacacccggg taattttgt attttagta    53640 gagatggggt tttaccatgt tggccaggct gatttcaagc tcctgacctt aggtgatcca    53700
cccacctggg cctcccaaat tgctgggatt gtaggcatga accactgtgc ccagccagta    53760
agttccatgg ttgttaaagg atttctccac aaataaagct aaaagtaaaa aaaaaaaaa    53820 aaaaaaaaa ttctcaagca atataagatg cagactatta tgttgttcaa gttttttttt    53880
ttttttttta atctttggct ttattttgg ggaaaccttt ttttctttt ttgttttcct    53940 tgggacggag ttttgctctt gtcgcccagg ctggagtgca atggtgcaat cttcgctcac    54000
tgcaacctcc gccttctggg ttcaagcgat tctcctatct cagcctcccg agtagctggg    54060
attacaggca tgtgccacca tgcccggcta actttgtatt tttagtagag actgggtttc    54120
tccacgttgg tcaggctggt cttgaactcc tgacctcagg tgatccacct gcctaggcct    54180
cccaaagtgc tgggatcaca agcgtgagcc accgcgccca gccagggaaa cctttatttt    54240
gaggcggagt ctcgctctgt cacccaggct ggagtgcagt ggcgtgatct cagctcactg    54300
caacctctgc ttcctaggtt caagcaattc ttctgcctaa gcctcccgag gagctgggat    54360
tataggcgtc tgccaccatg cccagctaat tttatattt ttagtagaga cggggtttca    54420
ccatattggc caggctcttc tcaaattcct gacctcatga tccacccacc ttggcctccc    54480
aaagtgctag gattacaggc gtgagccacc acactcggct gctggggaaa ccttttaaca    54540
tgagtaaggt cagtgtgact tttaagttct tgatgctaac atcattgatt tcaataaagt    54600
ttaaaagtta tattcatgca tatatgcaaa tgaataaaag gctttgaaat agtgacttct    54660
tacggtacag tgaataagtt tcctttggtc tcttgaatgt tatacatgtt ccagtttgat    54720
ttactgagaa actgaaagta cctttacgtc atatgagctg tgagtcacct tggcacattc    54780
ataattagaa gagaccatca gattatcatt ggaaaatcag tttgtattta tccttatt    54840 gaattccagt gcagacagat ctgaggttct cttcattttg ctaaaacttc ttagggcctt    54900
cagtcgcttt tggctctgta ttcgtgtatc tttggaattg tcctgttatc tctgcttgtt    54960
ttttacttga ttttccatcc atttccagta ttccttctc ctctattttt ttccttcatt    55020
ttctttctgc tcttcctgtt gcgccattat tcatgttttc ctctttactc caactcaact    55080
atggctttac ttctgtttcc ttattccatt gttcctcata cttttccta ctgcttcatt    55140 ttctttgcag tattctcagc ctagatgata ggggtcagca aatctgctca tcagtaaata    55200 aatttattg tagcatagct atgcccatgc gtttgtgcat tgtctatggc tgttttgatg    55260
gctgtagcca tagagttgag tagttgtagc tgactgtagg acttgcaaag ccagaaaatt    55320
tgactgtctc tttacagaaa agtttgccag ctcttggcct aaatcatatt ttccgctgca    55380
tttagggctt tttaggactg atcaaaaata catgctatac tggctttggt gaagtaacag    55440
aatgtgctct gtcctttaaa cttacaacta attgcatgct ttgattctaa tactgtataa    55500
tatcctgcga ttcttattca tgaccattct aattggattt agtctgaaga attacttttg    55560
cttaacagat tctttgtcac atttagtgaa aaatcataaa aggggaaggt tggttaatgg    55620
aaaagatctc catcaactaa ccactacctt cctatctac aaatttatct tcttcctccg    55680
tgccatcttt ttttttttt tttcagatg atcttgctct gttgcccagg ctggagtgca    55740
```

```
gtgatgcaat cacagctcac tgcagcctcg acttcccagg ctcaggtgat cctctcacct   55800
caacctccta cataactggg actgtatgtg cacatcacta tgcctgacta attttttata   55860
tttatatttt ttgtagagat ggggtttccc tgtattgcac aggctggtct caaactgctg   55920
ggcctaagag tcttcccacc ttggcctccc aaagtcctgg gattacatga gtcaccgcac   55980
ccggcctcat tattatttt cctctggttt tagtagagag gatttttaag ccaacttcaa    56040
tcatgccctt gactctctcc cttctactta cctccttgtt ctcttttct ttttcttttt    56100 ttttagatgg agtctcggtc tgtcacccag gctgaagtgc agtggcgtga tttcagctca   56160
ctgcagcctc agcctcctga gtagctgggg ctataggtgc ctgccaccac gcccggctaa   56220
tttttgtatt tttagtagag atggggtttc accatgttgg ccaggctggt ctcgaactcc   56280
tgacctcaag tgatcacctg cctcagcctc caaagtgct gggattacag gcgtgagcca    56340
ccacgcctgg ccatcttttt ttttctcctt gctctttat accacttctc tgtttctggg    56400
ctcttcaaca tctgcctttc tagttaatct ttccctttag catgaaaacc tattcacttc   56460
ctgctcatcc taaaaaggat tctttttgt tttgttttgt tttgtttt gagacagagt      56520 ctcgctcttg cccaggctgg agtgcagtgg cactatcttg gctcactgca agctccgcct   56580
cccgggttca cgccattctc ctgcctcagc ctcccgagta gctgggacta caggcacctg   56640
ccaccacgcc cagctaaatt tttgtatttt tagtagagat ggggtttcac cgtgttagct   56700
aggatggtct cgatctcctg accttgtgat ccatctgcct cggcctccca aagtgctggg   56760
attacaggca tgagccaccg cactgggccc aaaaggattc ttttaatcc tgaattcttc    56820 tagccattat cctgcctaag gctacgatta acctctaact gccaggtcct ttggaatctt   56880
tttctgtctt tattgctgca cttgaatgtt ggtttcaccc tccttcagaa tttcctcttc   56940 tgtattttt atgtttattg atcattcctt ccctgcctca ttcctgggct tcttttcctt    57000
cacacacccc ttagatgtgt gtccccagtg tttgtttctt tgcctgctgc tcttgccaca   57060
tgacacacac tgccagctac cacacacaag ttccctccta tcatgtgtgt atcattgccc   57120
ttataccatg ttgtattaaa attatatgct tgtctcccct gttacagttt gagctctttg   57180
tgctccaagt aaagacagtg atactgtctt tattatttat tctcatggtc tagtatagtg   57240
ctttggcaca tagtacaggc tcaatataaa tgtgtttgaa taaatgaaat tcagtgcctt   57300
aatacacttt tgtagaagca ttattttatg gaaagaatga aaaagctgta agtggtctta   57360
catatatagt catccagcag atacttagag agctctggga tgtgttcctt gctgtgcttg   57420
ttgctatgga cagtacggag aaatacaaga atctatttg ggtcccttt gagaacctag     57480 tgaaactgtg tacctagtga aactgtatac cctcacccta gaaaaattta cacacatgta   57540
gattttacat gtaattcttt taaaattaa ttttttttct ttttttaaa gaaacagggt     57600 catgctctgt cactcaggct ggaatgcagt ggtgtgatca tggcttactg tagcctcgac   57660
ctcctggctc aagcgactct cccacctcag cctcccaagt agctgggct acaggtcac    57720 gccgctatgc ccggctaatt tttaaaaata ttttatagac actggttctc actatgtttc   57780
ccaggctggc ctttacctcc tgggttcaag caatcctcta ccttggcctt caaaagtgat   57840
gggattatat gtgcaagcca ctgtgcccac gctaatgtaa tttcatggtg ttcacagttt   57900
cttcagggag ttcatatacg ccatgtactc tattctaagc attttagag ttagagatag    57960 caaagcacgt gaataaattc aagaaaaatg gaatgttgta ctgcatgaca ttgaatatca   58020
aatggagtca gcgatgcaaa taattgtcta gattttacaa aaaaaattag cctggtgtgc   58080
```

```
tggtgtgcgc ctctaatccc agctactcgg gaggctgaga caggagaatc atttgaaccc    58140
agaaggtgga ggttgcaatg agctgagatc gtaccactgc actccagcct gagtgacaga    58200
gcgagactcc atctcaaaaa taaaaaataa aagaattgtg tagattttag tagttggaag    58260
aagttggagt gttaatgtgt aattagagaa cagtgagaaa taaaattcta cagattgttt    58320
tattctggtg tgctgttgtg ttctcatatg gttgtctttt tggtcttgat agtgtatcag    58380
taacagagta cgagtaacaa acagggatct cttctgaacg gcgtgacatt agaaaagctg    58440
tttacggcct caactttgct gtggtttatt aagacacaga tatgtgttca ttctggggcc    58500
aagcagtaac tggagagtgg cacttattga ggccagtatg gaggcagtac agagattatt    58560
gagattaaaa gaaagaaaca ggtggaacgg atctatgtaa tggaaagcta aacagaatag    58620
ttcgtggtac acagtagaaa agcattacat gtttattaag atatggtcat cttccattta    58680
ttaaagttac atgttttata attttagag tatatagaaa ttctctaccc tatcatgttt    58740
gccaaagtca gaacaataac ttcatttatt aaatataaaa aaaataaaaa cctctagcat    58800
aaaatagaat tttatttgga caaacgataa aaaaatactg tgtggtacta gtaagagtaa    58860
ggttgattca agatacatgg gagcagaatc caaagtgtag aaataggcca ggtgcagtgg    58920
ctcatgcctg taatttcaac acttttggag gctgaggcgg gaggatgagt tcaggagttc    58980
aagactcgcc ttggcaactt ggcaaaaccc catctctaca aaaagtacaa aaattagccg    59040
ggtgtggtgg tgtactcctg taaacccagc tacttggtgg gctgaggtga gaggttcact    59100
tgcagccagt aagtcaaggc tgcagtgagc tgtggttatg ccacggcact ccagctgggt    59160
gacaagcaag accttgtctc aaaaacaaac cagccaggcg tggcggatca cctgaggtaa    59220
ggagttggag accagcctgg ccgacatggc tctactaaaa atacaaaaat tagctgggcg    59280
aggtgacggg cacctgtaat cccagctact gggaggctg aggcaggaga atcgcttgaa    59340
tccaggagac ggagtttgca atgagccgag atggtggtgc tgcactccag cctgggtgac    59400
agagccagac tctgtctcaa aaacaaaaat aagcatagga catggggata aattgaagat    59460
ttatgaagac acagctgaag gagacataaa agtagatttg gctaaatgga acatgccat     59520 actttgaatg gaattattta atactacaac gttgtcaatt ttcctcaaat aaatctctaa    59580
agataatata ttcagttttg gccgggcacg ttggctcacg cctgtaatcc cagcactttg    59640
gaaggctgag gtgggccgat cacttgagga cgggagtttg agaccagcct ggccaacatg    59700
gtgaaaccct gtctctacta aaaatacaaa aatcatctgg acatggtggc aggtaccagc    59760
tacttgggaa gctgaggcag gagaattact cgaaccccgt aggtggaggt tgcagtgagc    59820
tgagattgca ctccagccgg gtgactccat ctcaaaaaaa aaaaatttt tataatatat     59880 atatatatat ccgttttgt agaaattgac aaaatgattc taaagcttat tagattatgt     59940
gtattaacag aagaactttg gaaattttt tccacaagag tcataaagga ggacttgccc    60000
tacaaaatat gtcagaatta aaacataact tgtcagctgg gtgcggtggc tcacgcctat    60060
aattccagca ctttgggagg ctgaggcagg cagatcatga ccagcctgac caacatggag    60120
aaaccccgtc tctactaaaa atacaaaatt agccggtcat ggtggcgcat acctgtagtc    60180
ccagctactc gggaggctga ggcaggagaa tcgcttgaac tcgggaggtg gaggttgcag    60240
tgagccgaga tcgcgccatt gcactccagc ctgggcaaca agagtaaaac tctgtttcaa    60300
aaaaaaaaaa aaaaaaaaa gaattataac tgtcacagtg ctacgtatg gagcatccaa     60360 aactgaatt atgtgggtat tttattaata tgcaatatag cactttaatt ctggaggaaa    60420
ggtggattat tcagtaaatg attctgggac attggggaca aattagatac ctacttcaca    60480
```

```
ctgataaata aaaccaaata gattaatgag aaaactgtga ttaaacaaaa caacacccag    60540
actacactgg agcaaatctg tgaatttgtt taattttgag tggagaagga ctttataagc    60600
atgactacca gagcaaaaaa atcatgaagt aaaagatcga tacctttgat tataaagaga    60660
ttaaagattt aggccgggtg tggtgctcac gcttgtaatc ccagcacttt gggaggccaa    60720
agcgggtgga tcacttgagg tcaggagttt gagaccaacc tggtcaacct ggtgaaaccc    60780
catctctact aaaaatacaa aaaaattagt caggcatggt agcacatgcc tgtaatccca    60840
gctactcagg aggctaaggc aggagaattg cttgaatttg ggaagtggag gttgcagtga    60900
gccgagattg tgccacatca ctccagcttg gcgacagag tgactccatc tcaaaaaaaa    60960
aaaaaaaaaa gacttagacg tgtccaaaag taccatacat ttaaaaagac atgccacaaa    61020
ctgggaaaag tagaaaaata gttttaaaaa tgaccagtga atgtatgaaa aggtggccct    61080
cctcacttgt aatgatttaa gaaatgcagt ttattttat tttattgtat ttttaaagaa    61140
attcagtttt aaagcagtgg aatatgattg tctatcagct tgcgctgaat ggtaaatgtg    61200
agaaagatta ctactactta gtggtactga gggagttgca aaacacttaa cactgctagt    61260
gggatggttt aagtaaaaca agtagcattc ttaaactctc tattaggtaa agaataggta    61320
agtaatgcat atgtttccag gacattttca gtaagactgt ttactgatag ggttgtgtaa    61380
tgctaatata cttactatct agttttagta ttattttttt ctcttgtctt ggatggtttc    61440
aatggagtct tatgcatgca gatatattaa aactagtaat aaagcaagag aaggaatgtg    61500
gataaattat ctctaatttc tatttgttc tatttctatt tcatactcct gggaaagaat    61560
attaagtggg catgtgtact tgaacagttg ttctgttttt tattagaaaa gaatccgaat    61620
ctataaaatg ttttacatat ttgccaggga aacagaaaag atatttgtac agctgtaaga    61680
attggaatta atttcatttt actgactttt ccttaaccta attctgaaca cttttgccat    61740
aggtttgaga ataagttgtt ataaaatgac tactattctt cactaatagt attggcattt    61800
caattcctaa attctgtttt tgattcttg aacatttctg aatttacttt ttttgtctta    61860
gttcttctac agaatcattt tcttcttttt tcttttttta tttttatttt ttattttga    61920 gacagagtct tgctctgttg cccaggctgg agtgcagtag cgcgatctcg gctcactgca    61980
agctccgcct cccgggttca tgccattttc tcctgcctca gcctcccggg tagctgggac    62040
tagaggtacc cgccacagcg cccggctaat ttttttgtatt tttagtagag acggggtttc    62100
accgtgttag ccaaggtggt ctcaatctcc tgacctcgtg atccatccgc ctcggcctcc    62160
caaagtgctg ggattacagg catgagccat cgcacccggc cttcttttt tctttctctt    62220 taacttctga gctgaaaata gtacctttta taaagaagtg ctcaaacgat gattggactg    62280
atttctcctt atttctctct ttctctctgt ctctttcact ctcttttag aattttctct   62340 ttttaagtag agacgaggtc ccactatgtt gcccaggctg tcttgaactc ctgagcccaa    62400
gcaatcctct ttgcctcagc ctcccaaagt gctcggatta caggcttaag ctatcacacc    62460
aggcctaggc taatttcata ttttgagatg gcacaaattt ctttcaggta gctagctttt    62520
cctcctcctc cccacttaaa atagatcctg atccagaagc ctaatggaga aaatgaaaac    62580
agaatgttca cccataaaca gtatcttgt attggaatct tttctaaaac ttcttttgat    62640 cttttagga gatagtgtgg gaatcagcaa tctagtatta cgtacgtgga atctgtcacc    62700 ttgtttttt aaatacagca aacctcatga agtgaatttc catatttttt cttgttcttg    62760
ttagttttgc accactcagg ctttgctgta gaatttgatg tatatttgat tctgtagagc    62820
```

```
atgggctatt gatcttcact cagctttcag aggaatctga ttagtaagtt tgagttttt   62880 attatttttt agttgatttt gaagtaaaat acagcaccat tttaactgat accatttcta   62940
aacaattttc agttcaaatt ttaagttagc taatttagag cttaagaaaa ttgctttaaa   63000
aacataaaat tactggctgg gtacagtggc tcattcctgt aatctcagca ctttgggagg   63060
ccaaggcaga tgaattgctt gagcccagta gttcaagacc agcctgggca atatggtgga   63120
accccgtttc tacaaaaaaa atacaaaaag tagccagaca cggtggtatg tacctgtagt   63180
cccagctatt cgggtggcag aggtgagagg atcatctgag cgcagggaga ttgaggctgc   63240
agtgagccaa gtgagaccct ggtttcaaaa aaaaaaggt tactaattgc agtgcctttt   63300
atcttattta atgggcttag tcaaactaag atgatgtatt ttatcttata aatgttttcc   63360
cttgaatttt aactgaagaa tccaatttgt acctctcaca aacagaatgt attagtaagg   63420
aaaataaata ctgcttttta ttacttaaat aggatatatt tttctcttag ggatttttt   63480 tctattttat ctcactttat cgtagtgcta gaaaatttaa tcattcattt gagataggga   63540
gaaaattagg tttttttttt tcttctattt tgagacaggg tctcattttg ttgtccaggc   63600
tggagtgcag tggcgccatc gtagctcacc ataacctcaa actcatgggt tcaggtgatt   63660
caccttagcc tcctgattaa gctgggactg cagatgtgta tcaccactcc tggctaattt   63720
ttgttgttat tttttgtttg atgaggtctc attatgttgc ccaggctggt ctcaaactct   63780
gggcctcaaa tgatcctcct gccccagcct cccaaagtgc tgggattaca ggcatgaacc   63840
tctgctccca gcccattttt taaaatatat tcacagcatt gtgcaaccat cactacaatc   63900
aatttacatt ttcatcaccc tgaaaagaaa ctctgaaccc cttagcagtt cctctctgtt   63960
tgtttcaatt ttccccagct ccaggcaact attgatttat tgtcttcata ggtttgccca   64020
ttctggacat tgcgtattaa tggaatcata taatatatag ccttttttt tctttttttt   64080 ttttgaaaca gagtctcact gtgtcgccca ggctggagcg cagtggcatg attgcagctc   64140
actgcatcct ctgcctccca ggttgaagcg attctcctgc ctcagcctct tgagtagctg   64200
ggactatagg cgcctgccac cacacctact aattttatat tttagtaaa gacggggttg   64260 caccatgttg gccaggctgg tctcgaattc ctgacctcaa gtgatctgcc cacctcggac   64320
tcccaaagtg ctgggattgc agccatgagc caccgcatct ggccatatat attatgatag   64380
gcttgtttca cttagtatgt ttcttccatg ctgtagcatg tattagtact tcttctttt   64440 tcatggccaa atattccatt atacagttac acaggtacac tacattttgt ttattcatca   64500
gttggtggac attttcattg tttccacctt ttgatttata cataatcctg ctgcgaacag   64560 tgactttaa agtttttgtg tgggccgggt gtggtggctc atgcctctgt aatcccagca   64620
ctttgggagg ctggggctgg cagatcattt gaggccggga gttcgagacc agcctgccca   64680
acatggtgaa accctgtctc tactaaaaat acaaaaatga gctgggtgtg gtggcgtgca   64740
cctgtaatct cagctactag ggaggctgag gcagagaatc acttgaagct gggaagccga   64800
ggctacagtg agccgagatc acgccactgc actccagcct gggtgacaga gtgaaacttc   64860
atctcaaaaa aaaaaaaaa aaaaaaaaac tgcgtgtgga cataggtttt caattctcat   64920
gggggtgtgt gtgtatgcat actcatacat acatacacat acctgcaaga taattgctgg   64980
ctcgtatgct aaatctatgt tgaacctttt acataactgt tgggctgttt tgttttcttt   65040
ttattatttt ttgaaaatag agttggggtc tcactgttgc acaggctgat ttcctgggca   65100
tagtggctgt atcattttac aatcctacat agctgtttcc aacgtagctg tatcatttta   65160
caatcctact agcagtgtct gaggtttctt atgtttttca catcctcacc agcatttgtt   65220
```

```
attgtctgtc tctttgatta tacccatcct agtgggagag taagaagtag tatctcactg   65280 tagattttt tttctgttt acaactttac tttaaaaatt atatatgcac acatggtaaa    65340
aagttcaaaa cgtgtgtacc aaaagattta acagtgaaaa tagaaaataa gtgtggtcct   65400
tgttttcttc caccaaggca aatattgtta taatctccta aacaacttgt cttccagatt   65460
tctcattttc agtcaatctt gggcattgac ataaagaaat tcttagacat tgcttttatt   65520
agatcatctc atcccttgct caaaatcttc agtggccact gttgtttaca gaataaagtt   65580
gggatgctat acagggccct tcccagtgga acttctcttt ttcaacctta tctctcatta   65640
tttcccaatg tttttttttt ttttttttgag acggagtctc gctctgtcgc ccaggctgga   65700
gtgcagtggc gggatctcgg ctcactgcaa gctccgcctc ctgggttcac gccattctcc   65760
tgcctcagcc tcccaagtag ctgggactac aggcgcccgc cactacgccc ggctaatttt   65820
ttgtattttt agtagagacg gggtttcacc gttttagccg ggatggtctc gatctcctga   65880
cctcgtgatc cgcccacctc ggcctcccaa agtgctggga ttacaggcgt gagccaccgc   65940
gcccggccta tttcccaatg ttaatctact tattgaccta ctaagctggc atgttctgtg   66000
tgttagacat caccaacttt gtgccttctt ttttgtttg ttttgagtt ggagtctcac   66060 tctgttgccc aggttggagt gcagtggcgc gatcttggct caccacaacc tctgcctccc   66120
gggttccagt gattcctg cctgagcctc ccgagaagct gagacgacag gcgcgcgcca   66180
ccatgccctg ctaactttg tatttttagt agagatgggt ttcactgtgt tcccaggct   66240 ggtctcgaac tcctgacctt gtgatccacc tgccttgggc tcccaaattg ctgggattac   66300
aggcgtgagc caccgcggcc ccctgtgcct tcttctttta ctcctggatt taatcccaac   66360
gtgaagaatc taccttacta actagagttt tagatacttt ttcaaaacca agcccacatc   66420 tgtcctttt agagtcttct ctgaccttcc ctgctcattg tggtttgttt ttattgcctg   66480
taacaatggc tgttaaactt tacattttaa attaatttat gtttgtatgt atttatttgt   66540
tgagaaaggg tctctctctg tcacccctac tagaatgcag tggcgccatc atggcttact   66600
gcttcctggg ctcaagctgt tctcccattt cagcctcccc atgcaccacc ctacctggct   66660
aatttttttg tttgttttt ttagttagt ttttgtagag acagatgtct cactgtgttg   66720
cacaggctga tcttgaactc ctgggctcac ttgatcctcc catctcagcc tccccaagtg   66780
ctgggattac aggtgtgagt caccatgccc agactttaac attttctttt tagtataaa   66840 taggtcagtt ttttttccctc tgatgagatc ccatgctgac tcttagttaa aacaaggctt   66900
tggttggaag aagagctagt gatgtcctag ctccctactt actccactt cccttgcctt   66960 ctggggtgtc ctgaagacat catagggtgt catgaagtac agttggagaa ccagtggtct   67020
ccatcatgta ccaaacactc atcttcacga agcagtatgt agtgtcttt ttaccggtat   67080 attttctctc tcccaatgca ttaaactttt ctggagttca gaaaacaaat ttatagaatt   67140
aaggaaatgc gtccccccca accatggtgt ctagtatata tacagtgact tacagataac   67200
aggtgttcaa catatatata ttcctttgat tgattttga aaagtttaca tgtatatatt   67260
ttttatatac ggggtctcac tctatcactg aggttggagt gtggtgatgc agatcttggc   67320
tcaccgcaac ctcctcctcc caggctcaag tgattctccc acctcagcct cccgagtacc   67380
tgggaccaca ggtgcgcatc accatgcctg gctaattttt tatattttg gtagagacag   67440 gattttgccg tgttgcccag gttggtttcg aactcctgag ctcaggcagt ccacctgcct   67500
tggcttccca agtgtgagcc accactgaaa tactatatt tttaaactta atttatttat   67560
```

```
atttattata ttttatgtt tttatatttt aaaaaatatt tttatactca ctagacccaa   67620
ttttatactc ctaaaccagg gaataactgt ttttttttct cttacatagg catgatacca   67680
tagacaatga ttaaaattgt aattaccatt catttcttag ttttgtggct gggacactga   67740
tgtcttcaaa tgttagtttg caaatacagt cagccctctc tatccatggg ttacacagct   67800
gtgaattcaa ccaaccatgg atccaaaata tatgggaaat acgctggggc tgtgggtcac   67860
acctgtaatt ccagcactta gggaggctga ggcagatgga tcacctgagg tcaggagttc   67920
aagaccagcc tggccaacat ggcaaaaccc tagctctact ataagtacaa aaaattagct   67980
ggccatggta gtgcacatgt gtaatcccag ctactcgaga ggttgagaca agcaatttgc   68040
ttgaacctga gaagtagagg tttccatgag ctgagattgt gtcactgcac tccagcctgc   68100
gcaacagagt gtgagaagaa aagaaaaaaa actgtctgaa aagaaaaaaa aaaattatat   68160
gggaaatcaa aagcatctat actgaacatg tacagacttt ttttcttgtc attattcctt   68220
aagcagtacc acaactattt ccgtagcatt tactttgtat taggtattat aggtaaccta   68280
gaggtttaaa gtatgcgaga gtatgcaaat actacaccac tttgtatcag ggacttaagc   68340
atccctggat tttggtatcc ctaggggta ttagaaccaa tcccccatag atgctgaagg   68400
acaactgtag tgtgtgttgg aataatttat tttcaaatgg atcatttgga gaacactatt   68460
ctttaggaaa catagcctcc taagttctgt tccatacatc cctttcacct ccacggcgtt   68520
gtagcatcct gctttcatga ctgtgtcatc actcggaagg aactgcttct cttccagaat   68580
gcttttcaag atctactctg accacagcta taaactttac acttctattc tcttcttgcc   68640
cctcacagtg ttctctgttc ctctaagatc ttaaactctg tctactccta atccagcctg   68700
ctgggtgtgg ctggagaaag tcccactggg gggctgatta gttaggaatg tagggtttcc   68760
agctcttgct ggagcctcag aagagttcag cagactttt tttttttttt tttccttaaa   68820
cctatttctg cagccttgat gaccactcct tccagtccct cacctatttg ctttattcat   68880
ggcagaggct ctttcttcct gcttgtcagt acaaagaggc aggattcttc acctggatct   68940
gtggattctc aaagaatttg tggagagaat tcagggcatt gatgaccttg gatgaagaga   69000
aatttacatc tttatttaca ctaaccttca agtgaaattt agcatttttt gccatttaaa   69060
aatatgggca acaaacaact agtagtatta gcagtattta tgacttaagc acctatagaa   69120
ctcagttaat ttcatatcgc ttgatgttat gggtatctca aattattatt ttatgtatat   69180
atattttga gatggagtct cgctctgtct cccaggctga gtgcagtggt gcagtctcag   69240
cccattgcaa cctctgcctc ctgggttcaa acgattctcc tgcctcagcc tcctgagtag   69300
ctgggattac aggcgcacac caccacgcct agctaatgtt tgtattttca gtagagaagg   69360
ggtttcacca tattggccag gctggtcacc aactcctgac ctcaagtgat ccgcctgcct   69420
tggcttccaa agtgctggga ttacaggtgt gagccaccgc acccggcctc aaattatttt   69480
tagaaacaga atcttgatat ggtatccgct ctggccttga acttgtgggc tcaggcagtc   69540
ctcccacctc agcctcctga gtagctggga ttataggcat gtgccactgc accaggcttc   69600
aaattattat gtatgttcat cacctcttta aatttataat agttattaaa cctgttactg   69660
gatcttaata tttaatgctt taattaagaa catgtatgtt actatgccaa cagattttt   69720
tagttttga taactgcatt tcattgttac ttgttctcat ttgatttcct gtgtatttta   69780
cgaatttaag tacattctga atacggtttc ataggcttcc ctaaaatatt gaaggggccc   69840
atggattaag aaaaaggcta agaatcccta atctagaggc tccccacagt cctcttttgt   69900
catcataccc ctaccccatt ctagcctgag gagcgtggct ccacctgtgc ccttggtttt   69960
```

```
gttgttccag tccatacatc ctgcacccct aactgtgttt cttatcccca acttgtttct    70020
ttgtgttatt cttcagtatt atagtcttta atataatctg tataatacat ggtgtagtag    70080
tatatgctcg tagtatacaa ttcagttaga acagatgagt attcaatgaa aagataatct    70140
cctctctaac ccccagtccc acttccctgg ggaagcctgt gttcttgtgt acaattcaga    70200
aaatgtttat acacatattt tttatttatt tatttttgtga gacggagtct cgctctcgcc    70260
aggttggagt gcagtggcgc aatcttggct cactacaacc tccgcctccc tagtagttca    70320
agcaattcaa ggttcaagca attcgcctgc ctcagcctcc cgagtagctg ggactatagg    70380
cgtgtaccac cacgcctacc taatttttgt attttttagta gagacagggt ttcaccatgt    70440
tggccaggat ggtctcgatc tcttgacctc atgatccacc cgcctcagcc tcccaaagtg    70500
ctgggattac agatgtgagc cactgtgccc agcctgttga tttaatttta aacagagttt    70560
cgctcttgtt acccaggctg gagtgcaatg gtgcgatctc ggctcaccgc agcctctgcc    70620
tcccaggttc aagtgattct cctgcttcag cctcccgagc agctgggatt acaggcatgc    70680
accaccatgc acagctatat ttagtagaga tggggggtttc tccatgttgg tcaggctggt    70740
ctcgaactcc ggacctcagg tgatccgccc gcctcggcct cccaaagtga tgggattaca    70800
ggcgtcagcc actgcacccc gcctatacac attttttttgt tttttgtttt tttgagatgg    70860
agtctcgctc tgttgtccag gctggagtgc agtggcgcga tctctgctca ctgcaagctc    70920
tgcctccctg gttcacacca ttctcctgcc tcagcctccc gagtagctgg gattacaggc    70980
gccggccact acgcccatct aacttttttgt attttttagta gagatggggt ttcaccgtgt    71040
taaccaggat ggtcttgatc tcctgacctc gtgatctgcc tgactgggcc tcccaaaatg    71100
ctgagattac aggcgtgagc caccgctccc agctatacac gtatttttaa tgccactcca    71160
gtctatgttg gaaccatttt acttcccctt tcttattttc ttcttgtgtt cttgaaggcc    71220
tagatcagct gttgctgata ggctgtcact gtcactttag aaagcccaga gccttttgtt    71280
ccttagaact ttgttttttaa ttgtattgta gcactcattg tattcgattc taaaagattt    71340
gcttcatttc tgtaactagt ctcttacacc caggagctcc tagttcctac aggaaatgct    71400
gggaattgta tcagtcaaat gtgaatcccc acctcgtcca gacttatgag tgcattgtag    71460
gtactcagta agtgctaaaa atgactaaat agtcccactg ataccaatct atatactgat    71520
actttatata gtatatagat tggtccacat ataacgatga cacataatga gaaactgtct    71580
taaaaagttg ttgaaagtgc cgcaggaata ggaattgatc aaaacaatat gatttttttag    71640 gtttatatgg aactttgatg tttgagaaaa ggctgattta gttgagaaga aatggttagc    71700
tgaggatttt gatgacttct ctggaagcac atttgagggt ttgtgatgtt aaatctgatg    71760
ttaatgatta tttcatccag ttttatgtca ttttatagtt tttatacatt taagtatatt    71820
tatttctaat gtttaacact accattttag ttatttgacc attattctgg cccttttaaaa    71880 aatgctcaga caagtttgaa tgattttttca gaggcattat tggctcagag gtaaaagagg    71940
aaagattgag aagctgaata tgtactctgt ttcctgggta tggggctggg gataccagaa    72000
agaggttcac acgttggtcg agacatttct ttatgaccac cagcaggtgg catcaccggc    72060
ccaaaatgac taagtttctg cccagaatca gaagagaagg tgttgagagc ccactgctgt    72120
gggggtagca tggaggtggg atacaggggc tggaggtgat acaatttttgt ttcttcctcc    72180 aacatcgcct gctagtctag aggcttttat aaattgaaaa actaattctt tatcatctca    72240
tctgatggtt tttatgtttt tcctttttttc tctctatacc tgtagttcct tcagaaacag    72300
```

```
gtaacacttt tctaatagtc acgttgtatt cttgcatctt gttgttacaa tgcttttgtt    72360
tctcaccata ggggatgatg gaaaattaat attctttgac ttatggcatt ggtaaaatct    72420
gcatgcaaat tcccacagtt gcctgtagat tagagccagt tgttttttc  tcaactttgc    72480 aggaatcctg gttacaacat tgtactattt actaccaaca gtgttttttt tttttaaaat    72540
ccagacttgc tgggcatagt ggctcatgcc tgtaatctca gcgacttggg aggctgaggt    72600
gggaggattg cttgagccca gggctgcagt gattgcggca ctacactcca gcatgagtga    72660
caaagacccc atctctgaaa aacaaaaac  aaaacaaat  ttttttaaa  gaaacagaaa    72720 caaaaatcca aacttgtaac cactgtaaaa caaatcagaa tttacgatag tggatattat    72780
taatagtgca gaatggatac ccagatcttg cttcctttct agctaatgat gcaatgttgg    72840
cctgaaatgc attacttata gccagggatt ttctcagcat cctgatgata tagcctcatt    72900
tcgtgctaac tctccacttc tgcacatctt cccctaagtc ctttactcat ctttagaaag    72960 agctacttt  ggtgaaattt taaaaccaag gaatatcatt ctttatagaa tcacacttct    73020
gtgttttccc cttccccatt tctgtctcga aagcgacaga ctgctacata acctgtgaat    73080 acttttttt  aaaaaagtt  tggtattgta aacagaagat ttaagattaa aatgtagcat    73140 tgagaaaat  agatttatta ataatgccct cttaacacaa cctaaattct ggtcagtgga    73200
ataaagcctg ggtcctaaag ttttagacgc ttgcttgctt ttccacactg gctcttactt    73260
ggggatcctt ttagaaattt gtttagaata atactgtaaa aacatattta agctactttg    73320
tgtgtacatt tgggatcttt tggtttgaag acggcttgac tcaagacttt ctaaatattt    73380
tcacacacac acataccc  tgtagtgaga aaaaaatccg tttatatggt tctataaaaa    73440
tctctagctg cttcgagctt taatttcttg aatcaaaaga gtattgtttt taatactgag    73500
cttctatcta aataaatgct ttatttactt aaatgtgtgc ttttcaaaaa ctagtatgat    73560
taagacatta acaggatctt agacgtaaag gaacagtcct gttgcttctt ccagaagata    73620
atatgactcg tttggaattt tcctatagtg tagttttttg tctagtgttg tgagaattaa    73680
agggatttca ggatcttaag gtaggttatt attgatgtt  ttcttggaac attttacatt    73740
cttgaaaata cacatggcta aattaatttt tgccagcaat ccacataact ttaagataat    73800
gtagagaaga acgtgattca ggttagtatc aaataaggtc agatttctag tgccatcagt    73860
agctttcagc aaagatgagg tgttggtaag atagcattag tctcttagaa tctcttagag    73920
agattttcca aaattcagcc atttctagtg aatgctccat tccacccca  gctgagtcct    73980 gctgctctgg ggaactccct cagcacactc ttggctctta gaattgctag caatgggagt    74040
agtgctgctg gtggagctgg cagctaagcc cagaggtgga ttaatgcttt tattccctga    74100
tgtacaggta cacacactca tacctaccca cacctagttt gggataagaa gaggttagaa    74160
ttagctaggc ttgaagttcc atgcttaaat ttgctggctc agatttctta ttttggcatc    74220
actttgccca ttagggagac aatgacagtt atagaagcat tgccaaataa aaaatccatc    74280
tggaataacc tcttttgtag gagtattgtg tgtttagttg ttgattcgtc ccttcctcct    74340
cttagtggca acttacagta ctgggaagga acagtggctg ggagcttata ttcctcagca    74400
gagccagatc agcagaagta ttactcctta gttcgtagta ggtggtaccc tatgggtcca    74460
gtcatttaaa tgcaagcctg tatctacaga gcgtttccta gtgccatcat tgcccagtgg    74520
gcctttattt agctgagtct aactcccaac tagagaaaat ttcctgtgcc agacagcagt    74580
atggtcagct aacatgtgga tgctacattt gctttcataa gtcagtactc ttcaataaca    74640
ttagtagaag agaagaggac acaaagtgag agtgtgttaa taggaagtcc aggtatgcct    74700
```

```
gctacctgaa ctttctgaga caggtaatac tgtagggcct gaactttgta gcagagtggt    74760
tatatatgaa gaagtgggtt ctgggagggg ttaaaccact tagaatggct tcatttacta    74820
atggcaagag tttgctggga tattgaccac tgtacataga catgaatatg gaaagttaaa    74880
aacaaaatcc acatatattt ggctgcaagt actccgaagg tatatctaat tagtgcatcc    74940
attaaacaaa agagatattt taggccgggc atggttgctc acacctgtaa tcccagcact    75000
ttgggaggcc aaggtgggtg gatcacctga ggtcaggagt tcgagaccag cctggccaac    75060
atggtgaaac cctgtctctg ctaaaaatac aaacattagc tgggcgtgtt ggtgggcgcc    75120
tgtaatctta gctacttggg aggctgaggc aggagattcc cttgaacctg gaaggtggat    75180
gttgcaggga gccgagatgg tgtcactgca ctccggtctg ggtgaaagag caagctccat    75240
ctcaaaaaag aaaaaaaaaa aaagagatat ttttgatgga ttgatagaaa ttttcttttt    75300
ctttttttt ttgagacagg gtctcactct gtcgccaggc tggagcacag tggcgtgatc    75360
tccattcatt gcaacctcca cctcccgggt tcaaacgatt ctccttcctc agcctcccga    75420
gtagctggga ctacaggcat gtgccaccat gcccaactaa ttttgtatt tttagtagag    75480
agagggtttc accatgttgg ccaggatggt ctcgatctct taacctcatg atccacctgc    75540
ctgggcctcc caaagtgctg gtattacagg catgagccac cacatctggc cagaaatttt    75600
cttggtcact tctgagacat gcagagtaat tacctgtaat ataatttaat gaattatgtc    75660
aatatattaa aatatgcttc atgtgggctg ggcatggtgg ctcatgcctg taatcccagc    75720
actttgggag gccaaggtgg gggtatcact aggtcaggag atcaagacca gcctggctaa    75780
cacggtgaaa ccccgtctac taaaaataca aaaaattatc cgggcgtggt ggtacacacc    75840
tgtagtccca gctactcggg agactgaggc aggagaatcg cttgaacccg ggaggcagag    75900
gttgcagtga gccgagatca cgccactgca ttccagcctg ggcaacagaa cgagactcta    75960
tctcaaaaaa aaaaaaaaaa tgcttcgtgt ggcttaaaat tatatgaaaa gaaaatacct    76020
ttactgatag tcatctgtga ttccatttgc taaattaaac gtgaaagcat acttttactg    76080
aatactatat attccgtatc agtttagata gcagtttatc ttcacataca taagttttaa    76140
gtttaccttt attatagtgc attggtcttt tgttttcatc aacctaaatt atgttcaata    76200
aatgttctg ttagatttta agttaaacaa ttatgtgaaa ttcattttc gtaattgttt    76260
tttaacatat gtctttgttg gtaattcacg tgtgtgagtg taactgattg ccagattata    76320
taaactttca accaaaacca ttctttgcag atgctttac tgactctgct atcagtgcta    76380
aagtgaatgg cgaacacaaa gagaaggacc tggagccctg ggatgcaggt gaactcacag    76440
ccaatgagga acttgaggct ttggaaaatg acgtagtaag taacatcttt gtaattattg    76500
ctagactctg gtcagtatga catcctgtca cttggttgta atttaaatgt gcttttgttg    76560
ttgttgttat tgtagtgagt gtatttagag cagcaggttt ttgtataac tagagacttt    76620
ctcccaagca atatataaag aaaaatgttt gtcattttac ttgtaggggt taagcaggag    76680
tactgtctgt tcttgtggat gctcatgaat tacttctttg tgattaaaat aaataataag    76740
aagtagctta aattaaaatt agaaccatg ggaaatgccg gtgtgttttg ctttaacacc    76800
cagccaaata aggtagccta aggaaagtgg tgtcttaatt gttgacttca cctagagaag    76860
aggttgaagt aggacatttt aagcctcttg tctgaagaaa aggttgtcat taagataaat    76920
aattaggtta cattggaatt aaagcattac ataaatttct tggtcttaaa tttggattat    76980
tctccacaaa attctttat ttctaaaacg cctcttgtca catactagtt ttgtttctct    77040
```

```
ctttaatgca ttatctgtac ttgaagtgct tagctgggta tgctggcaca tgcctgcagt   77100
cccagctact tgggaggctg aagcaggagg atcacttgag cccaggagtt ggagtccagc   77160
ctgaatgaca taaggagacc ccttctctaa gaaataaaaa taaaaacaaa tacttaataa   77220
agactctgtc tttaggatag agagcataga gatataaagc aaagtgtctt gccaaaaatg   77280
agtgttatgg taccaatatt tgagtagaat gaagaatctt ccattgagta gaaagagaat   77340
ttgtaacata tctgtgtttg atgtttaagg cataacagct taataatgac actcttcctc   77400
agacaggaag cctgaaatgt cctactttga cctaaagtct agtaataaaa ctggacatac   77460
acaggcaaca tgtcattaat tctcaaactt taacaaatca tatataacct aatataatgg   77520
ttctcaagtc tgtacatcac gtcacctgta tgaaaaatat gaggaaacag agacttcttt   77580
tacactattg gtgaggtgga taaattgata gagtctttct ggagagaatc tggcaatgct   77640
aatcaaaatt taaaatgcac atacactttg ttccagcagt tctatctcta gtaatttatt   77700
tttgccctca tatatccata agacatgcaa ataattatat gtgaagattt ttttttttc    77760 tttttctgca gagacagggt tttaccatgt tgcccagggt gatctggaac tcctgagctc   77820
aggtaatcca cccacctcag cctcccaaag tgctgggatt acaggtgtga gccatcatgc   77880
ctgaccagga ttttttttttt tttcagcatt atttcttttg ttgttgttgc tgttgttttg   77940
agagatggag tctcactctg tcacccagac tggagtgcag tggtgcgatc tcggctccct   78000
gtaacctcca cctcctgggt tcaagtgatt ctactgcctc agctttccaa gcagctggga   78060
ctataggcgt gcgccaccac acccagctaa ttttttgtatt tttagtagag acggggtttc   78120
accatatgtt ggccaggctg gtcttgaact cctgacctca ggtgatctgc ccacctcggc   78180
ctcccaaagt gctgagatta taggcgtgaa ccaccatgcc tggccatagc attatttcta   78240
atagtgaaaa attggaaaca tgctaagtgt ctatcaatat agcatgagtt agatttatga   78300
tgtcaccatt caattgaaac actacatatc tcccaaaaag aatggtgttc caatatggaa   78360
agatatctaa gatttattaa gagaaaaagc acattgcaga acactgggat cctatttgct   78420 ttttttttc tttttttgag acagagtctt gctctgtcac actgcaacct ccgcctcccg   78480
ggttcaagcg attctcctgc ctcagcctcc tgagtagctg ccaccatgcc cagctaattt   78540
ttgtgttttt agtagagaag gggtttcacc atgtttgtca ggctggtctt gaactcctga   78600
actcgtgatc cacctgcctc agcctcccaa agtgctgcga ttactggcat gagccaccgc   78660
acctggccat gaaattttttt tttttttta aagagctgtt catattctta ttgcctagaa   78720
gatgtctgaa attacaccca agaaactctt tttgagacgg agtcttgctc tgttgtccag   78780
gctggagtgc aatggcgtga tcttggctca ctgaaacctc tgccttccag gttcaagcga   78840
ttctcctgct tcagccttct gagtagctgg gactacaagc gcccgccacc acatctggct   78900
aattttttgt atttttagta gagacagggt ttcaacatgt tggccaggct ggtcccgaac   78960
tcctaatctc aggtgatcca cccaccttgg cctctcaaag tgctgggatt acaggcatga   79020
gccactgcgc ccggctgaaa ctctttttttt tcttttaag atggagtctc gctctgtcgc   79080
ccagacttga gtgcagtggt gtgatctcag ctcactgcaa gctctgcctc ccgggttcac   79140
accattctcc tgcccagcc tcccaagtag ctgggactac aggctcccgc caccacacct   79200
ggctaatttt ttgtattttt agtagagaca gggtttcacc atgttagcca gcatggtctc   79260
aatctcctga cttcgtgatc ctcctgcctc ggcctcccaa agtgctggga taccaggcat   79320
gagccaccgt gcccggccag aactcttaat agtagttatt tatgcacgct gggattgaa    79380 gacatttact ttttactgga tgtctttccg tattgtgtgc tttttttttt ttttttttat   79440
```

```
gtagggcata cattacttaa gtaattttaa agcctccata agtaagtgtg atttcctgcc    79500
catgtgtttg gcaaaaggaa ttgcattggt ggtagactta cattatagtc ttacctggag    79560
tagcacagga ggacccaagg ttaataggtg aacttcgagg caagccttag cattgaggtt    79620
gccatcagca ttgcttggtt gatgtgttca ttcttctggg atggattaca acctttactg    79680
gactttatac ttttcaccag taaggcttta aaaaggagt tgaaacatta gagataatt      79740
atccaggcag taatattcac tggtaaatag tcttccagcc tgtggcccaa ttggttgatt    79800
cttttacgtt aaagaatgca gcctcagctg ctctgcctat ggagtaggat tcttttattt    79860
actttcttaa taaacttgct tgcccctggc tcccccccac caaaaaaaga aggcagcctc    79920
cctttttgcga atggtaattt cctatagttt cctcgtagaa ttgtggagtt acctatgctg    79980
aggttatagg ttagggtatt gagatccaga gttgccactt ctgaggtgtc acaactgcta    80040
atggtaaaac catttctaaa gcccagttct tgtgactttg tccagtgatt gcctgttcac    80100
cgtttcatgc tgccttccca tttgagcatt cccaggagga aggggaggtt gccagggacc    80160
tagtaccata gtccgacctt ggaatcgttg aatatgaggg aaagcgttgg cttctccctt    80220
ctttctccca aacattggaa gtattttggg ctgttaaaaa gcaccccttg ttccatgtgg    80280
aatcccttgt ttaaaagaag taaaatatgt acctcctgtc ctccacagac ctgaggacca    80340
gtgtgatctc aagaaggtta caggtaaatg tagatgtctc taactgaaag gtggctttta    80400
caggttagag aaaagagaga accctgatct gaaggctatt ttatgaagta attaaaatgt    80460
tctaaacttt aaaaataact gctcaaataa ttgtgttgta tagttactta tcaactggag    80520
gggctgataa gtatttttct aaaacatttt taaggaaatt ttttcctatt ttctaatttg    80580
ctaattttgc tcaagtagtt tgttagatat tgttaatata gatgttggtt ataactgaat    80640
gaaagggaac aactactttg acattttgaa aaacaagctt cattttcttc tagtctaatg    80700
gatgggatcc caatgatatg tttcgatata atgaagaaaa ttatggtgta gtgtctacgt    80760
atgatagcag tttatcttcg tatacgtaag tttgaaaagt ttgttttta  tttagtgcat    80820
ttgtctttga ttttcatcag cttaatttat gatgaataaa tgtttgttag ttttaagtt    80880
aaacaattac atgaaataat ttttctctta ttaccaactg tgataaattt ccattaaaaa    80940
aagggaataa atgtagtttg cctataccct gtttttatgc tctaaacaaa ttttggtttt    81000
gtctttttt  ttcttttgag agggaatctc gctgtgtctc caggctggag tgcagtggtg    81060
caatctcggc tcactgcaac ctctgcatcc cgggttcaag cgattctcct gcctcagcct    81120
cccgagtagc tgggactata ggcgcgtgct accatgccca tctaatttct gtattttag    81180
tagagacggg gtttcaccat gttggccagg atagtctcga tctcttcacc tcgtgatcca    81240
cctgcctcgg cctcccaaag tgctgggatt acaggtgtga gccactgtgc ctggccggtt    81300
ttgtcttcta agttgttaaa aaatatctaa atttgcaagg gcagagatta tggtgaacag    81360
tttaaccagt ttttgaaata tgttcctctg gagaaaaggt aacagaaaaa aaagttagaa    81420
ttttgattta taaatacaca gatcactata acttttagtt ttagttttag ttttagtttc    81480
tgtttttacc agtattctaa actctaaact ttcttagtag ttgattatga cagatacata    81540
aactgtggct ttaaaggact catttgtctt ttcttttcct catgtttcag agtgccctta    81600
gaaagagata actcagaaga atttttaaaa cgggaagcaa gggcaaacca gttagcagaa    81660
gaaattgagt caagtgccca gtacaaagct cgagtggccc tggaaaatga tgataggagt    81720
gaggaagaaa aatacacagc agttcagaga aattccagtg aacgtgaggg gcacagcata    81780
```

```
aacactaggt atttaaagga aatcatgatg cagtattttg gatacacaac tcaaggtctg   81840
tgtgagacgg tgtattgtta ttatatttcc tcttccttta atatagctta ggtagagaat   81900
gcaagtagaa ttggtttaag atctgttaga gaaaaggtta tggtgatctt ggaaaatatg   81960
cttttgagag taagctctgt ggagccaagt gttggtatat cacggtgagc aatccaagat   82020
cttgaagagc ttgttaaaat agttatctgg tgggggacac gtgtaacaat cacagcagta   82080
caatatgatt tgcttggtta aaggcatgtt caaagtacta ggaacataca gaatgaggag   82140
gagctagcat aacctgtaga gtcagagaaa acctcattga ggaggtgaca ttttgtgata   82200
agataatagg gtcttttgaca cttagagaag agttgggaga agagtttatc acctgatgaa   82260
aagccatgta caagcatggc tatgagaaaa tttggccagc tcaggagagg gctggttgtt   82320
gcatgtgtct ggaacacagg atctgtgtca ggtgcagcag tggcagttga tagtaggaac   82380
tgaggtcatt aaaggacttg gcatgtcatg ctaaagagca ccctgttgga aggagatggg   82440
gtgaataaac cctggggcat tgaggactgg ctgagacaca gagaacagtt agtgcactga   82500
aatagttcaa ctgtgagaat ttggtaacca cctagttaag ggatgagcct gaggtttatt   82560
tgataactaa gtgacttaat ggatgtactg gtaagagaga gaggaaacat ggagcaagtt   82620
tgaggggaaa aacagtgact ccgtttgtgc agctaattgc atatgtgggc ttgtgggtct   82680
ttcatttatt cataaacgtg ttgagaaata cctgctacct atctagtaaa gtaagagatg   82740
catcctctct taaaggcagt cagcttagag tctggtgatt tgaattgaca tgtccactga   82800
tagatgttga cactgtgaga ctggcggttc agtttgaggt ttcatcagca ttgccgatat   82860
tggagccatg aaaaaccaaa gaacagccag tgagagaaga gatctcagag aaaataaaat   82920
tgagaaagtg aaggacaaaa aatgttgtga agatagacca agattgatgg aatcagccat   82980
agagaggtca agtgggatga gaatgagcac gcatctgtta aactttgtgc ttaggagcag   83040
aatctaaggg aagggacagt ccagaggtta gaactcaggg taagatggaa gaacaggggc   83100
atctgggagt gaggcagttt ggtttagtgt agaaccttt tgtaacaagc attcccttct   83160
gtctagatga cttttagata tgtttcattg gcttggtacc ttttagaata aaatgattta   83220
gaggatctct cattttcagg gaaaataaat atattcctcc tggacaaaga aatagagaag   83280
tcatatcctg gggaagtggg agacagaatt caccgcgtat gggccagcct ggatcgggct   83340
ccatgccatc aagatccact tctcacactt cagatttcaa cccgaattct ggttcagacc   83400
aaagagtagt taatggaggc aagtattttg accagacttg tcaatatcat tgataaaata   83460
gttttctaaa tacttaaaat acttaaaata gtttacataa ctgatatgaa tgtgcacttt   83520
aatgatttgg tgagtagctt tcacttcagc attacttaaa attggctttt gtggatatta   83580
aattagtaaa acattgtata tgtcattgac atatatatta tttagcatga tgaaatattc   83640
atgatgtact aagataaagt gctacattta acccaagaca atcacttggc caaaaacact   83700
tcacatataa agaaattgga aactttgggt aggttctcaa ttttaaaaac actggataat   83760
aaaatttttt agacataatt tatatggaaa attctaacct atgtgcaaca ctgtggttaa   83820
tatagatcaa ttttcattat ttgtttctat attatgctta cttcaagaaa ggatctgagg   83880
taacttataa tacaagacat gatcaagagt catgtgaaga aagtgactag agaaatttgc   83940
ttaaaaaaca acaaaaacaa cccttagtct aagggtggat gttacagttt agcaacttaa   84000
gtaaagaaaa cctgaatctt tagtaggaag acattttttta ctctacctct aaatctaggt   84060
tgaatatatc ttgtaggttg tggatctttt ccataaatca gggatactga acaacagttc   84120
tatggatggt atggaaatag taatagcaat agtatgttac taactttgtg ggaaaagagt   84180
```

```
ggacattcaa ttttagctat ttaaatttgg aaagttagat gaaaatagag aacactaagt   84240
ttccaatttc atttgttttc attgagtctt ttctccagaa ttcctctcca aatggacact   84300
cttgagtatt ttcagtactt aatattgggg gtgaaatttc tttgctcact gaggaaagat   84360
tttagttgtt tataaacaga atttaaagt taaaaaacct gaaggggct gagaaatata     84420 tgatacttaa gtgtgtggaa ccctatggag aggagacctg gactgtttga taagattaag   84480
gtaagtgata tgtaatgtta aatactagct gtatctttac ctaggcatat ccatcagtat   84540
aaatttattt ggtgatgact gctttgtagt tgcagtattt attaagcagt cgcttagata   84600
agtgtttaac tgtataaatt atttagaagg tctccctttt tctagtttaa tgaggtcaag   84660
actttttttt tgaaatagca atgaatatta tcatttgata ctcacaggag tcacaaactc   84720
tagaagagta atgttttatt tctacttaaa tgggacttgc ttaataagat tccaaactga   84780
gttctgggtt caagtgtaaa cctgatgaaa atcatagata attgtaagga accagcattt   84840
ctaattggat ataatagcta ctgcttattt tcgttatgcc tcagagttaa aactaataca   84900
gtaaataatc ttactcctga gtaggaatta ttgtgattta ttatgtgaaa ttatctagtg   84960
tatgttatat tccttttaaac aaccagttac tgagaaacag ttatagaagc aggattaata  85020
ggcaaagtct taactgtctt cttcaatagt gtgtatagat cctaattaac cctttgggaa   85080
cgtgtattca tttaaacaga cttaatctta aggaggttaa agtaaaatgt gaatttatgt   85140
cagttaagtt atgctaaaac ttatcacaaa tcaaatgact gtcctcaaag ggttaaaatg   85200
tacaagaaat catttttgtc atttttacttt ttttctgttt actttttttcc ctcattttt   85260 tctttagttt ttatactttc cttcatatca tttgttctgt caggtgttcc ctggccatcg   85320
ccttgcccat ctccttcctc tcgcccacct tctcgctacc agtcaggtcc caactctctt   85380
ccacctcggg cagccacccc tacacggccg ccctccaggc cccctcgcg gccatccaga    85440 ccccgtctc acccctctgc tcatggttct ccagctcctg tctctactat gcctaaacgc    85500
atgtcttcag aaggtacaat accacaattt gttcatgttt ttgtttgtct ttgtttaact   85560
cctatgtgag tttataatta caaaatagtt tcctcttcat tatttaataa cctataattt   85620
ctgtgtttta acttagtttt attaaaacta tttctattaa cctttttgttc attagagaga   85680 aatttgataa atgtgtgaag ctataaactc tcttgaattg ttgttaaaaa gggggtttat   85740
ctctgcctga taattatgct tctttacagc cccagaaggg tctgccccac agccttcccc   85800 ctccttatt gcactgtata cagtagttaa acaaatgaac tttcttcagc cagtcttgaa    85860
cttaggttca ttttacagct ctttggccaa ggtcctagtg aaccttccta ttggccataa   85920
gcagggatgg tgttttctgg gtcttttttg agagcgacag cccatgtagc tgactttgcg   85980
tgtctgccct tagattaaag tagttgattt ttagaatgcc agaagaattc taaatttaac   86040
tgagtaattt ttttaaagtt agctttgcaa tcttacatag tgaaaggctg ctttaatctg   86100
gaagaagtcc ttgatctgag ataaaattga taaaaacgac atatgaattt gaatatttag   86160
ctatttcttt cctcgtcaaa aataagaata aaatcttgta attcttattc agtatttggc   86220
gctaaatcca tcattgccac atatcaaata cagggatatg ttgtagaaag gtaacattct   86280
aatttaaatg ccacccatat attaaaaacc tgttttctga atcataatgt ccttttgata   86340
ctagttctga atatttgtgt taaaattta atctgatttg ttcattaaaa ttagttaata   86400
ttgcttatgt tgggactaat aaagttttcc gcacaaaatg tgtttctcct gcttccctgg   86460
agaaaactgt attggctact tttaaataaa ttgttaccat ctaagcaggc aggtcatatg   86520
```

```
actttgactg aagcatctaa ccttgaagag caagttccac tgattttcaa ggtgacttct    86580
ttgctcaaaa gggccttaat agtggtcact aaatgcaaaa ttctgttgat atttttcttg    86640
tagtccatca tttgagtaag cgatgtttat ttaatgagaa tatattaaat aaaacatgat    86700
cattaatgac tgtgaacatc tttattacat taagatttaa ggactgctca tgtattaact    86760
tcacacagaa atatactttc tgtgtcattc agagatgttg aatatttcca tttgaaaatt    86820
atagtgtata acattagcat tcttctaaag atcatgttcg tgtttaaatt cctgttggaa    86880
gccaggcatg gtggctaacg cctgtaatct cagcactttg ggaggctgag gcaggtggat    86940
cacttgaggt caggagtttg agaccagcct ggccaacatg gtgaaacctc gtctctacta    87000 aaaatacccca gctacttggg aggctgaggc aggagaatca cttgaacctg ggaggcagag    87060
gttgcagtga gttgagatcg taccactgca ctccagcctg ggcgacagag acagactctg    87120
tcttataaaa ataaaaataa aataataatt ctattggcaa catatattaa tttgaagttc    87180
taaagagttt ggcagccggg tgagagagtg aggagatttg gctttgacat tagggaagtt    87240
ttcgcttggt gttaacacca gtaggcttct ctgatgaggg ccattctgtc cactcttta    87300 cctgatagat tggtctaatg cacagtagac tgatttagaa agagtagtca ctagtggcat    87360
ggcagaatca ataatgtaga attttgacaa ttcatatagt gctgatttct cccccaaatg    87420
tcagttattt tggtcatcta ttaatagact aatacaagtc atccctttaa tagaattttc    87480
agctcacagc ctgctaagcc taagaaactg cttacaggtt actgcttact gttttaagcc    87540
gagttttaaa attgatgatc atgatagaag agataaataa actaaaattt tagagaaatt    87600
taagaagggt atgtacatat gttttagtgg tatcggggtg tatagggatt aatagtcttc    87660
tgtttaaatt ttttttttct aattttagaa gtaatgtaga aaattcgggt cagggaaagg    87720
taaaatatat ggaaagttaa aaatattta tcatgtagtc ataatttcta gtaacatatt    87780
tctttacaaa taagacatag ttgaaacaga ttgctacagt tctttaaga gttgacatct    87840 tattgttgat ttcttaccac caacttcatc cctcccttc tttaaaaata aagggaaata    87900
ataaaattta tttataaaac tttgtggcat tccacaaaat aattctgaaa gaattagtat    87960
ggccaaaaaa atatgtatgg tgtttttttt ttttctattt ttaaccaagg aaaaactgta    88020
gagtgagtga gtgtgtgtgc atgtgtgtgt gaatgggtgt atttagcaga aaagtagtac    88080
tgatgaatat catggaattt atgtgatgtt cactgtttct tccttagggc ctccaaggat    88140
gtccccaaag gcccagcgac atcctcgaaa tcacagagtt tctgctggga ggggttccat    88200
atccagtggc ctagaatttg tatcccacaa cccacccagt gaagcagcta ctcctccagt    88260
agcaaggacc agtccctcgg ggggaacgtg gtcatcagtg gtcagtgggg gtaggtaaca    88320
cttgggcata atgatggtac tcattttgtc attacactag atataaagag ggctgagcta    88380
caactctgtt tgaggaagtg taagtatgta tatgttaaaa atagtagaat caccaggaat    88440
tgggaaaccc atatttttat tctgggctct accacttatt catcatatat taaagcaagt    88500
cagacactca ttctgaagtt gagatttcgc agtgagtaaa gtgttaataa ttcttgccta    88560
gtctacatta tgggattgtg atgagattcc tataaggttc ataaatacag atatattgta    88620
aaactataaa gttttgtaaa gtacctctct aatatgaggc aaaacagta tgtaacacta    88680 tttggaggga ccgtatttcc ttatcttttt agcagctttg tttatcagta cattctataa    88740
acatttattt ttggcttaca ttgtagtgtg tttctatagc atctgtatat ggcactaatt    88800
cccaactata tttccataat aaggaatatc aaatacaaat aaagggtcca agttttattt    88860
gtgattagca taaggaatat gctgacagca gctataaaag tataaaaatt aggctgggtg    88920
```

```
tggtggctca cgcctgtaat cccagcactt tgggaggctg aggtgggcgg atcacaaggt   88980
caggagatcg agaccatcct ggctaacacg gtgaaacccc gtccctacta aaagtacaaa   89040
aaaaattagc cgggcatggt ggcgggtgcc tgtagtccca gctacttggg aggctgaggc   89100
aggagaatgg catgaactcg ggaagcggag cttgcagtta gctgagatca cgccattgca   89160
ctccagcatg gcaacagag caagactctg tctcaaaaaa aaaaaaaaaa aaaaagttta    89220
aaaactagac gttgacatga ttttacaata aggctgactg cttttgctac tttgccaatc   89280
agtccttagt gctttgttcc cataactgtg gtaagcaaga gcttacaaag aatacttaaa   89340
acaaacaaac aaacaaacaa aaaaaacact ttttctcttt taatcagtcc agagaacctt   89400 taaagaaac aagatcggcc agttgctgtg gctcatgcct gtaatcccag cactttggga    89460
ggctgaggtg ggtggatcac ttgaggtcag gagttcaaga ctggcctgac caacatgatg   89520 aaacccatc tctactaaaa atacaaaatt agctgagtgt ggtggctatt tgagaggctg    89580
aggcaggaga atcatttgaa cccaggaggt gaaggttgca gtgagccaag atcacaccat   89640
tgcactccag tctgggtgac aagagcgaaa ctctatctca aaaaaagaa aaaagaaaca    89700 agatcttcaa gcttaaggaa acaaaaacaa aactcagctg tgttaaatct gtttttagtt   89760
gctatacatt tctgctcagc ttcatgtgat gcacattcat gtaattgtat cctaaattcc   89820 tttgtactt ttattttctt ccttggtctt caattatctt aagactacca agaaaacaaa    89880
aattttaaaa atcttcttca gccggtcagg cgcagtggct cacggctgta atcccagcac   89940
ttggggaggc tgaggcgggt ggatcacgag gtcaggagtt caacaccagc ctggccaaca   90000
tggtgaaacg tcgtctctac taaaaataca aaaattagct gggcattgtg gcgcgttctt   90060
gtaatcccag ctgctcagga ggctgaggca ggagaattgc ttgaaccagg acccgggagg   90120
tgtaggttgc ggtgagcgga gatcgcgcca ctgcactcca gcctgggcta tagagtgaga   90180
ctccatttca aaaaaaaaa aaaaaatctg cttcagctat tctgttaatc ttttgacatt    90240
acttagatgg tctggaaata aattttgaga ataacatgat tagaagtgag agagtataag   90300
catagttttg gagatacact cagaatagca ttatagattt tctcttttta ctaattggaa   90360
aaatggcagt tgttgaataa tagttttctt ccgtgaccct tgtgacttaa aaaaaaaaa    90420 acactgaaat gaaataatcg aaccattttc tctaaaccct tgaatctgag ctctgcagtt   90480
aggtttataa tggtatatga aacctattag atatatactt ggaagtcata tgggatacaa   90540
accctgcttt tattatcttc ccctttgac taacttgggt ctcaagtttc cttaattact    90600
gcacagtgga ccttgatgtt gctataaaga atgtgtaggg ctgggcatgg tggctcatgc   90660
ctgtaatccc agcactttgg gaggccaagg taggcagatc acctgaggtc aggagtttga   90720
gaccagcctg gccagcatgg tgaaacccg tctctactaa aaatacaaaa aaattagctg    90780
gttgtggtgg cgagtgcctt aatcccagc tactccagag gctgaggcag gagaatcact    90840
tgatacattt agttaggaga gaaaatcata cttatgttag taattgctgc tgttcttcat   90900
atacttgtgg ttttgattgc cagcaaattc ctaacatttt ggaaagaaa acagtaatgg    90960 gataaagggt aagggctaga gaggacagtt ttatttacct agatcttcag agaagcctga   91020
agcctctttt aggaagtaac atttgaactg agaatgtaat aaatacatt tccctttctt    91080 ctagttccaa gattatcccc taaaactcat agacccaggt ctcccagaca gaacagtatt   91140 ggaaatacccc ccagtgggcc agttcttgct tctccccaag ctggtattat tccaactgaa  91200
gctgttgcca tgcctattcc agctgcatct cctacgcctg ctagtcctgc atcgaacaga   91260
```

```
gctgttaccc cttctagtga gggtatgtaa caaagggctt ctggatccat aatctcagct   91320
gtgaaattga atgttagagg gtgatattat atgaaaaaat tctaggttat ttttattcat   91380
agacaagtat ttttagtgca catttaaaag tttatgtaaa ttttgatgtt gtttaatact   91440
actaatttaa tatagtgtct gtgttacaaa ggttaacatt cctgggtgtc aaatacctac   91500
ataaataaaa ttattggtgt ttcatatgac atctgcaaag gaaaaaaagc ctctgtttaa   91560
atgaaagcat tattttccaa aaacatagga aatcaaaatt attgttcagt gttttcttgt   91620
tttgcttttc taacttatct gaattttttt taaaaaattg ttttctagct aaagattcca   91680
ggcttcaaga tcagaggcag aactctcctg cagggaataa agaaaatatt aaacccaatg   91740
aaacatcacc tagcttctca aaagctgaaa acaaaggtta gagtttaaag agtcattaag   91800
cttaactgta ggaataggaa gaagtatgtc taatttcatg cccatacaga atattttgt    91860 tcaacatttc ttcttactat tgtgatagat aaatgtattg cttgacaaat tccaaaatcc   91920
aaatttaata tttgaaatta ttttctgatc ttatatctta ttctaatttc tatcatctca   91980
tactaaaaag aatgtgatgt taaagtttaa aaataaacct gtgtcttaac agttcttaat   92040
tttacaggta tatcaccagt tgtttctgaa catagaaaac agattgatga tttaaagaaa   92100
tttaagaatg attttagggt aagtattgta ctaactgatg aatttgagtt ttagaaaata   92160
agcattacta aagatttatc tatttataaa aatgcgttat gtatacagtc agaaacatca   92220
aaccatatat gtagaaagca gaacattttt aaagtggtct ttgcctatcc tttaagtggg   92280
ataactaaaa tcatgagatt tggtaacaac aatatgtagg tatcaaatga gagtatagcc   92340 ctgcacatttg aaaccaccat agcacagctt actatttgat ggtcatttgt actttgttca   92400
gtgaagctag atattagtag agcaaggcca agtcattaat aatctagtgt ggcaaatgga   92460
agatgtactg gactctggtg ttctgaggta gttggagatt tatactttgt acacaaatat   92520
attgtggtca aaatctttct gtaacattat ttctctgtct tagcacaggc tttacttaac   92580
atctctcctt gattgtcatt tcattctttt gcatgttatt tactataggt atcgaggtag   92640
attttgagac caaccaataa atcttcttga aacttagctt cttagaaagg aaaatctaaa   92700
taccagcctt ttaaaaaaag tagctgaatt aaaggatgag tgaaccaaag gcaaaggtag   92760
cctttcctca gcctgtgttt tagctttcta aatgttaaca atagcttcat tcttgactta   92820
ttggtaacat tcaaaatact acttattatt tcatacttta gcacatgtat ctattcagct   92880
ttaatgctat taacagttgt taacctaagt tttcatttgt tggcgggcac ggtggctcac   92940
acctgtaatc ctagcacttt gggaggccga ggtgggcaga tcacctaagg tcaggagttc   93000
gagaccagcc tggtcaacat ggtgaaaccc tgtcttgacc aaaaatagaa aaattagcta   93060
ggcatggtgg cgcacacttg taatcccagc tacttggcag gctgaggcag gataatcgct   93120
tgaacccagg agacagaggt tgcagtgagc cgagatcaca ccactccact ccatcctggg   93180
cgacagagca agactgcatc tcaaaaaaaa aaaaaaaaa aaaagttttt tcaatttgtt   93240
aaacaatagt taacacatac aaatgataca aagaatattg aatatgatca tgtgcccact   93300
acccagctta gtaaataaag cattctaaca cagttaaact cctcttatgt atctgcccct   93360
cctcagctgc ttcccctgt ttccttccaa aaggaagggt ttcttttctg tgcagttctt    93420
tatatttata ctgcatatga atatatctgt gagcaataga tgatattttg cataatctta   93480
aatttgctat aaagtctttt ttttttttt aattgatcat tcttgggtgt ttctcgcaga   93540
gggggatttg gcagggtcat aggacaatag tggagggaag gtcagcagat aaaaagtgaa   93600
caaaggtctc tggttttcct aggcagagga ccctgcggcc ttccgcagtg tttgtgtccc   93660
```

```
tgggtacttg agattaggga gtggtgatga ctcttaacga gcatgctgcc ttcaagcatc    93720
tgtttaacaa agcacatctt gcaccgccct taatccattt aaccctgagt gacacagcac    93780
atgtttcaga gagcacaggg ttgggggtaa ggtcatagat caacaggatc ccaaggcaga    93840
agaatctttc ttagtacaga acaaaatgaa aagtctacca tgtctacttc tttctccaca    93900
gacgcagcaa ccatccgatt tctcaatctt ttccccacct ttccccctttt tctattccac   93960 aaagccgcca ttgtcatcat ggcccgttct caataagctg ttgggtacac ctcccagacg    94020
gggtggtggc cgggcagagg ggctcctcac ttcccagaag gggcggccgg gcagaggtgc    94080
cccccacctc ccgacggggg cggctggctg ggcgggggct gacccccccac ctccctcccg   94140 gatgggcgg ctggccgggc gggggctgac ccccacctcc ctcccggacg ggttggctgc     94200
cgggtggaga tgctcctcac ttcccagacg gggtggctgc caggcggagg ggcttctcac    94260
ttctcagacg gggcggctgc cgggcagagg ggctcctcac ttctcagacg gggcggccag    94320
gcagagacgc tcctcacctc ccagacgggg tcgcggccgg gcagaggcgc tcctcacatc    94380
ccagacgggg cagcggggca gaggcgctcc ccacatctca gacgacgggt ggccgggcag    94440
agacgctcct cacttcctag acgggatggc ggccgggaag aggtgctcct cacttcccag    94500
actgggcagc cgggcagagg ggctcctcac atcccagacg atgggtggcc aggcagagac    94560
gctcctcact tcccagacgg ggtggcggcc gggcagaggc tgcaatctcg gcactttggg    94620
aggccaaggc aggtggctgg gaggtggagg ttgtagcgag ccgagatcac gccactgcac    94680
tccagcctgg gcaccattga gcactgagtg aacgagactc cgtctgcaat cccggcacct    94740
cgggaggccg aggctggcag atcactcgcg gttaggagct ggagaccagc ccggccaaca    94800
cagcgaaacc ccgtctccac caaaaaaata cgaaaaccag tcaggcgtgg cggcgcgggc    94860
ctgcaatcac aggcactagg caggctgagg caggagaatc aggcagggag gttgcagtga    94920
gccgagatgg cagcagtaca gtctagcttc ggctcggcat cagagggaga ccgtggaaag    94980
agagggagag ggagaccgtg gggagaagga gaaggagggg gagggggagg gggggagagg    95040
gagagggaca atgatgtctt gctgtaggta ttcttcccca tttgaatttt ttcctcagca    95100 ttatttttt taacatcatt cagtctcctc ttatactaca cttggattga atttaatatc     95160
tcatgaagaa aaaacatttc tactttgaag catgtgaatt agcatgtttt tataacagct    95220
ttattgagat ataatttaca tatataaata aaccgtttaa agtgtataaa tcagtggttt    95280
ttaatgagat ataatttaca tatataaatc aaccatttaa agtgtataaa tcagtggttt    95340
ttaaaatatt cacaatgttg tacaaccgtc ttctcagttg attttaaaac atactcttca    95400
cccccaaaag aaacccccgtg cccagtttag cagtcgttcc acatttgcct ccagcccttc   95460
tctttcccct actcccaacc ctaagcaacc gttaatctac tttctgtctc tatggatggg    95520
cttatttggg gcaaattcca tttcatacaa atggaataat aaaatatgtg cttttatga    95580 ctggcttctt tcactcagag tagtgttata aaagttcatc catgttggag catgtttcag    95640
tacttcattt ctttttgtga ctgactaata ttccttgatg tggataatac cacatttgt    95700 ttatccatta atcagtttgt agctatttgt ggtgttctca ctgtttgact attctgaata    95760
acactgccac aaacatgagt gtgcagtttt tttctcgtcc tatcttttca tttcttttgt    95820
gtacctacct aggagttgaa ttgctgggtc atatggcaac tgtgtttaac cttttgagga    95880
actaccaagc tatttgccaa gatatctaca ctattttaca ttcccaccag cagggtatga    95940
gggtttctgt ttctccacat ccttgctaac acttattgtc ttgtctttttt tgattatagt    96000
```

```
catccttgtg ggtgtgaagt gttaacctca ttgtggcttt aatgtgcagt tctttcatgg    96060
ctaatgatgt tgaacatctt ttgtgtttat tggccattta tatatcttct ttggattgat    96120
gtctgttcaa atctttaccc attttaaaaa ttgagttgtc ttttattat  tgggttgtgg    96180 gagttcttta tatattgtgt gtacaagtcc ctgttagata catggtttgc aaatgttttc    96240
tcctgttctg ttggttgtct ttttactttt tcatcccttg aagcacaaaa atttttaatt    96300
ttgatgaagt ccaatttatc tgattttgaa gtaagctttt ggtgtcgtat ctaagaaaat    96360
actgtttcat caatcattaa ggtttattac tcttctgggt ttttttaaga attacattta    96420
gaggtgtgat ccatttggag caactttttt tttcttttga cacagaatct cgctcttttg    96480
cttaggctgg agggcagtgg tgcaatcttg gctcacagca gcctcagcct cctgggctca    96540
aatgagtagc tggtactaca ggtgtgcacc accacccttg ctattaata  acttttgtat    96600 ttttttgtag agacagaatt cgccatgtt  gcccaggctg tctcaaaca  cttggactca    96660 agtgacacgc ccacctcagc ctcccaaagt gaaaaattgc tttcaccttg cactgcggac    96720
tcgccctgaa ttctttcttg tgcaagatcc aagagccctc tctggggtc  tggatcggga    96780 cccctttcct ataacaatat tatgagaata acatttgatt ttttttaagt gaaacaaatt    96840
gttattaaaa aattaaaaaa ggtcatagga gagtgacttg gtgctcagcc cattttgagc    96900
agttatttaa tatagcataa ggtggggttc aaattcattc tttatattaa ttttttattt    96960
ctaattgaca cataaccata cacttataac cattttact  gtgtaagttc agattcattc    97020
ttccgtatgt aggtattagt tgtcccagca ccatctgtta aaaagactat tcttggccag    97080
gcacagtggc tctcaacgcc tgtaatccca gcactttggg agtcccaagc aggcagatca    97140
catgaggtca ggagttcgaa accagtctga ccaaatggtg aaaccgcatg tctactaaaa    97200
atacaaaaat tacctgggtg tggtggcgca cacctgtagt ctagtcccac tactgtagtg    97260
gctgaggcag gagattcgct tgaacccagg aggtagaggt tgcagtgagc tgagatcatg    97320
cactccagtg tgggcgacag agtgagactc catctcaaaa aaaagactat tctttcctcc    97380
attgaattat cttcacatgc ttgttggaag tctgttgact acaaatgtga agtttatta    97440 ctggactctg aattgtcctc cactgaatct ctatgtctta tccttatggc agtaccatac    97500
tgtcttgatt agagttactg tattttaaaa ggctgtactt tttcagttag cagaaaacat    97560
tttagctatc agcacaactt tctgtaaacc ttcattaatg cttgacttaa attccaagaa    97620
ggagcaacat aaaaagtctt atctctttag gagttttagt cttactactt ttaggtgcct    97680
gaataaccaa atgtattatt tagcctctta ctaataactc cttgatccat aggggcatac    97740
caggaagaaa agaagtggtt tttaaaaaat gagagtgggc cgggcacggt ggctgatacc    97800
tataatccta cactttggg  aggctgaggc gggtggatca cttgaggtca ggagtttgag    97860
accagcctgg ataacatggc gaaaccctat ctttattaaa aatatataaa ttagccgggc    97920
atggtggcac atgcctgtaa tcccagctac tcaggaggct gaggcaggag aatcacttga    97980
atccaggagg tggaggttgc agtgatccga gattgcatca gtgggcgaca gagcgagaat    98040
ctgtctcaaa gaaaaaaaaa gagagtggaa aaaaaaaata tgtgtcccag aacttaaatt    98100
ttaattaaaa aaaataaaa  gagtgaactt tctaattgtt ctcttcagat aatataatgt    98160
tattctctta tgttttattg cgtatttcct gtgtaccaga tgctgttctt catgcttgta    98220
tgttaaatct tgtctaacat ctctgtcaag caagttctgt ttgtatctgc actgtgtata    98280
ttaggcagct tgggcaaaga gaagttaagt aatctgccca aactcacatg gctagtaagt    98340
aagagggctg accatctggt gtttaagctt ctagcagtgc tttgaatagt aactaatgca    98400
```

```
tagtgcatgc tgcactgtca gtcagtgatt cattagagct aacttcatga catgctcata   98460
gccccaaact gcatttgttc acaaatatct gtagtccttc atttaggcag aaatagaaat   98520
accttgtgtg tttgttgttc cttccctttt gagccatatg cagagtgctg atagctttat   98580
ttgtgtaaga attgctagta atttgatctg ttttgggtta ataatgtggg ttttagaggt   98640
aaatggacct aggtttgaat gttggcctct atacatcatg tgcgtaacat tgtggcatgc   98700
tatctacttc ccccaagcca aaatgggtta atttagaac ctgcttcata gtgttcctgt    98760
gagagctcga tgagatattg cctataaagt gtttagcata gtgcctagca catggtatgt   98820
attcaataca tgttcattct tactagcaaa atatagatga cccagtattg tacagagtat   98880
gtacaatggt gtcattgtac catttcatgt ggagtcacat aagaatttca gttttctgct   98940
gggcatgatg gctcactcct gtaatcccag cactttggga ggctgaggtg gatggatcag   99000
ctgaggtcag gagttccaga ccagcctggc cgacatgatg aaaccccatc tctactaaaa   99060
atacaaaaaa ttagccaggc gtggtggcag gtgcctgtaa tcccagctac tcgcaagact   99120
gaggcaggag aaatgcttga acccgggagg cggtggttgc catgagttaa gatcgtgccg   99180
ctgcactcca gcctgggcaa taagagcgaa actccgtctc aaaaaaaag aaaaaaaag    99240 aacttaagtt ttccattaga tttagtatag tgcagagagg aaatacagca gagtgctata   99300
ttccatatat agcaatatag cattagaaca atatattcca atacagcaga gtgctatatt   99360
cagataccaa ctagtggact tgctatttgt aagatggcaa taatagtatc tacatcaaat   99420
agggctgttg tgaagactaa atgaataagt ctataaatag tttagaacag tgtctggaca   99480
ggtacagtgg ctcatgcctg aatcttagca ctttgggagg ctgagacagg tggatagctt   99540
gagctcaggc attaaagacc aacctgggta acatggtaaa accctgtttc tacaaaaaaa   99600
tacacacatt agccaggtgt ggtggcacat gctaatagta ccagctactc aggaggctga   99660
ggtgggagaa tcacttgagc ctgggagatg gaggttgcag tgaggtgagc ttgcaccact   99720
gcgctccagt ctgggcaacg gagtcagacc ctgtttggaa aaaaaaaaa aagtgtccaa    99780 cccatagtaa gaaatgcaga tgtgtttgac attgtaagaa aaagcaacac caaaagtctg   99840 attttttgcct tcactcaaga actcttatga taattaaact ccgaagtcct tggcaatata   99900
tatagttggt ctgttatgtg gatcgcctct actaaagatt tttgtgaaca atgaaagtt    99960 taagtagtaa gttcctacat cgtgacttaa attgccagtg tgcccacata aatacccctgt  100020 caacatttgc ccttagccac ttgactcttt agctatattg gtaatgcagt aaagcttgcg  100080
atgcgccaga gttgcataat gctgtttgcc atgacaccaa gagccttggt aatgaaacca  100140
ttgaaattgg tttgcctata ctgaggctga agaggtatct tggctctcta attttaaggc  100200
aacctttttg gctgtgtagg tttctctta gcttgtttct caccacctgg ggctgtggct   100260
taggtccgtt gtcctaacct gtggcttagg ttctgttttt gttgcttgta cttgctcccc  100320
cttttttcag ccattcctgt tttctttctt ttgtagagga tgccatctta aatcatcttc  100380
agccagtggt agcatttat ttttttctggt ctgcaaactt aaaaacctca tcacttattt   100440
tgctaatatc tttgtcttct gttctttttg atggtccttg gttttgcagt ctactttaaa  100500 ggttttatt ttttatggg tacatagtag acgtattatt cataggggtct gtgagatatt   100560 tagataaagg catataatgt gtaataatca cattagggta aatgggggtat ccatcaccat  100620 catcattcat catttctttg tgtaatgaac gttgcaattg tactccctca gttattctaa  100680
aaagtacaac aaattaatgc tgactgtagt caccctgctt tgttgtcaaa tactagatct  100740
```

```
tattcattct ttatttaact tttaaatttt taaacttatt ttatttattt atttttagac 100800
ggagtctcac tctgtcgcca ggctggagtg cggtggcgca gtctcaactc actgcaacct 100860
ccgcctccag ggttcaagtg attctcctgc ctcagcctcc tgactagctg gaactacagg 100920
cacgtgccac cacgcccagc taattttgt attttagta gagacggggt ttcactatgt 100980
tggctgggat ggtcttgatc tcttgacctt gtgatccggc tgccacagcc tcccaaagtg 101040
ctggggttgc aggcgtgagc caccgtgccc ggcctttaaa attattttaa atcatttaa 101100 tatcttttc atttctgcct ccggtcctgc agagttctta ttcgttcttt ctaaattttc 101160
tttgcaccca ctaatcacct catttcctt cttctcccca ttacccttcc caacttctgg 101220
taaccattct gctatctcca tgtgttcaat tgtttttatt tttagtgcct gcaaacgagt 101280
aagaatatgc aaagtttatc tttctgtccc tggcttattt tacttaacat aatgtcctcc 101340
agtgccatct acattgctgc aaatgacagg atctcattct tttatggc tgaatggtaa 101400 tctattgtgt atatatacca cattttcttt ctccatttgt ctgtcagtgg acacgtaggt 101460
tgattccaaa tcttggctgt tgtgtatata gtgccgtagt aaacatggga gtgcagatat 101520
tccttcaata aactgattc ctttctgagt atatacctag cagtgcaatt gctggatcat 101580
atggtagctc tatttttagt ttttgagga atttccatac tgttctccat agtggttta 101640 ccaatttaca tgtccaccaa cagtgtgtga aggttcccct ttatccacat cgttaccagc 101700
atttgttatt gcctgtcttt tggataaaag ccatttaac tggggtgaga tgatatcttg 101760
ttgtagtttt aatttccatt tttctggtga tcagtagtat tgaataccttt tcatatacct 101820 gtttgccatt cataaataac gatgaggtct tgctgtttgg cccaggctgg tctcgaactc 101880
ctgggctcaa gcaatcctcc caccttggct tcccaaaatg ctgaaattat agttgtgagc 101940
cactgcacct ggccttgtat gtcttccttt tttttttgtt ttgttttgtt tttgagacag 102000
agtctcactt tgttgcccag gctggagcgt agtggtgtga tcttggctca ctgcgcccta 102060
cacctcccgg attcaagcaa ttctcctgcc tcctgccacc atgtctgcct aattttgta 102120 tttttagtag agacgggatt tctccttgtt gcccaggctg gtcttgaact cctaacctca 102180
ggtgatttac ctgcctcagc ctcccaaagt gctaggatta caggcgtgag ctgctgcgcc 102240
cagcctgtat gtcgtctttt gagaaatgtc tattcagatc ttttgcccat ttttaattga 102300
gttactaaaa ttttccctat ggagttgctt gagtgccttt tatattctgg ttattgatcc 102360
cttgtcagat gagtagtttg caaatatttt ctcccattct gtgggctgtc tcttcacttt 102420
gttgatggtt tcctttgctg tgcagaagct ttttaacttg atgtgatccc atttgtccat 102480
ctttgctttg gttgcctgta cttttgggt attactcaag aaatctttgc ccagagtaat 102540
gtccctggga gtttaatgtt ttcttttagt agtttcatag tttgaggtct tagatttaaa 102600
tctttagtcc attttgattt gattttttt taatatggtg ggacacaggg gtctggtttc 102660
attcttctgc atatggatat ccagttttcc cagcaccatt tattgaagag actgtccttt 102720
ccccagtgta tgttcatggc ttcttgtgg aaaatgagtt cacttagacg tatggattca 102780
tttctgagtt ctctgttctg tttcattgat ctatatcttt ttttatgcca gtaccatgcc 102840
attttggtta caataatttg aagtcagata atgattcctc ccgttttgtt cattttgctc 102900
agtatggctt ttgctctttt gggccttttg tggttcccta caatttttag aattattttt 102960
gtctacttct gtgaggaatg tcattggtat ttgataggg attgcactga atctgtagat 103020
tgctttgagt attatcaaca ttttagcaat attaattctt ctaatccata aacatggaat 103080
ctcttttcat gttttttctg tgtcatcaat ttcagtgttt taaagttgtc attatagaaa 103140
```

```
tcttttactc atttggttaa gtttattcct aagtattta ttatatttgt agctattgta    103200
aatgggattg cgtttaaaaa attttcaga ttgtttgctg ttaaatataa aaatgctcct   103260
gatttttgtg tgttgatttt tgtatcctgc aattttactg aatttgtttg tcagttctaa   103320
taggttttc ttttttggag tctaggtttt tccaaatgta agatcatatt atctgcaaac    103380
aaggataatt tgacttcttc cattccagtg tggatgcttt ttattctt ctgttgtctg    103440
attgctccaa ttaggacttc cgagtattat gttgaataac aatggtgaaa gtgggcatcc   103500
ttgtcttgtt ccagatctta gaggaaagcc tttcagtttt tccttttca gtatggtact   103560
agttatgggt ctgtcatata tggcttctgt tttgttgagg tatattcctt ctatacccag   103620
ttctttgggg ttttttttgtt tgtttgtttt tgagatggag tctcactctg tcacccaggc  103680
tggagtgcag tggcgcaatg ttggctcact gcaagctcca cctcctgggt tcatgccgtt   103740
ctcctgcctc agcctcccga gtagctggga ctacaggtgt ccgctaacac gcccggctaa   103800
ttttttgtat tttagtagga gacgggttt caccgtgtta gccaggatgg tctcgaactc   103860
ctgacctcat gatctgcccg tctcagcctc ccaaagtgct gggattacag gcgtgagcca   103920
ccacgcccgg ccaagggttt taatcataag gggatgtggc atttttatgtg atataaatta   103980
tatatttata tcatgtgata tatatttata tcatacacag tataaataat atatatatat   104040
attttttagt ctttgtcttt tattctgtta agatgtacca tgtttattga tttgcgtatg  104100
tcgaaccatc cttgcatccc tgggatgaat cccacttagt catgatgaat gatctttta   104160
atgtgttact gaattcggtt tgctagtatt atattgagga tttttgcata atgttcttca   104220
gagacactgg cttctagttt tcccttttg atgtgtcctt tggttttgta tagggtaata   104280
gtggccttgt agaatgagtt tagaagtatt ccctcttcct gtattgtgtt ggaatagttt   104340
gagtaggatt ggtattagtt cttctttaaa ggtttagtag aattcagcag tgaagccatc   104400
aggtccatgg cttttctttg ctgggagact atttcttata gctttgatct cgttacttgt   104460
tattggtctc gttacttgtt attgtatttg ggttttggat ttctttgtgg ttcagtcttg   104520
gtaggttgta tgtgtctagg aatttatcca tttcttcaag gttttccaat gtatcagcat   104580
atagatgctc atagtagtct ctaatgatcc tttgaatttc ggtggtaaca attataatgt   104640
ctcctttttc atctctcatt ttattatttg ggttttctct ttttttctg agtctggcta    104700
aaggtttgtc agttttgttt atctcttcaa aacaatttac tgttttattg atctttttgta  104760
ttttcttcat ttcaattta tttatttctg ctttgatttt ttttattct tctactgatt    104820
ttaggttttg tccttgcttt tctagttctt taggatgtat tggcagatga agttttcca    104880
cttttttgat gtaggcactt actgctgtaa acattcctct tattgttgct tttactgtat   104940
cctataggtt ttgataagct gtgtttccat tttcatttgt ttcaaggaat tttccagttt   105000
tcttcttaat ttcttcatgg acccactggt cattcaggag catattgctt aatttcatg    105060
tatttgtata ctttccaaag ttcctcttgt tatctagtgt tattttattt tatttttatt   105120
tttgttttt tgagatggag tctcgctctg tcacccatgc tggagtgtag tggcgcgatc   105180
tcggcttact gcaacctctg cctccccagt tcaagtgatt cttctgcctc agcctcctga   105240
gtagctggga ttacaggcat gtaccaccac tcctggctaa tttttttttg tatttttagt   105300
agagagggg tttcaccatg ttggtcaagc tgatctcgaa ctcctgacct cagatgatcc    105360
acccaccttg gcctcctaaa gtgctggaat tacaggcatg agccaccgtg cccggcctct   105420
agtgttatct tattgtgatc agagaagata gttgatatga ttttaacttt tttgaatttt   105480
```

```
tatttattta tttgtttgtt tgtttgtttg tttgtaacag agtctcactc tgttacccag   105540
gctggagtac atgtcatgat cttggctcac ctgcaacctc cgccttcctg gctcaagcaa   105600
tcctcccacc ttagccttcc aagtagctgg gactacaggc acatgccgtc acatatggct   105660 gatattttg  gatttttttt ttttttgtag agatggggct ttgcgatgtg tcccagggtt   105720
gtttcgaact cctgagctca agcaatccac ctatttcggc ctcccaaggt gctgggatta   105780
cagacatgag ccactgtgcc acgtcaaatc tttagacttg ttttgtggct taacataggg   105840
tctatctttg agagcaatcc atatgttgag gagaagaatg tgtattctat agctgttgga   105900
cacaatgttc tgtaaatatg tattgggcct atttggtcta tagagcaaat taggtctaat   105960
gtttctttgt tgattttctg tctgaatgat ctgtccattg ctgagagtgg ggtgttgaag   106020
tttccgactg ttactgaggt ctgtttctct tttttgctct aataatgttt gctttatata   106080
tctggatgct ccagtattgg ttgcatatgt atttatactt gttataacct cttgccgaat   106140
tgatcccttt atcattatac aataatcttc tttgtctgtt tttatagact ttgtctcaaa   106200
atctatttta tctaagcata gctactcctg ttcttttctg gtttccattt gcatggaata   106260
ttgttttcca gctcttcaat tttagtctat gtgtgatttt ataggtaaag tgtgtttctt   106320
gtaggcaatg gatctttggt tttttttttt tttttttga  cagagtttt  tgctattgtt   106380 gcccaggctg gagggcaatg gcgctatctc agctcactgc aacctccgcc tcctgagttc   106440
aagcgattct cctgcctcag cctcccaagt agctgggatt acaggcgcct gccaccaagc   106500
ccagctaaat tttttgtatt ttcagtagag atggggtttc agtatgttcg tcaggctgtt   106560
cttgaactcc taacctcagg tgatttgcct gccttggcct cccaaagtcc tgggattaca   106620
ggcgtgagcc accgcaccca gccttttttt taaatccatt tagccactct gtatcttttg   106680
attggagagt ttagtcgatt tacattcagt gttgttactg attagtgagg acttaactac   106740
taccattttg ttacttatta tctggttgtt ttgtagtcct actccctccc ttccccttc    106800 ttttttactt cctcttcgct ccttttttcc ctccctccct tccttgtttt gaaagtgatt   106860
ttctctggtg gtatgtttta atttcctgct ttatatttt  tgtgtatctg ttgtaggtgt   106920
ttttgattta agatcaccat gacagctggg tgcagtggtt cacacctgta atcccagcac   106980
tttgggaggc cgaggtgggt ggatcaagag gtcaggagat tgagaccagc ctggctaaca   107040
tggtgaaacc ccatctctac taaaaataca aaacttagcc aggcgtggag gcacgtgcct   107100
gtaatctcag atactcagga ggctgaggca ggagaattgc ttgaacccag gaggcagagg   107160
ttgcagtgag tcaatattgt gccactgcac cccagcctgg gcgacagagt gagactccgt   107220
ctcaaaaaaa aaaaaaaaa  agagatcaca taagggttgc aaataacatt ttataaccca   107280
ttattttaaa ccaatgacaa cttgaaactt tgattgcaaa aacaagcaag caaagagaaa   107340
actaataaaa actctacact tcatctgccc gctttttaac ttttgttgtt tttatttata   107400
tctttattat actatgtctt aaaaaactgt agttataagc caggcgcagt ggttcacgtg   107460
tgtaatccca gcactttggg aggctgaggt gggcggatca cctaaggtca ggagttcgag   107520
accagcctag ccaatatggc aaaaccccct ctctactaaa aatagaaaaa ttagccggac   107580
atggtggcgg gtgcctgtaa tcccagctac tcggaggctg aggcaggaga atcacttgaa   107640
cccaggaggc ccaggttgca gtgagccgag agtgcgccac tgcactccag tctgggcaac   107700
agagtaagac tgtctcaaaa aacaatacaa aacaaaacaa aaccctggcc tagtggctca   107760
cgcctaatcc cagcactttg gaaggcaaag gtggggcgaa tcacaaggtt aggagttcga   107820
gaccagcctg accaacgtgg tgaaactctg tctctactaa aaatacaaaa attagccagg   107880
```

```
cgtggtggca cgcacctgta atcctagcta ctcaggaggc tgaggcagga gaatcgcttg    107940
aacctgggag gcggaggttg cagttagccg agatcgcgcc actgccgtcc agcctgggca    108000
gcagagcaag actctgtctc acaaaaaaaa aaaaaattgt agttcttatt tttgaaaggt    108060
tcatttttta ttcttcctgc tcaaaatatg agtagtagtt tatacaccac aattacagtg    108120
ttacaatatt ctgtattttt ctgtgtactt gttaccagtg agttttgca ccttcaggtg      108180 atttattatt gtttgttaac atccttttct tgcagattga agaactttt tttttttttt        108240 ttttttttga gacagagtca tgctctgtta ccagcctgga gtgcagtggt gccatcttgg    108300
ctcactacaa cctccaactc ccaggttcaa gcgattcttc tgcctcagcc tcccaagtag    108360
ctgggattac aagcatgtgc caccacgccc agctacttt tgtatttta gtaaagacgg       108420 ggttttgcca tatttgccag gctggtcttg agctcctgac ctcagggtga tccgcccgcc    108480
ttggcatcct aaagtgctag gattataagc gtgagtcatc gtgcccaact tggttgttta    108540
ttttcaaata gcctgaattc aagctcacta atgttttctg ctgcttgata catttctgct    108600
attgagagac tgatgcattt tcagtttgt caattgaatt tttccacttt gggattctg       108660 cttgattctt tttactaata attattgcag tctctttttt aaatttatag gattctgaat      108720
ttgttctctg tattatcttg gatttcgttg aactttctca aagcattcag cttgaattct     108780
gtctgaaagt tcacatatct cttatcactt gggaattggt cactggtgtc ctttattttt     108840
agttcatttg gtgaggtcat gttttctcag atggccttga tgcttgtgga tgttcatcag   108900
tgtctgggca ttgaagagtt gggtattctg ttctttgtag tctggttttg tttgtacgca   108960
ttcttttttt ttttttctg tttttgagac agagtctcgc tctgtcgccc aggctggagt     109020
gcagtggcac agtctttgct caccgcaacc tccgtctccc ggattcaagc aattctcctg   109080
cctcagcctc ctgagtagct gggattacag gtgcgtgcca ccacgcctgg ctaattttg     109140 tattttagt aaatatggtg tttcaccatg ttggtcaggc tggtctcgaa ctcctaacct      109200
cgtgatctgt ccgccttggc ctctcagagt gttgggatta caggcgttag ccactgcatc   109260
cggctcccat tcttcttgag aaggttttc aagtattcaa agggaattaa gtgttgtcat      109320
ctaagtcttc gctcactgca gccatacatg cattagaggg caccccaaga ctagtaatgt   109380
tgtgactctg tagaggtatc accttggtag tcttggggaa gatctgggag aattccctgt   109440
attaccaggc agtctcttgt cctcttacat ttctccaaac aaatggagtc tctctttgtg     109500
ctgagctgct tggagtttgg ggaagggtga cacaagcact gccatggcca ccgtcactgg   109560
aactgtactt ggtctcaccc aaggcctgtg gcagctattt tctggccacc actgatgtta    109620
atttaaggcc caagggtgct ttagtcagta ggtgaagaat cctgcaagaa ctgggtcttt    109680
actttcagtg cagcaggttc ccttctggcc cagggtgtgt ctagaaatgc tgcccaggag   109740
ccagggcctg ggatcgggag ctttaggaat ctgctttatt gtactggggc tgagctggca   109800
cccacttgca agataaagtc cttttactc ttctctcacc tcaagcaggt gggtctcccc       109860
atggacacca cagctgtgaa tgtgcgggt catatctgaa gctggcacaa tacgacatgg     109920
caccttgttt tttattcaag gcacaagggc tctttagtca gctggtggtg aatcctacta     109980
ggactaggta tttcccttca aggcaatggg ttccttctg gtccagaata tgtctagaaa     110040
tgtcatctgg gagctatggc ctagaattga ggcttcagaa ctatgcttgg tgctttattt      110100
tactgtggct gaactagtat ccacattgca agacaaagtc ctccctactc ttccctctcc     110160
tcccagagct gtgagctgtg gtacctggag ttggggaaag gctggcacaa gcactccctt   110220
```

```
ggccaccta gctggtgtct cagtgggtca catgtacccc aagtccactg actatgagcc   110280
cagcacagta ccatgacttg tccaggaatt gcagtccttc tggtctagac tgcctttcaa   110340
gtttatttag gaccccagag gactttaccc acggtggtgg ggcttaccaa aattaagatt   110400
cttttggttt tttttggcag agtttcgctc ttattgccca ggctgagta tagtgacgca    110460
atctcagctc accacaacct ccgcctcccg ggttcaaata attctcctac ctcagcctcc   110520
tgagtagctg ggattaccgg catgcgctac cacctctggc taattttttt gttttttagt   110580
agagatgagg tttctccatg ttggtcaggc tggtcttgaa ctcccgacct caggttatcc   110640
gtccgcctcg gcctcccaaa gtgctgggat tacagaccat agtgcccagc ccgaaattca   110700
gattctaatc actgggatgg acaattcccc tctgactagg gctagtctaa atactccctc   110760
tgtgggtgct ggctgaattc tgtcctatgc tgctttccac tgtgacaggg cagcactgag   110820
tttcaatgca aaatcccaca gtcatttctc tctctctccc ccgagcacac agattctttc   110880
tccaccccac actgcattgt gggggaatgt caggggtgtt ggaggggcag ttcaagacta   110940
tcttccttat ctttttttggt gtcttttttcc ttgataggat gtcaaaactg ggtactgtga   111000
tcgcttacct aattttttggt tcttatgaag gtgctttctt gtgtggatag ttgttcaatt   111060
tggtgctcct tgttggggat gatcactgga aggttctgtt tggccaccat gctctgtctc   111120
ttctccccctg ccatctcctt tttttactta ggggtttaga atgtctaact gaccaatatg   111180
tacagtcagg tctcattctg aattcaccta cttaatgacc ttccaagctg actaggccca   111240
gcgcttagtc cagcctccat gacggtccct ccacatccta attagcctcc ctccagttca   111300
tttcacacaa agctgctgtg ttcacctttc tgaactataa atctgcccag tactctaccc   111360
tacttaaaat tccgtataga ctgcccattt gccctgagaa ttaaaagcca aagtcctaaa   111420
cgtagctttt taaaactttt tttttttttt ttttaatttt tagatggagt cttgctctgt   111480
cacccaggct ggagtgcagt ggtgtgatct tggctcactg caacctccgc ctcctgggtt   111540
caagcaattc tcatatgtca gcctcccaag tagctgggat ttacacgtgt gccatcacgc   111600
ctggctaatt ttttttttttt atctttagta gagacggagt ttcaccatgt tggccagtct   111660
ggtcttaaac tcctgacctc aagtgatcca cctgccttgg cttcccaaag tgctaggatg   111720
ataggtgtta gccactgcac gcagccctga acatagcttt taagttcctt tattgtcata   111780
ttccttttga cgagtctatc atttttctgac tcacttgtac atgtgtgtct cacccttggt   111840
ccagccattg gtgcttttct ttacttcttt attttttgtta tttttatttta ttttattatt   111900
attttttaaa tgagacaggg tatcactatg ttgcccaggc tggtcttgaa ctcctgagct   111960
taagcagtct gcttgtctca gcctcccaaa gggctggaat tacagtgatg agctactgtg   112020
cccagctcat tggtgctatc ttttttttttt tttttgagac ggagtctcgc tctgtcaccc   112080
aggctggagt gcagtggcgt gatcttggct cactgcagct ccacttccca ggttcacacc   112140
attctcctac ctcagcctcc cgagtagcag ggactatagg cgcctgccac catgcctggc   112200
taattttttgt atttttagta gagatggggt ttcagcgtgt gagccaagat ggtctcgatc   112260
tcctgacctc gtgatccgcc tgccttggcc tcccaaagtg ctgggattac aggcgtgagc   112320
caccgtgccc ggcccccatt ggtgctattg ttttatgtga tagagccagc ttctcccttt   112380
tctttggatt tttaaacata ctcttccttt tacttagact attctccatc ccaacaccct   112440
tcctaaactt ctttcacacc ttagactagc tgacactttta ctgagaaacc tttcttttt   112500
ataggttgct ttttctatag actctcttag catttactca ttttattgtg aagtgtctga   112560
tcttatttaa atgacaagta taagaggata gaaactattt catattttttc tcacccagca   112620
```

```
ggcacaattt ctgacatgtg gtaagcactc agtaaatatt gaactttaga ggctaggaca   112680
tttgagtgct ttggtgactg tggttgtgct atataggtac tctgttattg ttagtttata   112740
gtaaaagcat tactcttaaa gtatgaaaaa agccttattc agaacatttc atgcgtatag   112800
ttaatattac gtagcttgtg ctcatggcaa aaatgtatta ctaaagttat ttaagatatt   112860
taagtataat tgtttccttt atttagttac agccaagttc tacttctgaa tctatggatc   112920
aactactaaa caaaaataga gagggagaaa atcaagaga tttgatcaaa gacaaaattg   112980
aaccaagtgc taaggattct ttcattgaaa atagcagcag caactgtacc agtggcagca   113040
gcaagccgaa tagccccagc atttcccctt caatacttag taacacggag cacaagaggg   113100
gacctgaggt cacttcccaa ggggttcaga cttccagccc agcatgtaaa caagagaaag   113160
acgataagga agagaagaaa gacgcagctg agtgagtaaa cctggaactt agaccatcct   113220
gttactcaat taacttttt tttttttaaag gcatttaggt ccttccaact gtgaagaatc   113280
catctggact tttagactac tttatacatt gcccttagtt tacaaacagc tagtccaaac   113340
aaatgacatc ttaagtaaat gaggttattg caccctgtgc tactcttctg ttcttcccct   113400
tttttgtacc ccagggctag aaaaacaagg cataaattaa gaaagttttt tctgtaaatg   113460
aacaggagtt gaaaaattat caattcaggg gacctatctt tactggattc cactcattag   113520
tcaccctcac tgtgctgcta ggttgaaaaa ctgccactgt caaggagaga agcatgcggt   113580
gcttctactt ggaattcaaa atattttca tcagaaactg tgttttagtt aatgtttaga   113640
tttgttaaga tagacttaat tctgcacatt cagtatatta attaaatgga cttttagggg   113700
ctaacctcag aacttaacta ccattgactt aggtgtttgg gtaccaaaca atccagttaa   113760
agctgaagtt ttggaatgca gcttattgat aaattgggga ctgcttattc ttgatttgag   113820
gcaatttttt tttacagcca tgacttttc caggtatgtc atgtaaaata tcttctcaca   113880
taagaattac tgcatgctag aatattggta tgttgactgg tagctcatac ctataatccc   113940
agcactctgg gaggtccaag caggtagatt acttgaggtt aggagttgaa gaccagcctg   114000
gccaacatgt gaaaccctgt ctgtactaaa aatacaaaaa ttagccaggc atggtggtag   114060
gtgcctgtat cccagctact cgggaggctg aggcaggaga attgcttgaa cccagaaggt   114120
ggaggctgca gtgagccgag atcatgccac tgcactccag cctgggtgac agagcgagac   114180
tctgtctcaa aaataaataa ataaataaat aaaaggatac tgttatgtta agaattgctt   114240
ttaaggatat ttcataagta gctactgtct tttcagctca agtgtttgtt gattggccag   114300
gcgtggtagc tcatacctgt aatcccagca ctttgggagg ctgagtcagg cagatcactt   114360
aaggtcagcg tggccaaaat ggtgaaaccc catctttact aaaaataaat attaaaaaaa   114420
attagctggg cgtggtggca gtctcctgta atcccagcta atcaggaggc taaggcaaga   114480
gaatggctta aactcgggag gcagaggttg cagtgagcca agattgcact gctgcactcc   114540
aacctgagca acagagtggg actctgtgaa ggaaaaaaaa aaagtatttt ttgattgcct   114600
ttgagaggaa cggttgtata ttactcagat ttttaaaaaa ttgttctttt atggctgtat   114660
tctttaaggg attaaggaat gggcaatata agtgtatatg tttcaataaa aacgattagt   114720
gatcttctag tgagaacagt ttaaatctat atttagcaat ttttttttaaa ttgtcaggta   114780 tggaagattt tagagcaacg taaagtccat gtagatttca ctggccttta tatttttttt   114840
aggcaagtta ggaaatcaac attgaatccc aatgcaaagg agttcaaccc acgttccttc   114900
tctcaggtag gtttattact ttctttgagg ttatctagtc ccaaaaaaag aaaaattatt   114960
```

```
agtaatagtc cttcttccat acctgccatc tgaattttgt tttagtgtgc tgaaccaacc   115020
ttctttcttt tttttacatg gccattaatg aatacttttt aaacattaaa aaaaggtctt   115080
tgttttgtca tcaattagat gtgatcttgg gcaaatcttt gaatttctct gacccagaat   115140
ttgacgatgg ttggctagct aggctgtcag gtttatagat acgtcctctg cacctgaggg   115200
ttttgcatca ctggattcaa ccaaccatgg atcaaaaaca tagttaggat aatctatact   115260
gaacacatgc agacgtttcc ttgtcattat tccaaaacaa tacagtaaag catttacctt   115320
gttttaggta ttataaataa tctagagatg atgtaaagta tataggagga tatgcatagg   115380
ttgtatgcga atactacatg attttatgta agggacttga gcattccaag actttggtat   115440
cttcacaggg tactgtaacc aatccccccac agatactaag agatgactgt actattgtta   115500
ttattcgact gagatcataa gaagatatat ttattttttaa tttttaaaaa cacttccatc   115560
agtttcttaa aaatagctgc cactgttttt aatattttt aattgacaaa gttttaagtt   115620
cctactgaaa catttttttct tttattgaaa tgtgaaaatt tatgtgctgt gttttttgttt   115680 tcaataaaag ggacatagtt aaagcaagta aaattagaaa gactgggaaa atccgtcttt   115740
aaattgcaat aatagttcat ctgttacctt gagataattg aatttattgt tgttttttgta   115800 gccaaagcct tctactaccc caacttcacc tcggcctcaa gcacaaccta gcccatctat   115860
ggtgggtcat caacagccaa ctccagttta tactcagcct gtttgttttg caccaaatat   115920
gatgtatcca gtcccagtga gcccaggcgt gcaagtaagt catagaattt gatgttcact   115980
tagcctcccc aattgtttgt atctgacacc aagcactctt taggttttca gtgacttgag   116040
ggtgtgatgg ttatgcatat gcatttgaaa cagacaggca tgcagagatt cagtgtgttg   116100
ttaagtatga ggacctaaat ctgagaatgt tttctgtgaa aaagatggtt tagatttact   116160
gtagtttggg gtttgttcct tttagctgtg ggtatgatct aattttttaa tgactaatgg   116220
agaatcagga aaccttctca tgcctagctc tctagcaata taaaactaag agtgacagaa   116280
taccttgtta ttatcatagg tgcctaatgt taattttttt tttaattctc tcaagccttt   116340
atacccaata cctatgacgc ccatgccagt gaatcaagcc aagacatata gagcaggtaa   116400
aggtgagaat aatcctgcct gtgtttgctt gtagtttgca tgctgcatga attgagtaac   116460
taagtttata atgaataaat agttgtagtt tagctctgac ttttttgatga ggctatgcat   116520 tggcttttga tgaacaacat tacatagata ttcacatgga ttttatgaag aaaaacaggg   116580
gagaaaaaat gcccatcagt tgtgattata tagtatcctc ttcaaaaaga gtaattggag   116640
gcctggtgtg atggctcaca cctgtaattt tagcactttg ggaggccaag gcaggaggat   116700
tgcttgagct caggagccca agatcagcct ggacaacaga gactttgtct ctactaaaat   116760
tcaaaaaaat tagctgggca tggtggcata tgcctgtagc cccagctgtt tgggggactg   116820
aggcgagagg atcacttgag cccaggaagt agaggctgca gtgagctgtg attatgccac   116880
tgccctccag cctgggcgac agagtgagac cccgtctcaa acataaatac tggctgggca   116940
tggtggctta tgcctgtaat cccagcactt gggaggccg aggtgggtgt atcacctgag   117000
gtcagtagtt tgagaccagc ctggccaaca tggcgaaacc ccatctctac taaaatacaa   117060
aaattagccg gacatggtgg cacctgccgc ctgtaatccc agctactagg tggggctgag   117120
gcaggagaat tgcttgaacc cgggaggcag gggttgcagt gagccaagat cgtgccactg   117180
cacttcagcc tgggcaacag agtgagactc catctcaaaa caaacaaaca aacaaaaaac   117240
aaacaaacaa aaaaccagat ctaattggct ggacacagtg gctccatgcc tgatatccca   117300
gctggaggat gacttgaacc catgagttcg agagcagcat gggcaatata gtgagaccct   117360
```

```
atctcaaaaa aaaaaaaaaa agttaattcc aaagcttttt gatctgaaat ctgatttaaa   117420
tctgaactta aatttgaaga agagggtttg ctagattaat ttactagatt gctaaccttg   117480
ctttatatat acctacagtt atttccccaa agccagaatt tcttttgaag cagaggggca   117540
actaacttca accaatgtta agatcctatt agaaggatgt ttcggctagg cttggtggct   117600
cacgtgtaat tccagcactt tgagaggctg aggtgggcag atcacatgac cgggagtttt   117660
aagaccagcc tgggcaacat ggcaaaaacc tatctctgca aaaaaaaat agaaatctta    117720
gccagccgtc atggtgtgct cctgtagtcc tagctacttg ggagactgag gtgggaggat   117780
caattgaaac cagaaggtcc aggctgcagg gaactgtgac tgcaccactg gctccagct    117840
tgggtgaaag agcgaaaccc tgcctcaaaa agaaaaataa gatggatgtt tctgcattaa   117900
aattagggag ttgtcgtata atgtagttgc ataaactagt attctgtgct tgtgtggtta   117960
aagagccttc gtagaaaaaa tcccacattt ttcttaaaag gaaatctttt ggccaggtgt   118020
ggtggctcac atctgtaagc ccaacactct gggaagccga ggtgggcaga tcacttgagg   118080
tcaggagtac aaaaccatcc tggccaacat ggtgaaaacc cgtctctact aaaaatacaa   118140
agatcagctg ggcatggtgg tgcgtgcctg ggtgacagag cgagactccg tccaaaaaaa   118200
aaaaaaaaaa aaaagagttc ttttaatgtt ggaaaatgct aaagggtttt tttttgcca    118260
accagttaat ttagagtgat taactgctat cagttgagaa actatagaaa gtagaataat   118320
ttatacagaa aagacatttc tcagtgccca ataattgcct ttctgacata aagttttcat   118380
ttttcctgaa ttaataagat ttcctcaatg tgttttttg ggtgttttgt gtgtgtgtgt    118440
gtgtgtgtgt gtgtgtgtgt gtgtgtgtgt gtatgtgttt gatacagggt cttgctttgc   118500
tgctgaggct ggaacgcagt ggcgctatca tggctcaatg cagccttgac ctcctgggct   118560
caagcgatcc tcccttctca gtcccctgga tagcggggc tacaggtgca caccaccaca    118620
cctagctaat ttttgtattt tttgtagaga tgggtttttgc catgttgcct aggctggtct   118680
caaactcctg ggctcaagcg atctgcctgg ctctgcttcc caaagtgcct gcgcccagcc   118740
aattttctcc atgtttgacc taattgtgat ttcatagatg ttaactaaaa ctcttaattt   118800
tcgttttctc agtatgctat tttttttttt tttagccttg gaacatatga acctgttgaa   118860
agaactctgc ctgaaataat gtaatcaaat tatagagttt aatcttattt tgagggcctt   118920
tagaaattct gagaagaaag tgggtttttt tttttactgc cattttaatg tagtgttaag   118980
gtgttcatgt atcaccagca ggtgtagctg ttttcaatga ttacttaaaa caatgcaatg   119040
ggaacttttt gttgtcatta aaatataaaa ggttactgta gtaagagcaa gcatgacagt   119100
ttggctatct gatgggagag tcacattcta acttcaggag gtactgtctt tttaatagaa   119160
atgatatact cagagtctgg gcacggtggc tcacgcctgt aatcccagcac tttgggaggc   119220
cgaggtgggc agatcacgag gtcaggagat caagaccatc ctggctaata cagtgaaacc   119280
gtgtctctac taaaaataca aacaattagc tgagcgtggt ggcaggtgcc tatagtccca   119340
gctactcggg aggctgaggc aggagaatgg catgaacctg ggaggcagag ctggcagtga   119400
gctgagatgg tgccactgca ctccagcctg ggtgacagag cgagactccg tctcaaaaaa   119460
aaaaaaaaaa aaaaaatagt agagaaaggg cttgccatg ttggccgggc tggtcttgaa    119520
ctcctggcct caagtgatcc acctccctcg gcctcccaaa gtgctgggat tacaggtgtg   119580
agccactgct cctggcctga atataccact tttacctatc atcagttgat gaacatttgg   119640
attatttcct ttttctggca atgagtaatg cttttgtgga ttttcatgta caaattttca   119700
```

```
tatgaggctg ggagcagtgg ctcatgccta taatcccagc agtctgggag gctgaggtgg 119760
gcagatgact tgaggtcagg agtttgagac cagcctggcc aacatggtga aatcccatct 119820
ctactaaaaa tacaaaaatt acactggcat ggtagcgtgc acctataatc ccagctattc 119880
aggaggctga ggcaggagca tcagaatcgc ttgaacctgg gaggcggagg ctgcagtgag 119940
ctgagatcac accactgcac cccagcctga gtgaaagagt gagtctcaaa aataaaaaa 120000 taaaatttt tttcatgtgg ccttagattt tcatttctcc taaagtagaa atgctgtgat 120060
ggaactgcca aacttttcca aagcagctgc atcattttgt atttctacca gtaatgtaca 120120
agtgttccag tttctccaca tcctcataaa taaccgatat gtctttggtt tgggttatgt 120180
ccattctagt ggttatgaag tgtcattgtg gttttttgtt tttttgtatt gttttgagat 120240
cgtgcccagg ctggagcaca gtggcacaat ctcggctcac tgcagccttc gcttcctggg 120300
ttcaagcaat tctcctgcct caccctccca gatagctggg gctgcaggca tacgccacca 120360
caccaggcta attttatat ttttttgtaga gatggagctt ctccgtgctt cccaggctgg 120420
tctcgaattc ctgagctcaa gcgatccccc tgcgtcagcc tccagagtag ctgggggttat 120480 aggcgtgcac caccgcgctc ggcccatttt tgtatttta gtagagatgg aatttcacca 120540
tgttggccag gctggtcttg aactcctgac ctcaaatgat ccgcctgcct caccttccca 120600
aagtgctgag attttagacg cgaaccacca tgccctgact ataggttatc ttttacttg 120660 cttgatggtg ttctttgtaa cacagttttt aattttgatg aagttcaatt tatctgtttg 120720 tttttctt tgttgctgtt gctcctgatg tcatatcaga caaagcattg cctaactcaa 120780
ggccacagag atttactcct atgaaacgcc tataaaactc ctatgatttt tatagtttag 120840
ctcttaacat ttaagtctac aatctctttt gagttaattt ttgtgtatga gatgagagta 120900
gtggtccagg ttttttcctt tgcttgtgga tatccgttgt ccccacctca tttgttgaaa 120960
agactattct ttcctcttaa attgtttgtt tgtttattta ttttgagat ggagtgtcgc 121020 tctgatggag tggcgctaac ttagcttcac tgcaacctcc gcctctcaga ttcaagcgat 121080
tcccctgcct cagcctcctg agtagctgga attacagggg tgcgccacca cacccagcta 121140 attttgtat ttttagtaga cgggggttt taccgtgttg gtcaggctgg tctcgaactc 121200
ctgatctcgt gatctgcctg tctcctggca ccctgggagg ctgagaggct gaggtgggag 121260
gatcacttga gctcaggagt ttgagaccag cctgtaccat tatgcctggc taattttaga 121320 attatctta aagtataaaa tgtgaatcca atttatcttg ttctaaatga ctatccaaaa 121380
tgttttaacc agttttatta gtctgtaatt tacatacaag aaaatgctca tcttttatg 121440 tttacattt aatgagtttt gacaaatata tttgctcatg taactacttg cttcatcagt 121500
gaagatggaa aacattgtgc ctgttcctct tctctgtcca actgtacttt attaccacta 121560
gctccagtta accagtaatc tgccttcttt tactatagat tagatttatc ctctttagat 121620
ttctttttct tttttttttt ttgattaggt ttttttttt ctttttttac gtaaaaaat 121680 ctttttttgg agacgtctca ttatattgcc caggttggtc tcgaactctt gagctcacct 121740
cagcctccca gagtgctagg attacagatg tgagccacct cagccagccc ctagattttt 121800 ttttttttt taataaatgg aatcaaacag cgtgtaacag aggtgttcaa tcttttggct 121860
tccctgggtc atattggaag aagaattgtg ttgggccaca cataaaatac agtaacacta 121920
atgatagctg atgaacaaaa caaaaaaaaa tagcaaaact tataatgttt taagaaagtt 121980
tatgaatttg tgttgggcca cattcaaagc cgtcccagga cgcaagttgg acaagcttgg 122040
tatataattt catatgtgtg tcctaaacag tgtagtaatt tgaatttcat gttagtatca 122100
```

```
gcttattcct ttttgtttgt ttgtttgttt ttgagatgga gtcttgttct gtgtcccaga    122160
attggtctgc aattccactg cctcagcctc ccaagtagct gggattacag gcacgtgcca    122220
ccacacctgg ctaattttg tctctctctc tttttttttt tttttttttt tttttttagca    122280 gagacgggat ttcaccatgt tggccaggct ggtctcaaac tcctgacccc aaatgatcca    122340
cctgccttgg cctcccaaag tgctgggatt acaggtgtga gtcaccgtgc ccagccagct    122400 tattccttt tattgctggg tagcatttca ttttatgatt ataccacagt taatttaccc    122460
attactagtc gatgggcatt tgagttattg ccagcttttg gctattatga atgaagctgc    122520
tgtgagcatt tgtgtacaag tgtttgtgtt tttatttctt ttagttaaat acctagaatt    122580
ggaattgctg aggtatggta agtgcatatt tcatttttt aaaaaattta ttttattttt    122640
tatttattta ttttttttga gatgaagtct cactctgttg cccaggctgg agttcagtgg    122700
cgtgatttca gctcatggca acctccctgt cccgggttca agcaattctc ccgcctcagc    122760
ctcccaagta gctgggatta caggcgcgca ccaccatgcc tggctaattt ttttgtattt    122820
ttagtagaga cggggttca ccacgttggc caggctggtc tcgaactcct gaccacaagt    122880
gatccacccg ccccagcctc ccaaagtgtt gggattacag atgtgagcca ccacacactg    122940
cctggtaaat acatatttca attaataaga aactagcaat cttctaaagt gattgtgtca    123000
ttttacattc caactgatca ggtacatgtg taggttccat gtgttctgca tccttgccaa    123060
cacttggtat tgtgttatct ttttaatttc aacaggtcta atgggtgtct tatggtatct    123120
cattgtgatc ttaaatgtac atttctctga tgatgactga tccaggagca cctcatcatg    123180 tgtgtgttg ttttcagctg tcaacctttt tttagtaaat ggttcaaatc ttttttccat    123240
tttatttatt tatttattta tttgatggaa tctcactcta ttgcccaggc tggaacgcag    123300
tggtgccatc ttggctcact gcaacctccg cctcccaggt tcaagcaatt cttacgcctt    123360
agcctcccaa gtagctggga ttacaggcat gcgccaccat gcctggctaa ttttgtattt    123420
ttagtgtagg tggggttca ccatgttggt catgctggtc tctaactcct gacctcaggt    123480
gatctacctg cctcggcctc ccaaagtgct gagattacag gtgtgagcca ctgcgcctgt    123540
cctaataatt tcttttgtc tcaatgtttc tgcctgggtg cactggctca cgcctgtaat    123600
tccagcactt tgggaggcca acctggatgg atcatttgag ccaacagttt gagaccagcc    123660
tgaggaacat gacaaaaccc tgtctttgca aaaaaaaaa agaaaaagaa aaattagcc    123720 aggcacagaa gcgcattcct atggtcccag ctacttgggg ggctgaggtg ggacaatcgc    123780
ttgagcgagg ttgcggggt ttggagggcg atggaggggt gatcgaggtt gcagtgagct    123840
gagattgcac tactgcactc cagcctgggc aatagagcca gaccctgtct cacaaaaaaa    123900
agaaaaaaaa gtcatgtttc ttttcttact gtgaaaataa agttactact tttagtaaat    123960
tattttaagt tatttatata ttctggttac aagtcctttc tcagaatatt gtgaatattt    124020
tctcccagtc tgcggttttt tttgaagagc cagtattgtt aattttaatg aagccttatt    124080
tatcaagctt ttctcttaag gttcatgctt ttttgtatca taataagaaa tcttttacgt    124140
accctaggtt atgaatgttt ttatggttag gtatatggtt gatttcaggt taggttttgt    124200
gtagggtgtg atgtaaaggt ctagcttcat tttctccacc ataaatattt actcggttc    124260 tctggcacca gcctctgttt tccattggtg gctttatttt ttttctgttc ttgaaacaag    124320
agtctcgatc ttgttaccca ggctggagtg cagtagtgtg accttggctc actgcaacct    124380
ccacttccca gggtcaagcg attctgcctc agcctctcga gtagctagga ttacaggtgc    124440
```

```
ccgccactac acccagctaa tttgtattt  tttttttttt tttttagta gagacagggt 124500
ctcaccatgt tggccaggct agtctcgaac tcctgacctc aggtgatctg ctcatctcag 124560
cctcccaaag ttctgggatt acaggcatga gccactgcgc ccagccatag tagctttatt 124620
gaattcagtt gactgtattg tatgtgtgtc tatttgtgaa ctgttttgtt gtattgatct 124680
ttgtatatat ccttatgcca attctctctt tattgctgtt actttgtaac caacctttaa 124740
gttcatatga gtctcccagt tttattctcg tcaaaattac tcttattctg cgttctttga 124800
atttgcaaat aaattttaga atcagcttgg gattgtgcac tgaatcttta tatcagttct 124860
gggagaaata tcttaacaat atggaatctt cattgaggtc atcatatact gctccattta 124920
tttaagtctt aagtttcacc agtgttttct agttttcttt gtatcagttt tgtgcctgct 124980
ttcttaaatt tatcccttaa tatttcatct gttttgtgct gttgtgagtt atatttaaa 125040
aactttcaac gtttgtttat tcgtaaatag agatgcactt gattttgaa tattgacctt 125100
gtgtcttgat gtgttggtaa acccactgtt tctggcagcc ctttaagact taaacataca 125160
atcatgatct aatcaccatg ttggtgtttt tgggttttt  tttttgtct tattgtactg 125220
gtgcattact gaaaaggca tgagattttg ccatgctccc attttaggg gtgagacatt 125280
gtctttcact attaagcata cagttaggtg ttacttcagt tcctaatttg cagaggtggg 125340
tttgttttct ttttaatcat gaatggttgt tggattatgt tcaaatactt atcatctact 125400
aagtatatca tattgaccag gaacagtggc tcatacctgt aacctcagag ctttgggagg 125460
ccaaggcagg aggatcgctt gaggccagga gttcaagacc aacctgggtg atgtaggaaa 125520
accccatatc tacaaaacaa tttaaaaatt tgctgggtgt ggtggcacac acctgtagtc 125580
ctaactactt gagaggctga ggaaggagaa ttgcttgagc ccagtagttt aaagcagcag 125640
tgagctgtga ttgtaccact gtactccagc ctgggtgaca aaggagacc ctgtatttaa 125700
agtgtgtgtg tatgcgtgcg catagatgga tagataataa tgtaattcca ttatggtcat 125760
acaaactgat atgaaatgcc attttatcat ataacaagtg tcttttttgtg gttgaatttg 125820
tttctggatt tttcactctg cttcactaat ctaataggac taccttctca tccactcact 125880
gccaacattg attttttttt tcagattacc ttgaattttc tgtttatttt tccatatgaa 125940
ctctataatt aacttactac taaaaaaatc agttgccttt ttaaaaccaa ctgatcttta 126000
aaatatatct tggctgggcc cggtggcagg cacctgtaat tctagctact gggagactg  126060
aggcagaaga attgcttgaa cccaggaggc ggaagttgta gttgagttga gattgcgcac 126120
ctgtactcca gcctgggtga cagagcaaga ttccctctta aaaaaaaaa aaaaaaaag  126180
aaacagaaaa gataaatctt tttacaataa tttgttccaa ttagggtcca agtcaggctt 126240
gcaatttgga tttgtttata tgttgaagtc ttttttttt  tttaattgtt tcatattgtg 126300
gtaactttt  tttttttttt ttgagatgga atcttggctc tgtcacctag ctggagtac  126360
agtggcacaa tctcaactca ctgcaacctc ccctctggg gttcaagcaa ttctcctgcc 126420
tcagcctccc aagtagccca gcctttttt  tttgagacag agtctcgctc tgttgcccag 126480
gctggagtgc agtgatgcga tctcggctca ctgcaagctc cgcctcttgg gttcatgcca 126540
ttctcctgcc tcagcctcct gagtagctgg gactacattc gcccgccacc acccggct  126600
aatttttttg tatttttagt agagacaggg tttcaccgtg ttagccagga tggtatcgat 126660
ctcctgacct cgtgatccgc ccgcctcggc ctcccaaagt gctgggatta caggtgtgag 126720
ccactgcgcc cggccttgta ttttaatag agatgggggtt tcaccatgtt ggccagcccg 126780
gtcttgaact cctgacctca aatgatccac ccgcctcggc ctcccaaagt gctgggatta 126840
```

```
caggtgtgag ccatcgctct cagccttgcg gtaactttt  attacgaatg tattgagaca  126900
ttaataacct aggccagtca tgtttcatcc ctacccattg tctcttaaaa gctttgagtc  126960
cactggatta ttctgaagca aattctagac attgcatcag tttatccacc aacattttag  127020
tgtgtatctt taagttggtt ttggttttgt ttttgtttt  tgagatgggg tctggctttg  127080
ttgcccaggc ttggagtgca gtagtgcaat catagctcac tgctgctgcg aattcctggt  127140
ctcaaaggat cctccctcct cagcctctca agtaactgtg actacaggca catgccacct  127200
tgccagcttt tcttttcttg tcttgtcttt cttcttcttt gttttttttgt ttgttttttg  127260
ttttttttg  agacagagtc tcaccatctt tctatcttgc ccaggctagt cctaaattcc  127320
agggcttaag ttatctttct acctcagcct cctaaagtgc taggattaca ggccagcact  127380
ttaggaggtg ctggatgagc catcacaccc agccaagtca taggttttt  tgtttgtttg  127440
ttttttgaga cagtgtctaa ctctgtcacc caagctggag tgcagtggca tgatttcagc  127500
tcagtgcagt ctctaccaat tgggcttagg tggtcctccc acctcaacct cccaagtagc  127560
tgggactaaa ggtgcgcgcc accatacctg gctaattttt gtattttttg tagagacagg  127620
gttcgaatt  cctgagctca gcagtctgc  ctgccttgac tcccaaggtg ccaggattac  127680
aggcatgagc cactgcactc agccctcaca gttttaatta cagttttcc  cttagttttt  127740
gtcttgttca tatccagctt gtcttgtatt ttttcccac  gatctgaatt ttgctgactg  127800
tatccctgtg ttgatattta agtagactt  ctgtccctg  taatctttgt aaactgatag  127860
taaataatga aggcttgatc agattgggtt tttttttttt ttccccaatg tttcacagat  127920
gtgtgtactt tcagtgagga gtcatgtaat cagtcttttt cctgatagga gtagtcagtg  127980
agttcctaga tgttttatct atccaggaga taatatgtcc ctttagcgcc ttaattttt   128040
tggtgtgttt tttagcagcc attgatgata attgtctagc ccaagatcag ttatttcctt  128100
aggggttgta aaatggtgac attctttttcc tttcatccct tcttcaatta ttgcctggaa  128160
tatttctata aagaaaaact ttcccatatc cagctgtttg gttaccctga ggtatagctt  128220
tcttaggaaa agtaatttaa aatgttaatc atttcccttt ttaaggcagt cttcaaaata  128280
atgagttggt ttctgttat  cctccaaagg taaccagtga ggtggttttt ttgtcgttgg  128340
ttcttactat cagtataaac ttctggaatt tttttttttt ttttaatttt ttggagacaa  128400
ggtctggctc tgttacctag gctggagtgc agtgggatga tctgggcata ctgcagcctc  128460
aacttcccga gctaaggcaa tcccccacc  tcagcctccc aagtagctgg gactacaggc  128520
aagcaccacc gtgcctggct taattttgt  atattttgca gagacagggt ttcaccatgt  128580
tgcccaggct ggtgtcgaac tcctgagctc aagcagtctg cctgtgtcag cctcacaaag  128640
tggtgggact acaggcatga gccaccatgg caggccagaa tcacaataaa cttataaatt  128700
aacttgagaa gaaatgattg atgtcttcat gatgttgagt cttcctgttc aagaacaaag  128760
tataccttca atagcatatt aaagtttatc cttggctgga tgcagtggct gacgcctgta  128820
atcccacctc tttgggaggc agaggtgggc agatcacctg aggtctggag ttcgagacca  128880
gcctggccaa catggtgaaa ccccgtctct actaaaaata ttttaaaaaa agtattagct  128940
gggtgtggtg tgcacctgta gtcccagcta ctctggaggc tgaggtagga gaatcgcttg  129000
aacccaggag gcagagagtg cagtgagtca agattgcacc actgcactcc agcttgggca  129060
accgagcgac actctgtctc aaagaaaata aataaataaa aataaagttt atctttaagg  129120
ttttgtacat ttttttcagt gtatgcctta ggtaggttct tttttaatgt tagtgtaacc  129180
```

```
cagggacttc tcttccattg catcttctaa gtaattactt atgaagtacc atatatgaag 129240
gctattgctg tttatatgtt agtttttacc ctgctccttt actaaattcc aatcctttga 129300
ggtattggat aaaaatattt ttagcatttt tcaaataaca ggcagagtca agggcttggt 129360
ttcttttctt cccctcctgt cccctaccct cccctttttt gagacagggt ctcacttctt 129420
cgccgaggct ggagtgcagt ggtgcagtta cggcttaccg cggcatctgc ctccctggct 129480
gaaaagttcc tcccacctca gcctcctgag tagctgggac catagatgca cagcaccgca 129540
gctggctaat atttttgtat ttttttgtgga ggcagtgtct ccccatgttg cccagggtgg 129600
tcccaaactc atgagctcaa gcagtccgct cgccctggcc tcctaaagtg tagggattat 129660
aagcgtgagc cactgcgcct ggcctgggga tcatgtttta acatgagaat tagtggagac 129720
aaacacatga tatctaaata atagcaccat agtatacttg actagctttt taattatttt 129780
ttaaatatac aggaaggtaa taagtaacaa agtaataata gtgaatagtt taagctcagt 129840
tagcataatc gggcaaactt tcatttgata aaagtgataa gtagttttca gtggcttttt 129900
tgtttaccag aaggaggtgg ttttttaaata cgtgcatcca agataaaata taaaaaaatg 129960
ttcaggtttg ctttcctaca tagataaaat aatatgtaac tagctctccc aaatttcagc 130020
aacagttagt gaatgtttag ccacaaattt gcagttaatt atataatcag ttcttaggat 130080
tttatgaaca agttctatat tctttgtgcc ttatacctag ttgtaagcag tcattccaca 130140
attatttttcc tgaagtggct tggttaatgc cacaccagaa acaggtcaca gacaatagtg 130200
ctgtaagaaa tgtgtgagga aagaggcaca tgggaagtag ctagctcgtg ctggaggaac 130260
tggaaaaaaa cctcacatgg gagatgacag ttgagctgaa ttcttaacta gagttgtaac 130320
agggcgaggc ccttacatgc agaccacctg tgtggattaa gataagacat aaagtaatct 130380
tttaaaagaa ctattattta gaaacctggt atatgctaca tggtgctgtg ttatactggg 130440
tttgagaaag aatgggaagt gttacaagga ttcagtggtt ggaaattaag gaagatagaa 130500
agttagtgtt ggatctgttt tggctctttg gtcatgcctt tgtttttctc aaaatgaatg 130560
cagtgcccgt cccagaaaat accatatgag aagcgatttc ataatgctgt gagagtctgt 130620
tacagggact tgatcaagtc tgagggccat gagagaaagt ccctctgagg aagttgcttt 130680
caagctgaca cctgaaggat gaagcagaat tatcccagct gggatttggg aactggtgtt 130740
tgaggctgag gactagcatg catgatagga aaataaccca gagtggcaga agtgggagtg 130800
gtatgagatg gcatcagaga cgcagattca gggtcaaatc attcagagcc tcctagacca 130860
tgtgaacaca tgtattatgc tgtggagata ctgtttaata ggcagtctgc ttttttttct 130920
gcagtaccaa atatgcccca acagcggcaa gaccagcatc atcagagtgc catgatgcac 130980
ccagcgtcag cagcgggccc accgattgca gccaccccac cagcttactc cacgcaatat 131040
gttgcctaca gtcctcagca gttcccaaat cagccccttg ttcagcatgt gccacattat 131100
cagtctcagg taaggctggt aaggcctaac tcttaatttt tgtaccatat aaaaaaactt 131160
ttaatatggt aaagggattt tcctttataa ttttttgcttt tgtgtgatgg tagggtagat 131220
agctaaggac ttggggaccc ttttcaatat atattcgaag gttactgatg attgtaagag 131280
gttcagagga aacagccaag aaagatttga gagtttacag ctgtttctgg aaatctgaaa 131340
accatggagt taaaaatctt aactaaagtc tgcttggctc tatttgcagt gttaatgtgc 131400
tttctttatt ttttgtttga acacagcatc ctcatgtcta tagtcctgta atacagggta 131460
atgctagaat gatggcacca ccaacacacg cccagcctgg tttagtatct tcttcagcaa 131520
ctcagtacgg ggctcatgag cagacgcatg cgatgtatgg taggaagcac tttgtttgtc 131580
```

```
tcttccagtg tgtgtgactc ttcttaattt aagtttctga aaacatactc tatctaagaa    131640
taacctgacc ttttatgaca ttgagggtca agaatctgaa ggaaaagatg aacccatttc    131700
tttgcctgac ttgctttata acttttggca aatagtttct acttctgtac ctggtcttca    131760
gatctctttc ctgctttaac taaaatgtaa tgatgtatat aatggcaaag catctttgtg    131820
gagaaaggta cctttctcct cttcctcatc aatattatgc tttggtatat cctgcctacg    131880
acatgcaaga gaattttata ataataaaag cataaaggtg ttctccagca tgaaaacatt    131940
ttgcttcact acttgatctg agggtcactg gcattacata ttttttttgc tgtttgttat    132000
aatgataata ctatgtttct acatcatgct gtattttaat ggttgaatat tatgtcatat    132060
tagatatatt ttagacatga gtcacacttt aaatataacc aatgtgaaca gaatgctgaa    132120
atgaaaatga gaagtatttt atgtaaaact aagcagtatt tatatgtgag aataataagc    132180
aaaaaaaccc atcttcgttt tgtgactaaa cagagaaatt tgtgtagatc aacttagcag    132240
ctgtctaaag taccaaaata atagatttt cactgttgat aatttaaaat aaaatgtcca    132300
tttgtatatc ttatgataca gaattaatgg attgcttcaa atgttttca gaatatgttt    132360
ttaaatagta ctgatttcat taagatgttt tgttctgaat atttctgaga actaccgtag    132420
tgtcgtttag ttttcctatt tgcgttttg gttgtttgga gtaggggata attttggttt    132480
attcatacag ttgaaaagtg tactgctatg agaatgagat tatggttaca tgtaactaca    132540
tgggcatttc atttttaaag cctctttgaa cttttgaaa tactaagaat ataaaatttt    132600
tatttttta gtttagatgt cctgaacgag tatgtttagg caaaattgag ttatttaaga    132660
atttataggc tgggcgcagt ggctcacgcc tgtaatccca gcactttggg aggccaaggc    132720
tggcggatca tgaggtcagg agatcgagac cagcctggcc aacatggtga accccatct    132780
ctactaaaaa tccaaaaaat tggccgggtg tggtggcatg tgcctgtagt cccggctact    132840
tcggaggctg aggcaacaga attgcttgaa cccgggaggc agaggttgca gtgagccgag    132900
atcgcgccac tacactctag cctgagcgac agagtgagac tccatctcca aaaaaaaaa    132960
aaaaaaaaaa gaatttacag atttctggca aaccttcttc ttgagacatt actacttttc    133020
ataccacctc tgtcctttt gaagaataaa agttttaaca ttccgtaggt taatgagaat    133080
aggacttggg cagcagcaat catccttcct gtcacctgta acccacagct tatgctttct    133140
tcctggaggt tcttgtctgc cacaaaggct cactgctgat aggaatttgt atatgatcaa    133200
aggtgtttag ttttataaaa cagttaagtc cagtcttaat tttccacatt atcactttca    133260
attttgtatt gtggattacg catttaaat aaaaaattgt gtgattgcta cattttgaa    133320
aacattttt tcaagaggcc catccgtaat ttaattgtaa agatactga caaactaact    133380
tggtttatta ttttggttat gaccccgtca tttgacttgt ctttagttgt cttaacgggg    133440
actgaatatg cgtgcaaagg cacgattgat ttatcatgct ggcttttatg caacttgtat    133500
atattttaac aattttcctg tttgctaaag gcttaggtta aaagttcatt atgattgttt    133560
atacatttct ggtgaataca tcatgattta acaagtggaa agaacatctc tttccttcca    133620
ttttctggca tactccccctt ggaatcagat ctgaaacttt taagctaaaa tttccattgc    133680
atttggagag tagttatttg tgtatgcatg cttttgagac attgtagcaa taatactgta    133740
atgttgagcc gaatctttct cctcattgtg ttcattcact gccaacatct ggcttcatct    133800
tttgatgaa tgttcattgg ttttgaaaca gcctataggg taaatactgt gtttgaggta    133860
cagatgattt tcataactac ttcctagaac atgtccattt gaagagcagt ggggccttag    133920
```

```
accccaaagt ccatttatgt gtgggcaaat aggaaatgtt gcaaacaaaa caaagcacta    133980
gatctaatgt ccagtgaaat ctggaatgaa ctagtcatta gagccggttc tttcatgcca    134040
ggaaaaagtt actcagccaa atctgaacta ctctcctgca gtttacacag gtggtattta    134100
attgctgtct gtatggaggc aggctaggag caaggctgtg gacttgttgt gattgtcact    134160
agttaatcaa gattcccttt gtggtgctta agaccctaaa aaggacacta ggagctgggc    134220
atggtggctg acacctgtaa tccaagaact tggggaggct gaagtggagg atcgcttagc    134280
ccaggtgttc aagaccagtc taggcaagat ggcgagatcc catctctacc aaaaaaaaaa    134340
aaaaaaaaaa aaaaaaaaag cccagtcatg gtggcacatg cctgtagtcc cacctacaca    134400
ggaagctgag atgggaggat cacttgagtc caggactttg aggctacagt gagctatcat    134460
ggcaccactg taatccagcc tgggtgacag agcaagaccc tgtctctatt taaaaaaaag    134520
aaaacataag aaagaattgt tttgttctat gccatcataa gccataattt aatctgctta    134580
agcatgttct tcattaaatc tgcagtgatt tatttgaatt attagacttt caaagcctta    134640
ttatatcaaa tataaacaaa atttgaagta cattcttata aactacaaca aacttacata    134700
gaagtgttaa ttttatactc atcttccctg aacaatttat attttataaa tatattaaat    134760
atattgtaat aaattttctc aaaggaacca aatactttga gtatgaattg tgcttttctt    134820
tttaagctac atcatatcta ggttttaaa acatttaatg caaacagaag aacatgcacc    134880
cagatgttgg tgacaatttt atgtcacctt ttctcattca ttaattgtta tagccatagc    134940
caaaggcatt gaaaacatag gaccactaat gactgcaaaa tgaaatcctg attattgttt    135000 ttaaatttt agtatgttta atacacatat gctaacatta ctgaacagtt aaatgataaa    135060
ataggataat tattttattc taaaaaagta ttgaccttga cctctttcta gctatcttag    135120
aaagggcttt tgtcaaaaac cttatctctt tgatgtctct ttttttgaga tggagtctct    135180
ccctgtcgcc caggctggag tgcagtggcg tgatctcagc tcactgcacg ctccgcctcc    135240
tgcgttcacg ccattctcct acctcagcct cccgagtagc taggactaca ggcgcccgcc    135300
accatgcccg gctaatttt tgtatttgt ttagtagaga tggggtttca ctgtgttagc    135360
caggatggtc ttgatctcct gacctcgtga tccgcctgcc tcagcctccc aaagtgctgg    135420
gattacaggc gtgagccact gtgcccagcc tctttttttt tttttatttt ttatttattt    135480 tttattttt ttttaatttt tgagaaggag tctccctctg ccacccaggc tggagtgcag    135540
tggcgcgatc tcagctccct gcaaactccg cctcctgggt tcaagcagtt ctcctgcctc    135600
agcctcctga gtagctggga ctacaggtgc ccgccaccac acctggctaa ttttttgtgtt    135660 tttagtagag acagggtttc accatgttgg tcaggctggt cttgaattcc cgacctcagg    135720
tgatccaccc acctcagcct cccaaagtgc tgggattaca ggcgtgagcc actgccccgg    135780
cctctttgat gtctcttaat ctaacttcca tcattgcctc tacccatcc cttctaagaa    135840 gttactttaa ttttttttcc tctcacatct actcttttt tttttttttt tttttttttg    135900
aggtagtctc actctgtcac ccattctgaa gtgcagcggt gcgatctcag ctcactgcaa    135960
catctgcctc ccaggttcaa gcggttttc tgcctcagcc tcccgagtag gtgggactac    136020
aggtgtgcgc caccacgacc ggccaatttt tgtatttta gtagagacgg ggtttcaccg    136080
tcttggccag gctgatctcg aacttctgac cttgtgattt gtctgcctag gctcccaaa    136140 gtgctgggat tacagatgtg agccaccacg cccagcctca catctactct tctaatccat    136200 ctaatttgt tttatggtga tgcttttacc tttcagaaac agtaataata caacttttcc    136260
gactaactag agccattagg aagaattaga tccagaatcc tttttgatt tgttttggt    136320
```

```
agtttaatgc agataagtaa gaaaatatag ttaagttaaa aaaaaaaaaa atgaaaagca   136380
tccataatcc ctccacctga caactgcctt ttaacatttt gatgtgtatc cttccaggtg   136440
tatttaaata cactcaaata ccctacccct ttatgtagac atgttttaat aagaaataat   136500
attcatgttt atattcttgc tatgatccta aattttgga tccattacta gataatcttt     136560
caggataatg acatttccat tagtaatgtt tttgcaaaat tgtgtgtcta ttgaattaaa   136620
cttgtaaaat agttttattt tggtacatga tttatatcaa ggttgttcag tagaatgcca   136680
tgttggtgtt tttattagat aatgatttta ttccttttac ttttaagcaa gtcagcatga   136740
caacttgaca cctaagtaca gaagaacagt gtcttccggt ttagtccttt cttttaaaat   136800
tctgtagcag tgtttaaagt gcttgtcatc tcttatgaaa atgaattatg catgaataca   136860
aaaagaaatt actaatatgt caacctttcc agaaaatttg gaaatgcac acctcaaaag    136920
gctaatttac ctttctattt cccaaattca gcatgtccca aattaccata caacaaggag   136980
acaagccctt ctttctactt tgccagtgag ttgggttttt tatactaatt tttaattgta   137040
cagtaaaaca cttttttaaag gatacatgtt aagggagtag acttgttgaa caatattttc  137100
cttgtgccag tcaaattatt gaaagtactt atatatataa ataattcagt ttttaaaatg   137160
gaaataccca atttaagaag gctggagtta atgaaaaatg gagttgtttc agaaatcaat   137220
ttttgcatac caagcaaatg tgactgggaa atgcctaata ttttccttgt tagagaaact   137280
tcctaaacag ctttatacac acacacacac acacacacac acacacacac aaacacacac   137340
acccaagcca caagcttggt ataaatttaa aatgtttatt tatacacaca cacacacaca   137400
cacacacaca cacacacacc ccaagccaca agcttggtat aaacttaaaa tgtttattta   137460
tattctgata agatgaaatt tatgcctacc aggattttta attgaatagg attgatgaaa   137520
tactaaggga aaaactttc agtcctgtgc atggctaaag gtttaaaata ctcaggaagg    137580
gccaggcacg gtggctcaca cctgtaatcc cagtgctttg ggaggctgag gcgggtggat   137640
catctgaggt cagcagttca agaccagcct agccaacatg gtaaaactcc atctctacta   137700
aaaaatacaa aaatcagcca tgcatgctgg catgcgccta taatctcagc tactagggag   137760
gctgagacag gagaattgct tgaacttggg aggcagaggt tgcagtgagc cgaagtcgtg   137820
ccactccact ccagcctggg tggcagagcg aaattctgtc tcaaaaaata aaatattcag   137880
gaagcagacc cctcaggata tcttgagctt aagcaagaga tcatgacctc tcaggtcatt   137940
atcttggaca gcacaggtcc cctctcccca cctggcaaaa agtacagaaa tagttgctcc   138000
ttcatggaga aagtctgggc agagcttttct tctggaaatg aacttttaag gtacatttttt 138060
cctatttgta gggcaatttg taaaaataag ggccggacgt ggtggctcac gcctgtaatc   138120
ccagtacttt gggaggccga ggtgggtgga ttgcttgagg ccaggagttc gagaacagcc   138180
tggccaacat ggtgaaaccc tatctctacc aaagcatggt ggcacgcacc tgtagtccca   138240
gctactgggg aggcggaggc acaagagttc catgaaccct ggaggtggag gttgcagtga   138300
gctgagattg taccactgca ctcaggcctg ggcaacagag agagactctg tctcaaaata   138360
aaaaataaaa ataaggctag tcttggactt tggtatttaa ataggaagga gtactaatat   138420
ttgtagaaat cctttagaaa tttgtgccat taatattgtc accttgtatg aaatgttgtg   138480
ttctagagga tattaaggat tcaaatttta tgttaggcac attttgagtt attttgggt    138540
gactcaatgt ctgactctac taaatgccat attagcattt aaaatgcatt tgaccttaaa   138600
tctttgttaa ttatgccatg acttggtatc caaaaataag ctgatacata catacataca   138660
```

```
tatatgtgtg tgtgtgtgtg tgtgtgtgta tatatatata tatgtatgtg tgtatatata  138720
atttatttgg tgctaggaaa tgttaaattt aatcctttaa tagatgctct ttaaaaagga  138780
gtcttgctgt atgtatatac tattaaaggg gaaactatgt ctgtgattgt agtgtgtaaa  138840
agatagtagg tgattttatt atgtactcaa tttgaggtct caaatgtagt tatcctcacc  138900
atcttactgt ctctgttagt agtttggtgt tgttttcctg gtaagtagct aaggtcctta  138960
atcattaaca cctaagcctt aattgcctta gcacaacttc ccctaaaagg gagtatcagt  139020
acttttttaaa agaaactaac agttgggctg ctaatttaat ctgctgcttc atttcccccct 139080
gttctaagcc attttatgat ggtttggtca agttgccttt tattcccctt ttagagtttt  139140
caactttcct tcacttccct ttttctgaat ttaacatcag atttacaagt tggaagattt  139200
tgttttgttt tataagtttt gcaatgctgg tgatctctta tgacttgtgc atccaaagtc  139260
aaaatgacaa aacctagtta caaattaaac acacagcttt ctgtacttaa tttgcttcag  139320
tgagatcaca gctgaggaaa ctagttctgg aatgtggtta gtgttattaa ggattttttga 139380
ctgatcatat gtttagaatc ttaaatattt atgtcaagga acactgagtg ggaaacttct  139440
ggactaggtc tggaccaaag aagcatatgt ctttgattat cttttaatcta aaagatttta  139500
tgaagactaa agttttataa atagaagttt aactgatgaa taaatcagta ttacaaataa  139560
aattaacttt attttttaacc tctctgggat ctttagccag aatgagcata tataacaaaa  139620
gcagtgaaat aatatgtgtg ggtcagaacc cactgcccctt cccactccac tctccttttc  139680
cctgattctc ctgtgttttt tccttctttta ccttatcttg gttcctttttt ttttttttttt 139740
cttttgagat ggagtctcac tctgtcgtcc aggctggagt gcagtggtgc gatctcggct  139800
cactgcaacc tccgcctcct aggttcaagc aattctctgc ctcagcttcc agagtagctg  139860
ggattacagg cgcctgctgc cacacccagc taattttttt tgtatttttta gtagagacag  139920
ggtttcacca tcttggccag gctggtcttg aactcctgac ctcgtgatca cctacctcgg  139980
cccctggttc cttttttgtc tctcttgtct tccaagctat ttttttccctt ggcttttaaa  140040
ttttcttcct accctgcttt gtgtcactgt cacttaactg gcctatcaag gaaccgaact  140100
gtattttttgt tactagtatt gatttaaagt ataagtttca catttctccc aatttattat  140160
tattatttat ttatttatttt gtttattttta ttttttgaga cggagtttcg ctcttgttgc  140220
ccaagctgga gtgcaatggt gtgatgtcgg ttcactgcaa cctccacctc ccgggttcaa  140280
gctattctcc ttccccactc tccctagtag ctgtgattac aggtgcctgc caccacgccc  140340
agctaatttt tgtattttta gtagagacag ggtttcgccg tgttggccaa gctggtctcg  140400
aactcctaac ctcaggtgat ccgcccgcct cggcctccca aaatgctggg attacaagcg  140460
tgagccaccg tgcccggctc catttctccc aatttcaaat tcaaggagga aaagaattcc  140520
tgattaaggt acttctttca gatcttttga gctagaacaa aaaaacaaag ggaaatattt  140580
ctaattaact ctttttaaat tttgtttaca acgtatgata catattttac acatcctttg  140640
tggttttttgt tcgtcttgtt tttaatcaat gccttgcaag tttaccggta tttaggtagg  140700
gaaaggattt tgttttttgtt ttttttaaaca aagcctatgt acattcactc agcttgggta  140760
tttgtgctat gcatgcaaat tagctataga ttagaaaacc gtattatagt ctttaaatac  140820
tggtaaactt aaaattgcaga gatgcctttt aaaaatgcat agtaaaaata tttcatcttt  140880
acttttctct tcaaatgatt ttaagatttt tacatttttc cagttgatga ataacttaaa  140940
ttatgagatt tcatgggcat aattattttc tatatttatt gttactttttt aatattctta  141000
atactttgct tagaaggtat ttaaaagtga aatttcaaac tttttagtac aaaatttctt  141060
```

```
gaataaaataa agttacaaaa aaaaaacaaa aacctctgag attccgtact gtatctttat   141120
gaacctccat gaacagaatt tgggatttgg gaattgcttt tccttagaca gatttagatt   141180
gttacaaatg acatttttaa gaggctgggg tggcggtagg ggttagtgct aatggtttaa   141240
cagtagggga ccatggacaa ctgtagacat cactatccag tagaacattt tgtggctggg   141300
cgcggtggct cacgcctgta gtcccagcac tttgggaggc caagacaagt ggatcacctg   141360
aggtcaggag ttcaagacca gccagaccaa catggtgaaa ccctgtctct actaaaaata   141420 caaaaagtt agccaggcgc gcctgtagtc ctagctactc aggaggctga cacaggagaa   141480
tcgcttgaac ccgggaggca gaggttgcgg tgagctgata tcacgccact gcactccacc   141540
ctgggcaaca gagcgagact ccgtctcaaa acaacaacaa aactgcactg tccaccgtat   141600
tagctactta gctacatgtg gctttttat tattcaaaaa taaattttta ggcccgggtgc  141660 agttgctcac acctgtaatc ccaacacttt gggaggccga gatggacgga tcacttgagg   141720
ccaggagttt gagaccagcc tggccaacat ggtgaaaccc cgtctctact aaaaatacaa   141780
aaattagcca ggtaatccca gctactcaga ggctgaagca ggagtatcac tttaacccag   141840
gaggcggagg ctgcagtgag ccgagatcgc tccactgcac tccagcctgg gtgacagcaa   141900
gactgggtct caaaaataaa caaacatggc cgggcgcagt ggctcatgcc tgtaatccca   141960
gcactttggg aggccgaggc ggatggatca cttgaggcca gtagttcgag accagcctgg   142020
ccaacatggt gaaacccgtc tctactaaaa atacaaaaat cagccaggca tggtgatgct   142080
tgcctatagt tccagctact cggcaggctg aggcaggaga tcgcttgaa cccgggaggc   142140 ggaggttgca gtgagccgag atggtgcccc tgcactccag cctgggcaac agagcgagac   142200
tctgtcaaaa attaaacaaa taaatacatt tttaaaatga acgtaagatt tttacaagta   142260
caacaaactc aggttcgaaa tttacatcaa atctttttaga ccaagtcagt gcctatacaa   142320
cttggaggag ctggaagtaa acttaatgag tatgatgatg atggagggcc tgttaataag   142380
ccaccaagtt agaaaaaaag gactgtctta tagacttatg ggactgtgaa gctcaggaag   142440
gcttcatcgt ttgtacatca tttgttctag ctcccagaag acgttcacta ctcttaaaaa   142500
cattcagaga ctatgttgcc acagttttct tgttaaaata ttctggcata tgttaattcc   142560
tacagtctgg aaaattttcc cagtgtataa acaaagctgc tgtatccagt ctaaactgga   142620
tatgaaggaa tattaatgcc agctgtggca ttggcagtgg atgcacaggt gatcctagaa   142680
ctggctcttt gccttgccct ttcccctgct aagagatagc tttgcagctg gagacgtaac   142740
tgttagggct ggagagttgg tggcccttag ccctacaaca cctaggatta tagaactgct   142800
ccatgtgcct agcctaaccc tctgcacacc atttacgtgg aatatacccca gagccgtcta   142860 tgctggtgac tcgcagcct tgcctaccag actgctggaa ctagggtgcc tcttcccaaa   142920
gctgtgcttg cttctctcac caatcagtcc tgcatatgtc tgtgtttgct aacacgttat   142980
atgaagaatg tggggaacta ttttggaatc atttctgtgt atgggcttat tatcttgagg   143040
gattttagga tttgtttctc aagagagggc tgggaactat accttgctag agttgtcttg   143100
agaacgctct attctcagct cattgcctcg tggaggttag ttttttatca tcggtgtgct   143160
gtccatagtc actggaagca gtgaacacat cctactctgc ttctgattct caacttactg   143220
tttttgaagc acatgaacag gccaggcacg gtggctcacg tctgtaatcc cagcactttg   143280
ggaggctgaa gtgggcggat catttgaggt caggagtttg agatcagcct ggccagcatg   143340
gcgaaacccc atctctacta aaaatacaaa aattagctgg gcgtggtggc acatgcctgt   143400
```

```
aatctcagct actcgggagg ctgaggcagg agaattgctt gaacctggga ggcagaggtt    143460
gcagtgagcc tgggcaacag agtgagtgag acttatatct caaaaaaaaa caaaaaacaa    143520
aaaactgaaa gacatgaaga aatggttttt gtaccaaggt ttggcccacg ctgagattca    143580
caaagaactg gctttcagtt cttatcttta ttttgattta aactggccca tcatgttgtc    143640
ctttgaagtt agtctagtaa atttctttcc aaagggctgg ggcactcaga agggagttta    143700
cttttctata tttatttcat aaagcaaaga tgggagatcc tccattaggg cttgggaaag    143760
taaactgagt ggcagaaggg ctcctgtgat tagctgagag agactgtggt ccttcggccc    143820
tgatgataga tccctggcct tgccacatac catacacagt gcccgcaccc ccatccccca    143880
ccacacccaa tatagtctgt gccctcagga cattgctcca gggcagtagc atggtgaggt    143940
tagcctgatg atggccttga gctaaagagt gtgcacctaa aatgcacttg tttgagtagt    144000
ttctgcctat gccttcaagt tgccttttg ggaaaaccta gtgaccgtta agagtaaatg     144060
caaactaatt tgattttaat atcatatgta gagctgtatt atatgaacca aatgctagtc    144120
tgttaagcaa tagctacact tattttttca agacaatgga tggtttaaat ggagtcatct    144180
atagaaattg gtagtggcgt gagttatgca ttgtaaccat caagaaagtt cagttgatga    144240
agtgtagagg agcgatggag gttgtcagac atcggttgtg tacatgctcc ttttctttc     144300
actttagttt ccacgggctc ccttgctcag cagtatgcgc accctaacgc taccctgcac    144360
ccacatactc cacaccctca gccttcagct accccactg gacagcagca aagccaacat     144420
ggtggaagtc atcctgcacc cagtcctgtt caggtaaggg caactcagag gtctgcatgg    144480
agtggcttct ttatcctagt atctgagtgc tttcttcagg tgccaggtat cgcatcgtca    144540
gaacacatgg catgtccacc ctcgtgaaga tggatacagc tgtgcccctg ggtggtggt     144600
tttaagaatc acatttaaag gctgggcgca gtggctcacg cctgtaatcc caccactttg    144660
ggaggccgag gcgggtggat cacgaggtca ggagattgag accatcctgg cgaacactgt    144720
gaaactccgt ctctaataaa aatacaaaaa aattagccgg gcgtggtggt gggcgcctgt    144780
agtcccagct tctcgggagg ctgaggaagg agaatggcgt gaacccggga ggcggagctt    144840
gcagtgagca gagatcgcgc cactgcactc cagcttggac aacagcgaga ctctgtctca    144900
aaaaaataaa aaattaaaaa aaatcacatt taagatacat gttgataata aggtgattgg    144960
ataagctctg gaaacttgca gtaatgaaaa atcaaattta acataaagtt cataaggcaa    145020
attcctattt gcttgggact ttttaatttc taaggtttat gtgatgaggt tattttccta    145080
tgagcttctt gaattatgtt tgctaatgga ggcagttaaa gatgtctttg atatctatca    145140
gttccctggg gcagtagtct tttttgactt tagtatgtat gctcagaagt ttctaactgc    145200
cagactgaga atcaggcttc tgtaccctag aaaggagttg tccagatggg aggcacctcc    145260
agccttgctc ttaccaccct gtacattctc ctgtactttc cagtgaccct catcataggc    145320
ccaagtgtgc aaagcttagc tttgtgggta tcccttggct gcttttcatt aaagaagttt    145380
tcctctcaat tctttcctgt cgctttgcag caccatcagc accaggccgc ccaggctctc    145440
catctggcca gtccacagca gcagtcagcc atttaccacg cggggcttgc gccaactcca    145500
ccctccatga cacctgcctc caacacgcag tcgccacaga atagtttccc agcagcacaa    145560
cagactgtct ttacgatcca tccttctcac gttcagccgg cgtataccaa cccacccac     145620
atggcccacg tacctcaggt aataccagct ttagccaact ttctgtgaag gccaagtaga    145680
atgtgaaggt tatcagtaag cagctagagg ctctcccagc taggaaaccc tgtgtgtcat    145740
gccatttgcc tgtctcccctt tccctctcaa atacacgtga tctggcccta agggaatgtt   145800
```

```
tgtgtggttt tgtcatggga tcagtgaagg tgctgattgg tcagtccttt agttttccaa  145860
ctgagacctt aaaaatatct ttgactctgg aatgcaaccc agtccttctt tcctttctgt  145920
gtctgctttg ctatgtctat atagcctcac tactatatat atgtgtacat atatattccc  145980
ctacacactt accttggaag ccaggcaggg atgatggcct tcacagagtc tcagctctcc  146040
gaagtgacta ccggggcctg tcaacttgat tgttactcac atgagttcca gacacatctc  146100
tccaattgtt ttccctggtt atccatatat ctgctttgac cataagttgt actcttgaga  146160
gggcttggcc ttggacattg gtgcagtgta actagaagct ggaagcaccc aggtggtccc  146220
atttttcttt aagagcagcc ctggaagcac tttggagctc acctccagtg taagctgcta  146280
caggtgaaag gtgtgcttgc catctcagtg gttgctgtct gcatcagctg ctgacaaagg  146340
tccctgcact ccagggccca ggggattgtc ttaatgagga aaggagctg cactgaagtt  146400 gggctctaac gctggccttg aggccctccc tggggctgtt acgggtgaat tggctgtatt  146460
agatgtctct gctactttca taacagaact ctctgaggcg gtctaagtg agacctgcca  146520 caatgaattc catttcctgt taaatagtgc gccagtgagg ctctggcaag gtgtgggcta  146580
gagatgcgac tcagttggat ctatctctca gaaggctacc ttgtaagtag agttccacag  146640
ctctgggaag tttgggcgtc ctcaccctgc aaagtttagg ttctgtggtg tagcgcactg  146700
cagttgattt gcttttgat agtggggagg gaagccggtt tggtccgtgt gggccagcgt  146760
ggtttggtgg agtcagcttc ataagagctg gggtcctgta ggtgtctacc agaggctggt  146820
ggctaagtag gcatgtgaac ttacatgtaa gtcagggatc cctaaaacct cactctgttt  146880
ttgtgctgaa agggcaaaaa ggttaacaca gggaagctca aatttgccat gtgcccgttt  146940
gaatatgtga gagtaaaaac ggcatttcat ccaaggctta tcgtagtcta gaacagtgca  147000
cagtgtggga aaaggaaac aagggctctt cctggccctg ccaaccccct gcagagctgg  147060
aatccagctg tttgggctga ctaaaatcac ctttccaact tgacagtgag tgagaccagg  147120
ttgaacttgg tacagagacg ctgggctggc ccagatgact tcaggttact cctttccatc  147180
tcactggagc cattaaaaac tccaactcct cctcctcctc ctgctccatc agcatatctc  147240
tgagagagtc acgggggcct aagagtctct tttcactgcc tggtgagcag accagaagca  147300
gagggagaga ggcaaatgaa cagaggtcca agtaattcac atacttgact gtgacagtct  147360
ctgcttatta atgtaatctg ttttcctatt tgaaagggat gttatctgca aaactacctc  147420
aggccccaca tggcagcctg attctgaagc atcattgaat cttgtatgat attaagttga  147480
gaaagctgcc cttggatcca gtgtctaatc tttgtgaaga tcttacccca tacatagaat  147540
acaatgatca gaaatgtcaa gggttaggac agcacagccc tgacttctac ccaggctcac  147600
ttgttgcctg ctccctgacc cttgcaggat ctgcccaaag gtgaagcgcg tcttcaggtc  147660
aatagataat ctactagaga ttgtccccag agaacagaac tgggccctga ggcccaccgt  147720 tgcccttttcc tgagagtccc agcccagtga aggaacaca gttgacatgt tgttgaagcc  147780
ggagatgttg cctgtatgcg taaaagagct ctctgtttca ggctcatgta cagtcaggaa  147840
tggttccttc tcatccaact gcccatgcgc caatgatgct aatgacgaca cagccacccg  147900
gcggtcccca ggccgccctc gctcaaagtg cactacagcc cattccagtc tcgacaacag  147960
cgcatttccc ctatatgacg cacccttcag gtgaggcgtg tgtgtgcagg ggccgccggg  148020
gcaccccaaa gcattctgct cgcacaggtg gaatggcagg cagggccagt gcttcaagcc  148080
ccgcatttga gaactagcaa gacccgtcca ggagtgtgca caggagggac tgtgacgatc  148140
```

-continued

```
agttcagcat cagggcctga ggcttccggg agccgagtct gtgtgtgttc tgatggtata  148200
caggatttgg cttgatgaga agcagcagca gcagcaacag cagcctgatg catgcctagg  148260
actcagttgg ccttccttgt tatgacaggc tggacagggc agtgttttcc ttcctgagtc  148320
ccaaaagtct gacatgtggg gggttattac catggcagag tttgattgta gctctggaga  148380
agatactgct gagaaagcgc tgtggatgga ctggctttga gtgtagcgtt agccccagcc  148440
cctgaacagg ggagagcgcc ctgtgattgt gctctactac ttgatggctg ccatggcgat  148500
acttcacagt ctgacctgtt attctgaaag caatactggt gcttggctaa tatttgggga  148560
gggggtttgt taaggccttt ttttctaccc catgaacaag tcttctggga gttttatctg  148620
aagtggtttt acgtctgact ggtttgtttc tacccaccca cccaaccctc cccactttgg  148680
tgcagatggg agggggaaaa gcgaattcaa ttttgagttt tgttcagcta gcacgaggat  148740
agtttacaat catgtgctgc agagacacta ggctgatgtg tggtgttgcc agttttctgt  148800
ttcaatgttc gcttttcttt ttacagtaca agcccaccac caacagcagt tgtaaggctg  148860
ccctggagga accgaaaggc caaattccct cctcccttct actgcttcta ccaactgaaa  148920
gcacagaaaa ctagaatttc atttatttg tttttaaaat atatatgttg atttcttgta  148980
acatccaata ggaatgctaa cagttcactt gcagtggaag atacttggac cgagtagagg  149040
catttaggaa cttgggggct attccataat tccatatgct gtttcagagt cccgcaggta  149100
ccccagctct gcttgccgaa actggaagtt atttatttt taataaccct tgaaagtcat  149160
gaacacatca gctagcaaaa gaagtaacaa gagtgattct tgctgctatt actgctaaaa  149220
aaaaaaaaaa aaaaaaatca agacttggaa cgccctttta ctaaacttga caaagtttca  149280
gtaaattctt accgtcaaac tgacggatta ttatttataa atcaagtttg atgaggtgat  149340
cactgtctac agtggttcaa cttttaagtt aagggaaaaa cttttacttt gtagataata  149400
taaaataaaa acttaaaaaa aatttaaaaa ataaaaaaag ttttaaaaac tgatcaagtt  149460
agtgtgtgtc tgtataagct acttctttgt aggatactta atatcaaagc aggtgtgcta  149520
agggtgcatt ttgaatatcc cggaaggtag ctgtgaaatg attttctttc ttcaccctta  149580
gttctggttc aaggtatctc tagaaaaaga caagactgag ctattctctt tggtggatta  149640
gagatctgct tcaggaggag gaaggttggc cagagttggg cagcactgaa attccacatc  149700
ctcgggctga caccgattct gtaagcttcc tttttaatat ctcctgaacc aaaatgagtg  149760
tcattagctg gaagttccca attcgggcat ttttctactt taccagtagg gggcaggaga  149820
cactcagaaa aaaattgcaa taagaaaatc cagagggcat gaaggctgaa aagatacaaa  149880
gatgtacaaa gctgcttatt gacatggatg gactcataag catttgttag tattcccaga  149940
ttgcaacggg gaggacaaag ggaagagcga gtatttgggc agggcaagga ttttgtagag  150000
acaccatggt cttaatagag cctttaaata ttatgacagc aaatcaagat tctgaaaact  150060
ttttaattca catatagcaa tttgtacatt atagcaaaat ttgcattatt caagaataag  150120
ttacttgtac agtacataaa acaatacata aaaatttgcc aaataccttc tgcctataat  150180
gatacaagat gaatccactt tatgttatca caatgtgctg tatattctaa ccaaacacag  150240
gatgtcagat gtgtccttgt taatatactc gcaagttcct ctagcttgtg ggagatgtta  150300
gagctaacac atttgcagta agggacttag tcctgaatag aaagcatgaa ggaatctcag  150360 gcaacccctca gggaagagtc caaggccttg actttaggtt aagaaactgt tatgtaaaaa  150420
tagtgttctc tggcccaaga ttttaatgat tgctattcct ttttcctacg gtccagaaat  150480
gatcaaaggc agaagattta taccagataa agccatatgg attgctggtc taaaattcaa  150540
```

```
ggcaggttag ttgacttaat tctttggtgc tggtgactgt tagtttgtaa aagttcaata   150600
agtcagatga aggaagggat ggtgccggga gctgtcaagc tgtactggtg gggtctgtaa   150660
ttagagctaa ctggagggat catgatgtct actgtccagt ttggtgttga gccatggctc   150720
tcggtagaag ttgccggctg gggcctggtc aggactggaa ggagagtggt gggatgtgct   150780
gtgcctatgg tgggctagct gcagccagtg gggtgcctgc cccacactgc tgcccacccc   150840
ttcatcagct gattctgctc ccacataaag aaaggtgttg gcttagtgtc acttcttcct   150900
agagccatgg gagttttctg tcagcatgtt tttgagctgt cctggtaact tggacgggaa   150960
gcagtctgga ggtgggtgcc ttccaaatct ctgccacaga a                       151001
```

<210> SEQ ID NO 3
<211> LENGTH: 863
<212> TYPE: DNA
<213> ORGANISM: homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t

<400> SEQUENCE: 3

```
gtctgtcggg gctctctccc cgccccctcc ggatcctggg naagnacggn ggacggggtg     60
gagacaagtg ggccttggcc cccgcacccc tctgcgttcg tgtccgaggc ggcggcgggg    120
gctcccgaac tcccctgaaa tcgtggggct ccatgtggcc tccggcagcg ttccaccctc    180
ccccacctgg ggaagggaag gggtgggag tgcccggccc cgtcccggcc ttcctccttc    240
ccccgccaga cctctccggc gcgcgggtgg tggccgatcc gcattgctgt tcgaggccgc    300
agtggagaag gcgcctgtgg aacatcgagg tcgaaacagt aacaaaggac tgcctcagtc    360
tacgatttct tttgatggaa tctatgcaaa tatgaggatg gttcatatac ttacatcagt    420
tgttggctcc aaatgtgaag tacaagtgaa aaatggaggt atatatgaag gagtttttaa    480
aacttacagt ccgaagtgtg atttggtact tgatgccgca catgagaaaa gtacagaatc    540
cagttcgggg ccgaaacgtg aagaaataat ggagagtatt ttgttcaaat gttcagactt    600
tgttgtggta cagtttaaag atatggactc cagttatgca aaaagagatg cttttactga    660
ctctgctatc agtgctaaag tgaatggcga acacaaagag aaggaccctg cagcccctgg    720
atgcaggtga actcacagcc aatgagggaa ctggaggctt tgnaaaatga cgtatctaat    780
ggatggaacc caaagatatg tttcgtttaa tgaaaaaaat tatggcgcag gggccaccgt    840
tgaaagcagt ttatttcgga tac                                            863
```

<210> SEQ ID NO 4

<400> SEQUENCE: 4

000

```
<210> SEQ ID NO 5
<211> LENGTH: 27
<212> TYPE: DNA
<213> ORGANISM: Artificial sequence
<220> FEATURE:
<223> OTHER INFORMATION: Primer

<400> SEQUENCE: 5
accaaagagt agttaatgga ggtgttc                                      27

<210> SEQ ID NO 6
<211> LENGTH: 19
<212> TYPE: DNA
<213> ORGANISM: Artificial sequence
<220> FEATURE:
<223> OTHER INFORMATION: Primer

<400> SEQUENCE: 6
agaaggtggg cgagaggaa                                               19

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
ctggccatcg ccttgccca                                               19

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccggctcgca cgccgggcgg                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
catacaccgg ctcgcacgcc                                              20
```

```
<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
ggcttcagcg acatggtgag                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgacctctgc ccaggccggg                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tgcatagatt ccatcaaaag                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
aagtatatga accatcctca                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttcacttgta cttcacattt                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctgtacttt tctcatgtgc                                               20

<210> SEQ ID NO 19
<211> LENGTH: 20
<212> TYPE: DNA
<213> ORGANISM: Artificial sequence
<220> FEATURE:
```

```
<223> OTHER INFORMATION: Synthetic oligonucleotide

<400> SEQUENCE: 19
ctggattctg tactttctc                                                    20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
ctctccatta tttcttcacg                                                   20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tctttaaact gtaccacaac                                                   20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gagtcagtaa aagcatctct                                                   20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
cagggctcca ggtccttctc                                                   20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gcatcccagg gctccaggtc                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
tcttcattat atcgaaacat                                                   20
```

```
<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gctaactggt ttgcccttgc                                                   20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gtatttttct tcctcactcc                                                   20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tgctgtgtat ttttcttcct                                                   20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
gaaatctgaa gtgtgagaag                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
cctccattaa ctactctttg                                                   20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggaacacctc cattaactac                                                   20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 32
ggcgatggcc agggaacacc                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
gtagcgagaa ggtgggcgag                                              20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agagttggga cctgactggt                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tggaagagag ttgggacctg                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ggagctggag aaccatgagc                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gagacaggag ctggagaacc                                              20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttgtgggata caaattctag                                              20

<210> SEQ ID NO 39
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 39
ggaaccccac tgaccactga                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tcttgaagcc tggaatcttt                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aacctaaaat cattcttaaa                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
agttgatcca tagattcaga                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ctggtacagt tgctgctgct                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctgccactgg tacagttgct                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
```
tttgcattgg gattcaatgt                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
gaaggctttg gctgagagaa                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
gtagtagaag gctttggctg                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tgacccacca tagatgggct                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtattgggt ataaaggttg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gtcataggta ttgggtataa                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ggatgctgag actgataatg                                              20

<210> SEQ ID NO 52
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 52
acatgaggat gctgagactg                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
aatttgggac atgcatacat                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtctccttgt tgtatggtaa                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
tgaacaggac tgggtgcagg                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gactgctgct gtggactggc                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ctgactgtac atgagcctga                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ccattcctga ctgtacatga                                               20
```

```
<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cagttggatg agaaggaacc                                                   20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
catgggcagt tggatgagaa                                                   20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
accgccgggt ggctgtgtcg                                                   20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tttgagcgag ggcggcctgg                                                   20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gctgtagtgc actttgagcg                                                   20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
agactggaat gggctgtagt                                                   20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide
```

-continued

```
<400> SEQUENCE: 65
gcgctgttgt cgagactgga                                               20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggaaatgcgc tgttgtcgag                                               20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ggcttgtact gaagggtgcg                                               20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gtggtgggct tgtactgaag                                               20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
ctgttggtgg tgggcttgta                                               20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
caactgctgt tggtggtggg                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gccttacaac tgctgttggt                                               20

<210> SEQ ID NO 72
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
ttcggttcct ccagggcagc                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ttctagtttt ctgtgcttcc                                               20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
aataaataac ttccagtttc                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gaatcactct tgttacttct                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
cagcaagaat cactcttgtt                                               20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
tttataaata ataatccgtc                                               20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
```
aagttgaacc actgtagaca        20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
atcggccacc acccgcgcgc        20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
caaagggtta attaggatct        20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
cccaaagggt taattaggat        20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
aggacagtca tttgatttgt        20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
ctttgaggac agtcatttga        20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctgacagaac aaatgatatg        20

<210> SEQ ID NO 85
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 85
tattgggtat aaaggcttga                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggtattgggt ataaaggctt                                              20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ctcttttacg catacaggca                                              20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
aggaaggcca actgagtcct                                              20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
ggtcagacgg aagcagaacg                                              20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ccacctggct gcggcgaagc                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gccgttgccg ttgctaccaa                                              20
```

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
ggcccataca ccggctcgca                                               20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gcttcagcga catggtgagg                                               20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
ggacattggc agccgcgggc                                               20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
gattccatca aaagaaatcg                                               20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
caactgatgt aagtatatga                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
ccaaatcaca cttcggactg                                               20

<210> SEQ ID NO 98
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 98
ctcatgtgcg gcatcaagta                                           20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
catttgaaca aaatactctc                                           20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
ctgatagcag agtcagtaaa                                           20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
gggccactcg agctttgtac                                           20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
aggaatatat ttattttccc                                           20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
cccatacgcg gtgaattctg                                           20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tggagcccga tccaggctgg                                           20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
agaagtggat cttgatggca                                               20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
ggagaaccat gagcagaggg                                               20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
ggcccttctg aagacatgcg                                               20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cactggatat ggaacccctc                                               20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gtgggataca aattctaggc                                               20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
actgaccact gatgaccacg                                               20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 111
ctgggtctat gagttttagg                                                    20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tggaataata ccagcttggg                                                    20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
ggcatggcaa cagcttcagt                                                    20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
taggagatgc agctggaata                                                    20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gaagcctgga atctttagcc                                                    20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ccctgcagga gagttctgcc                                                    20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ttcagaagta gaacttggct                                                    20

<210> SEQ ID NO 118
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 118
caattttgtc tttgatcaaa                                                20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
tgttactaag tattgaaggg                                                20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
aagtgacctc aggtcccctc                                                20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
atgttgattt cctaacttgc                                                20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gtataaactg gagttggctg                                                20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
gtgcaaaaca aacaggctga                                                20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
```
gactggatac atcatatttg                                          20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
ggttgcacgc ctgggctcac                                          20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
tcataggtat tgggtataaa                                          20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
ttgattcact ggcatgggcg                                          20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
gatgatgctg gtcttgccgc                                          20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
atcattctag cattaccctg                                          20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
atactaaacc aggctgggcg                                          20

<210> SEQ ID NO 131
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 131
acatgcatac atcgcatgcg                                                     20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
tagaaagaag ggcttgtctc                                                     20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
cgcatactgc tgagcaaggg                                                     20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tagctgaagg ctgagggtgt                                                     20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
caccatgttg gctttgctgc                                                     20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
actgggtgca ggatgacttc                                                     20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
cgtggtaaat ggctgactgc                                                     20
```

```
<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
ttggaggcag gtgtcatgga                                               20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tggcgcatgg gcagttggat                                               20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ctttgagcga gggcggcctg                                               20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gtcgagactg gaatgggctg                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
attcctattg gatgttacaa                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
atcttccact gcaagtgaac                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 144
tatggaatta tggaatagcc                                           20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
gcaagaatca ctcttgttac                                           20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tgtagacagt gatcacctca                                           20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
ggccaaggcc cacttgtctc                                           20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
cactgcggcc tcgaacagca                                           20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
aaattcctca ttttcttttc                                           20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
gttatagtaa tctgtaatca                                           20

<210> SEQ ID NO 151
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
aggattgtaa aatgatacag                                          20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gtaggattgt aaaatgatac                                          20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
ttatatatgt aaattatatc                                          20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aaccactgat ttatacactt                                          20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
ttaaaaacca ctgatttata                                          20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
atatagcact ctgctgtatt                                          20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
```
taccaagctt gtggcttggg                                          20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ttataccaag cttgtggctt                                          20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
cctcgatgtt ccacaggcgc                                          20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
gagttcacct gcatccaggg                                          20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
tccagttccc tcattggctg                                          20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
ggttccatcc attagatacg                                          20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ttaaacgaaa catatctttg                                          20

<210> SEQ ID NO 164
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 164
gcccctgcgc cataattttt                                              20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
ataaactgct ttcaacggtg                                              20
```